US012233255B2

(12) United States Patent
Francart et al.

(10) Patent No.: US 12,233,255 B2
(45) Date of Patent: Feb. 25, 2025

(54) HEARING PERCEPT PARAMETER ADJUSTMENT STRATEGY FOR A HEARING PROSTHESIS

(71) Applicants: Tom Francart, Leuven (BE); Hugh Joseph McDermott, East Melbourne (AU); Colette McKay, East Melbourne (AU)

(72) Inventors: Tom Francart, Leuven (BE); Hugh Joseph McDermott, East Melbourne (AU); Colette McKay, East Melbourne (AU)

(73) Assignee: Cochlear Limited, Macquarie University (AU)

( * ) Notice: Subject to any disclaimer, the term of this patent is extended or adjusted under 35 U.S.C. 154(b) by 789 days.

(21) Appl. No.: 17/306,612

(22) Filed: May 3, 2021

(65) Prior Publication Data

US 2021/0346688 A1    Nov. 11, 2021

Related U.S. Application Data

(62) Division of application No. 15/971,686, filed on May 4, 2018, now Pat. No. 10,994,126, which is a division
(Continued)

(51) Int. Cl.
*H04R 25/00*   (2006.01)
*A61N 1/05*    (2006.01)
*A61N 1/36*    (2006.01)

(52) U.S. Cl.
CPC ....... *A61N 1/0541* (2013.01); *A61N 1/36039* (2017.08); *H04R 25/356* (2013.01);
(Continued)

(58) Field of Classification Search
CPC .. H04R 25/356; H04R 25/552; H04R 25/606; H04R 25/70; H04R 2225/67;
(Continued)

(56) References Cited

U.S. PATENT DOCUMENTS

| 2009/0030484 | A1* | 1/2009 | Chambers | A61N 1/37288 |
| | | | | 607/57 |
| 2010/0111338 | A1* | 5/2010 | Ypma | H04R 25/552 |
| | | | | 381/314 |
| 2013/0243227 | A1* | 9/2013 | Kinsbergen | H04M 1/6016 |
| | | | | 381/314 |

FOREIGN PATENT DOCUMENTS

DE    102008060056 A1 *   8/2010   ......... G06F 19/3406

OTHER PUBLICATIONS

DE 102008060056 (Year: 2010).*

* cited by examiner

*Primary Examiner* — Huyen D Le
(74) *Attorney, Agent, or Firm* — Piloff Passino & Cosenza LLP; Martin J. Cosenza

(57) ABSTRACT

A prosthetic system, comprising a first sub-system configured to evoke a hearing percept based on a first principle of operation, and a second sub-system configured to evoke a hearing percept based on at least one of the first principle of operation or a second principle of operation different from the first principle of operation, wherein the first and second sub-systems are configured to independently process respective inputs indicative of an ambient sound to harmonize an estimated recipient perception of magnitude of a property of the respective evoked hearing percepts.

20 Claims, 30 Drawing Sheets

Related U.S. Application Data of application No. 14/420,431, filed as application No. PCT/IB2013/002600 on Aug. 7, 2013, now Pat. No. 9,973,865.

(60) Provisional application No. 61/680,640, filed on Aug. 7, 2012.

(52) U.S. Cl.
CPC ......... *H04R 25/552* (2013.01); *H04R 25/606* (2013.01); *H04R 25/70* (2013.01); *H04R 2225/67* (2013.01); *H04R 2460/13* (2013.01)

(58) Field of Classification Search
CPC .............. H04R 2460/13; A61N 1/0541; A61N 1/36038; A61N 1/36039
See application file for complete search history.

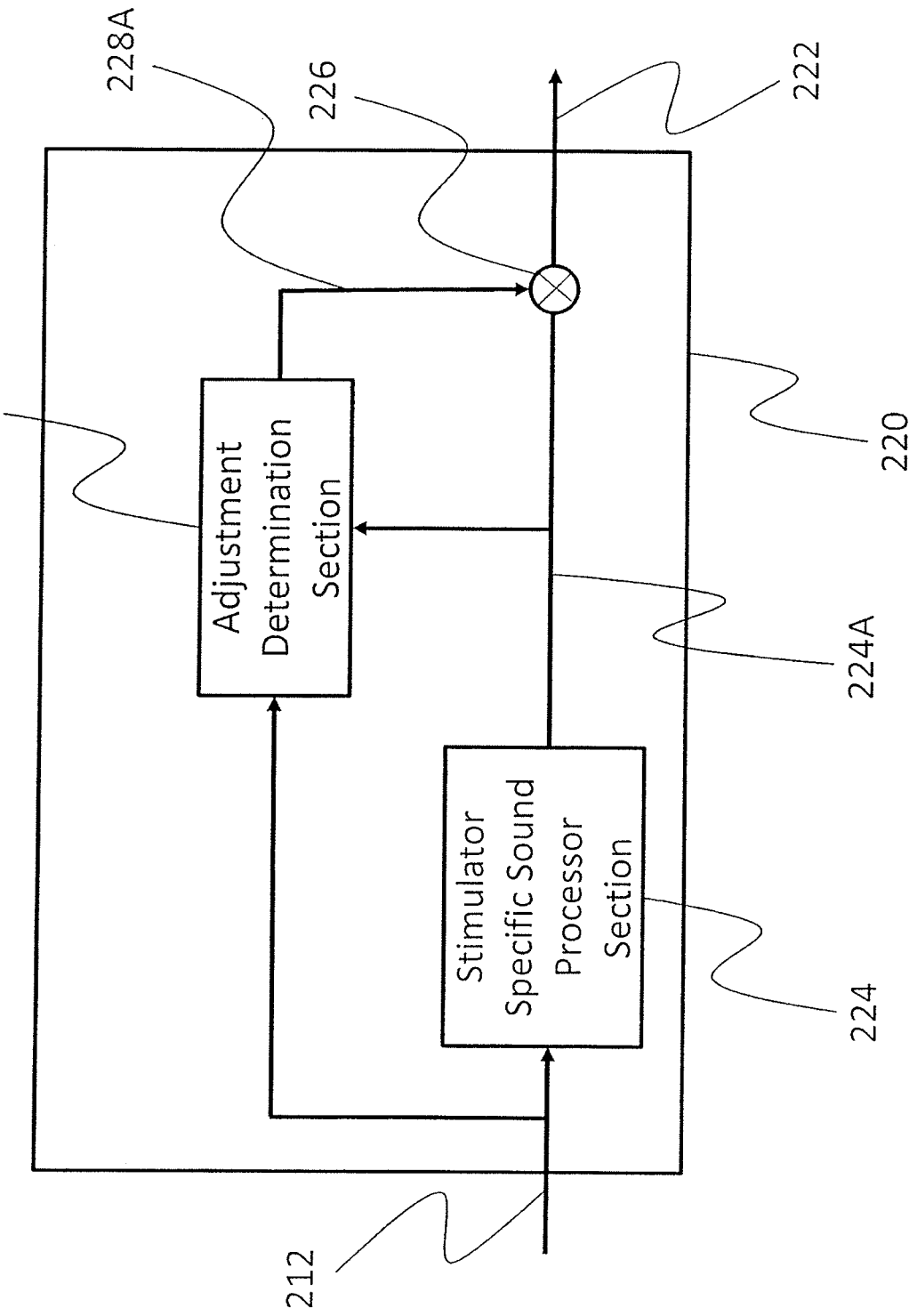

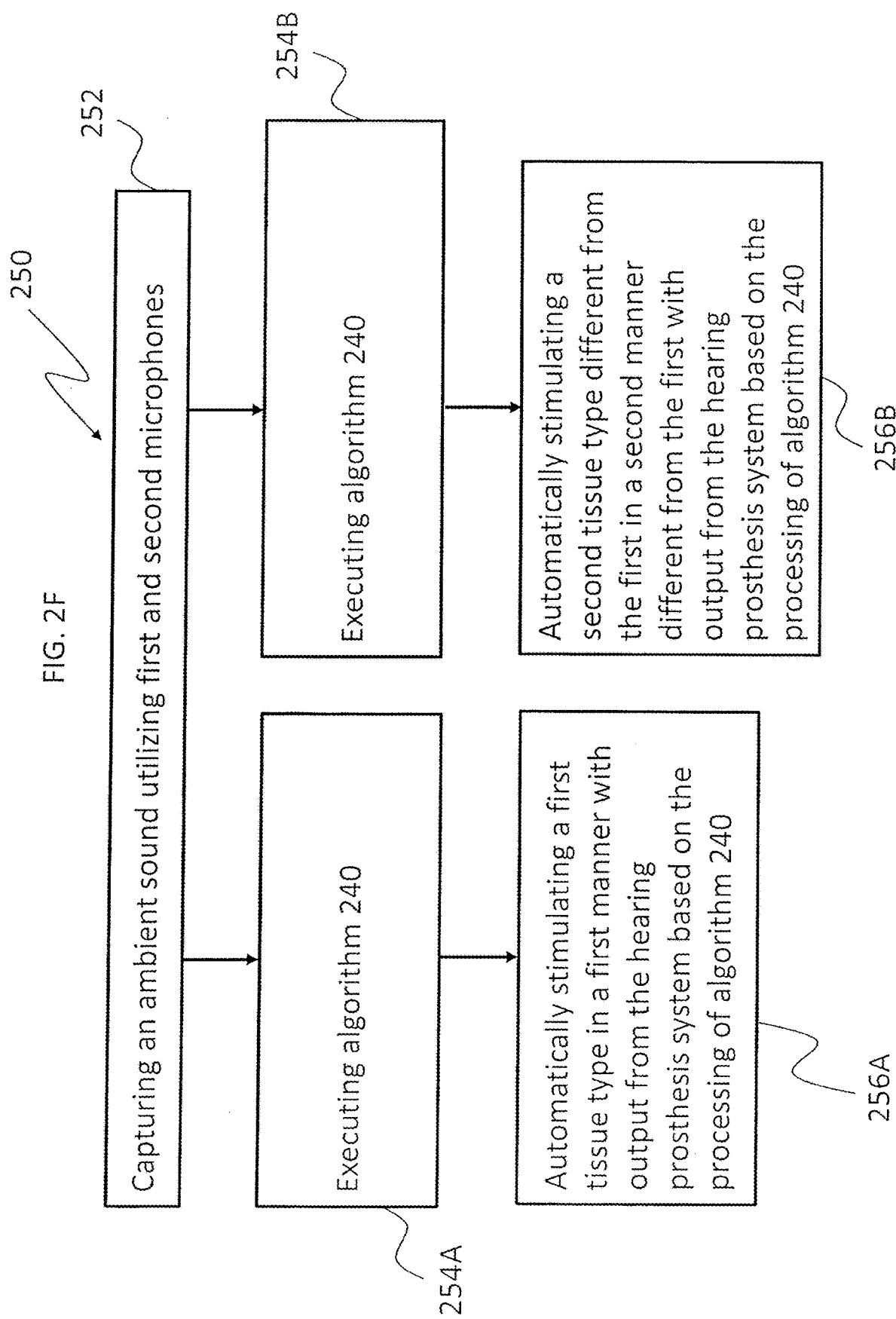

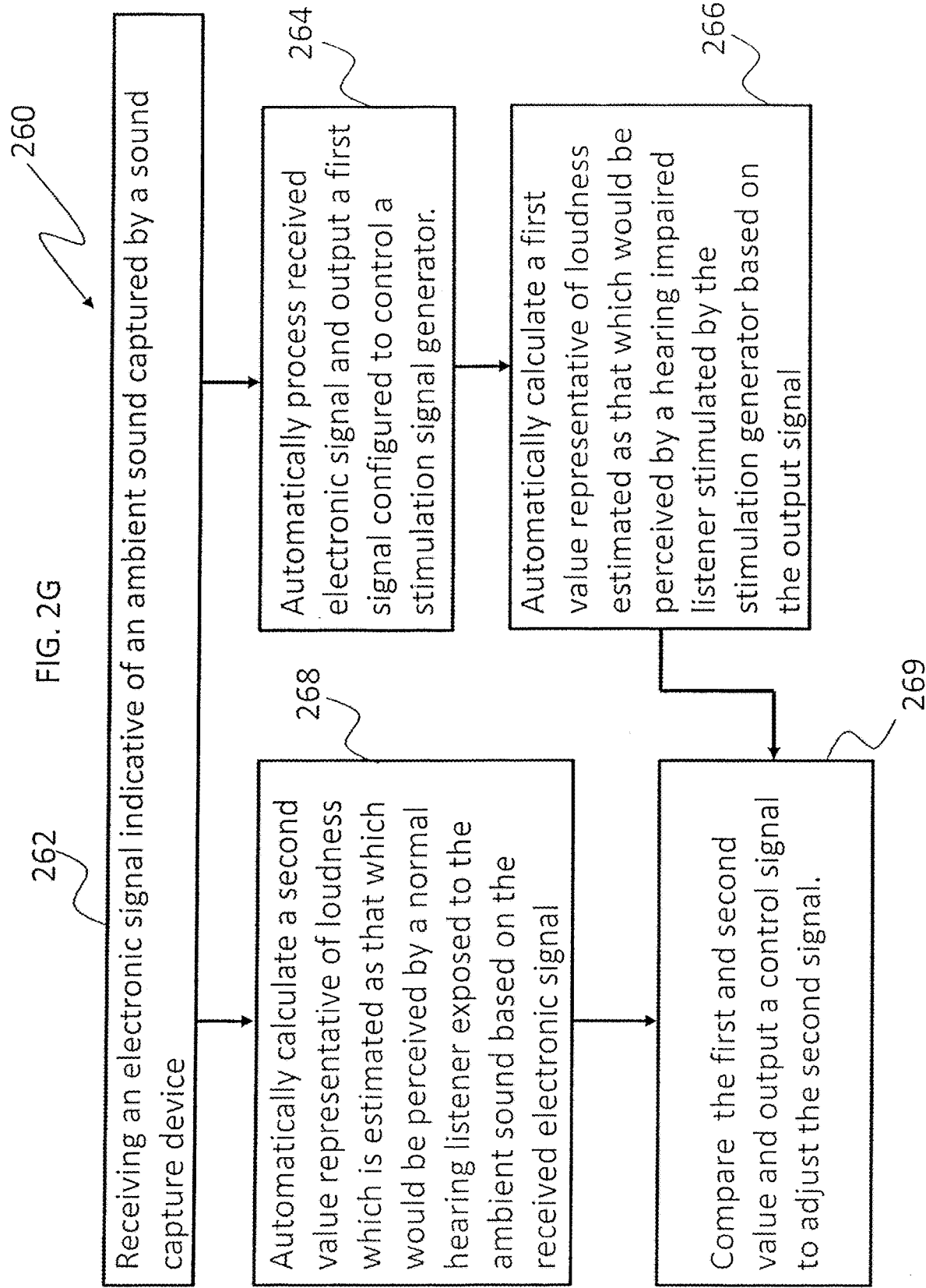

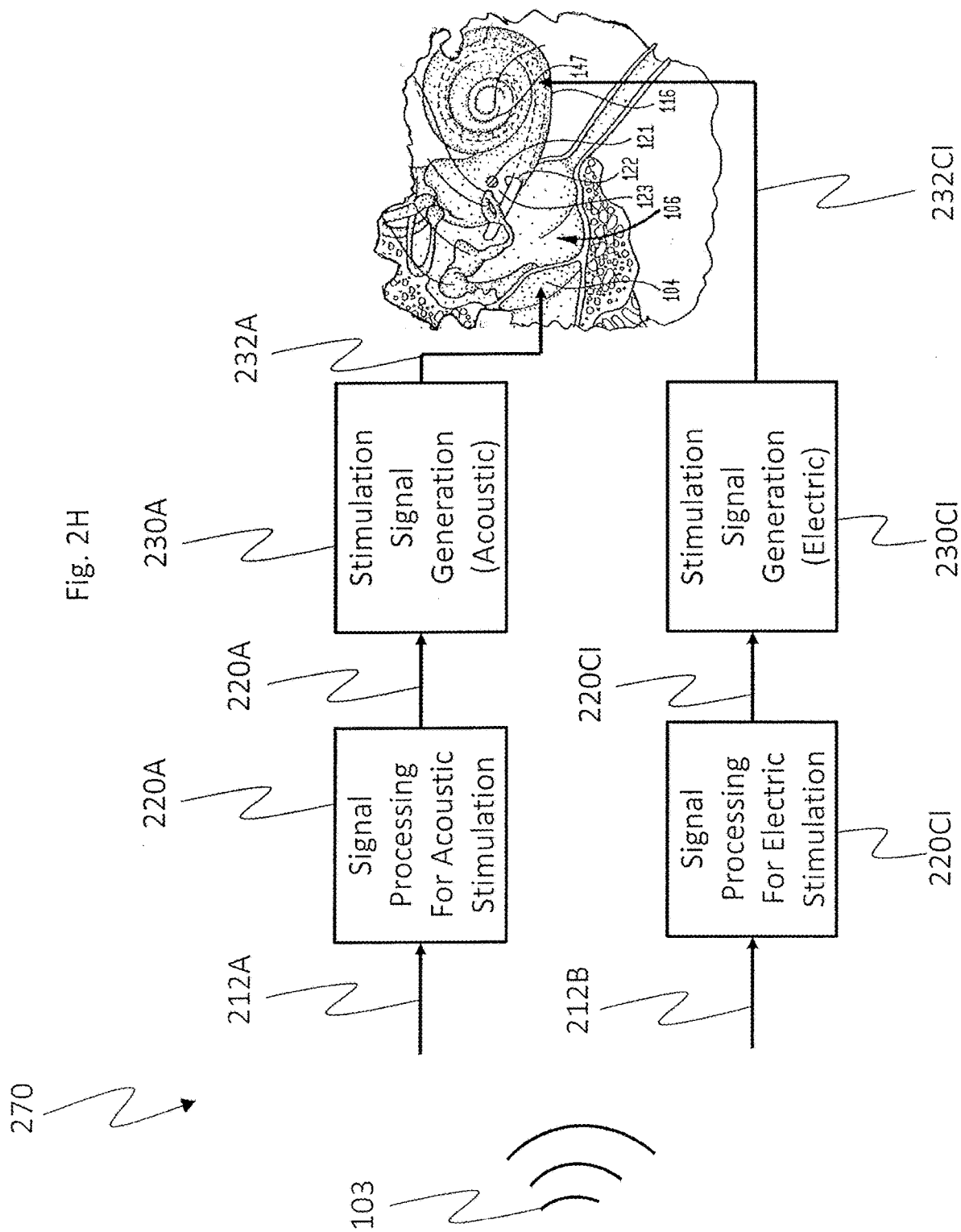

HEARING PERCEPT PARAMETER ADJUSTMENT STRATEGY FOR A HEARING PROSTHESIS

CROSS-REFERENCE TO RELATED APPLICATIONS

This application is a Divisional Application of U.S. patent application Ser. No. 15/971,686, filed May 4, 2018, which is a Divisional Application of U.S. patent application Ser. No. 14/420,431, filed Feb. 9, 2015, now U.S. Pat. No. 9,973,865, which is a National Stage of PCT/IB2013/002600, filed Aug. 7, 2013, which claims priority to U.S. Provisional Application No. 61/680,640, filed Aug. 7, 2012, the contents of each application being incorporated by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as bone conduction devices, convert a received sound into vibrations. The vibrations are transferred through the skull to the cochlea causing generation of nerve impulses, which result in the perception of the received sound. In some instances, bone conduction devices can be used to treat single side deafness, where the bone conduction device is attached to the mastoid bone on the contra lateral side of the head from the functioning "ear" and transmission of the vibrations is transferred through the skull bone to the functioning ear. Bone conduction devices can be used, in some instances, to address pure conductive losses (faults on the pathway towards the cochlea) or mixed hearing losses (faults on the pathway in combination with moderate sensoneural hearing loss in the cochlea).

Another type of device that treats conductive hearing loss is a direct acoustic cochlear implant (DACI).

A scenario exists where recipients of cochlear implants (cochlear implant users) have residual hearing in the non-implanted ear and/or in the implanted ear, such that stimulation of the ear having residual hearing with an acoustic hearing aid can evoke a hearing percept.

Bimodal auditory prosthesis systems include an auditory prosthesis fitted to the right ear of a recipient and an auditory prosthesis fitted to the left ear of a recipient, where there is residual hearing in at least one of the ears, and the prostheses are of different types (e.g., a cochlear implant and an acoustic hearing aid). In at least some situations, the auditory prosthesis fitted to each ear operates on a different principle of operation (e.g., one is a cochlear implant and the other is an acoustic hearing aid). These devices are typically developed separately and are fitted separately (e.g., parameters of the devices are adjusted based on features associated with the individual recipient, thereby "fitting" the prosthesis to the individual recipient). This results in very different growth of loudness with level with respect to the two separate ears, potentially leading to decreased wearing comfort and suboptimal perception of interaural loudness differences.

Hybrid auditory prosthesis systems include two different stimulation devices fitted to the same ear (e.g., a cochlear implant and an acoustic hearing aid).

SUMMARY

In accordance with one aspect, there is a prosthetic system, comprising: a first sub-system configured to evoke a hearing percept based on a first principle of operation; and a second sub-system configured to evoke a hearing percept based on at least one of the first principle of operation or a second principle of operation different from the first principle of operation, wherein the first and second sub-systems are configured to independently process respective inputs indicative of an ambient sound to harmonize an estimated recipient perception of magnitude of a property of the respective evoked hearing percepts.

In accordance with another aspect, there is a prosthetic system as described above and/or below, wherein: the first sub-system is configured to evoke a hearing percept based on a first principle of operation; and the second sub-system configured to evoke a hearing percept based on the second principle of operation different from the first principle of operation. In accordance with another aspect, there is a prosthetic system as described above and/or below, wherein: the first and second sub-systems are configured to automatically cause recipient perception of loudness of the respective evoked hearing percepts to correspond at least more to that which would be perceived by a normal hearing listener than would be the case without the automatic harmonization. In accordance with another aspect, there is a prosthetic system as described above and/or below, wherein: the first and second sub-systems are configured to automatically harmonize perception of magnitude of a parameter of the respective evoked hearing percepts independently of communication between the first and second sub-systems. In accordance with another aspect, there is a prosthetic system as described above and/or below, wherein the parameter is loudness.

In accordance with another aspect, there is a prosthetic system as described above and/or below, wherein: the first and second sub-systems are configured to harmonize perception of magnitude of the parameter of the respective evoked hearing percepts based on a model constructed at least in part based on a statistical sampling of a populace. In accordance with another aspect, there is a prosthetic system as described above and/or below, wherein: the first sub-system includes: a first sound processor system configured to receive first input from a first sound capture device and output a first control signal to a first stimulator based on the first input, the first output controlling a first magnitude of output of the first stimulator; and the sub-system includes: a second sound processor system configured to receive second input from a second sound capture device separate from the first sound capture device and output a second control signal to a second stimulator based on the second input, the second output controlling a second magnitude of output of the second stimulator, wherein the first and second sound processor systems are configured to output the respective control signals such that the recipient perception of the magnitude of the respective outputs of the respective stimulators is harmonized.

In accordance with another aspect, there is a prosthetic system as described above and/or below, wherein: the first sound processor system is configured to process the first input such that the first output has a magnitude corresponding to that of the first input as modified by a first standard for at least some first outputs; and the second sound processor system is configured to process the second input such that the second output has a magnitude corresponding to that of the second input as modified by a second standard for at least some second outputs.

In accordance with another aspect, there is a prosthetic system as described above and/or below, wherein: the first standard and the second standards are standards that respectively force the first output and the second output to have a magnitude such that respective stimulation to evoke a hearing percept based on the first output and the second output corresponds to that which would be perceived by a normal hearing listener for the at least some first outputs and the at least some second outputs.

In accordance with another aspect, there is a method, comprising: independently processing a first electronic signal indicative of an ambient sound; separate from the processing of the first electronic signal, independently processing a second electronic signal indicative of the ambient sound; stimulating at least one of (i) different tissue types in different manners, or (ii) tissue of different ears, with output from the hearing prosthesis system based respectively on the processed first electronic signal and the processed second electronic signal, wherein the processing of the first and second electronic signals entails independently processing the signals such that at least estimated perceived magnitudes of respective parameters of resulting hearing percepts due to the stimulation are to be at least substantially the same, and the processing of the first and second electronic signals occurs in separate hearing prostheses of the hearing prosthesis system.

In accordance with another aspect, there is a method as described above and/or below, wherein: the processing of the first and second electronic signals entails processing the signals such that the perceived magnitudes of respective parameters of resulting hearing percepts due to the stimulation are to at least substantially correspond to that of normal hearing.

In accordance with another aspect, there is hearing prosthesis system as described above and/or below, wherein processing of the first and second electronic signals entails: processing the first electronic signal based on a magnitude of the first electronic signal as modified by a first normalization standard; and processing the second electronic signal based on a magnitude of the second electronic signal as modified by a second normalization standard different from the first normalization standard.

In accordance with another aspect, there is a method as described above and/or below, wherein: processing the first electronic signal entails processing the first electronic signal according to a first sound processing strategy; processing the second electronic signal entails processing the second electronic signal according to a second sound processing strategy different from that of the first sound processing strategy; and the method further includes: adjusting results of the processing according to the first sound processing strategy and the second sound processing strategy, such that at least the estimated perceived loudness of resulting hearing percepts due to the stimulation are to be at least substantially the same.

In accordance with another aspect, there is a method as described above and/or below, wherein: the first and second electronic signals are generated by separate sound capture devices of the hearing prosthesis system.

In accordance with another aspect, there is a method as described above and/or below, further comprising at least one of: at least one of automatically halting or automatically varying the adjustment of the results of the processing in the event that a slope of the estimated perceived loudnesses over a period of time is above a threshold; limiting a maximum automatic adjustment of results of the processing to a maximum amount between two processing frames of the automatic processing; or limiting at least one of a minimum or a maximum automatic adjustment of the processing to a value lower than that which would otherwise be the case in the absence of the limit.

In accordance with another aspect, there is a method as described above and/or below, wherein the method is executed in a hybrid hearing prosthesis system.

In accordance with another aspect, there is a method as described above and/or below, wherein: the action of processing the first electronic signal indicative of ambient sound is executed in a cochlear implant; the action of processing the second electronic signal indicative of the ambient sound is executed in an acoustic hearing aid; the method is executed as part of a fitting method of a recipient; and the fitting method includes an action of at least one of setting or adjusting a first parameter of the cochlear implant and an action of at least one of setting or adjusting a second parameter of the acoustic hearing aid during a single fitting session.

In accordance with another aspect, there is a method as described above and/or below, wherein the adjusted parameters result in the processing resulting in the processing the signals such that the at least estimated perceived magnitudes of respective parameters of resulting hearing percepts due to the stimulation are to be at least substantially the same and the at least estimated perceived magnitudes of respective parameters of resulting hearing percepts due to the stimulation would not be the same in the absence of setting the parameter.

In accordance with another aspect, there is hearing prosthesis system, comprising: a first sub-system configured to evoke a hearing percept based on a first principle of operation; and a second sub-system configured to evoke a hearing percept based on a second principle of operation different from the first principle of operation, wherein the first sub-system is configured to independently adjust magnitudes of outputs of the first sub-system based on an ambient sound and the second sub-system is configured to independently adjust magnitudes of outputs of the second sub-system stimulation system also based on the ambient sound to provide a recipient of the hearing prosthesis system a perception of sound in at least about the center of the head when the ambient sound originates straight ahead of the recipient.

In accordance with another aspect, there is hearing prosthesis system as described above and/or below, wherein: the first sub-system is a cochlear implant system; and the second sub-system is a non-electric stimulation system separate from the cochlear implant system and configured to evoke a hearing percept.

In accordance with another aspect, there is hearing prosthesis system as described above and/or below, wherein: the prosthesis system is a bimodal system.

In accordance with another aspect, there is hearing prosthesis system as described above and/or below, wherein: the hearing prosthesis system is configured to adjust magnitudes of outputs of the first sub-system based on an ambient sound and magnitudes of outputs of the second sub-system also based on the ambient sound thereby providing a recipient of the hearing prosthesis system effectively consistent interaural level cues when the ambient sound originates from directions other than straight ahead of the recipient for a plurality of directions substantially to the left and to the right of straight ahead.

In accordance with another aspect, there is hearing prosthesis system as described above and/or below, wherein: the hearing prosthesis system is configured to at least one of automatically halt or automatically limit the automatic adjustment of magnitudes of the outputs in the event that at least one of an automatically adjusted magnitude would be below a threshold or a target magnitude would be below a threshold.

In accordance with another aspect, there is hearing prosthesis system as described above and/or below, wherein: the first sub-system and the second sub-system are independent sub-systems of the hearing prosthesis system.

In accordance with another aspect, there is hearing prosthesis system as described above and/or below, wherein: the first sub-system is a cochlear implant system fitted to a first ear of a recipient; and the second sub-system is an acoustic hearing aid fitted to an opposite ear of the recipient.

In accordance with another aspect, there is a method as described above and/or below, wherein: the action of processing the first electronic signal indicative of ambient sound is executed in a cochlear implant; the action of processing the second electronic signal indicative of the ambient sound is executed in an acoustic hearing aid; the method is executed as part of a fitting method of a recipient; and the fitting method includes an action of at least one of setting or adjusting a first parameter of the cochlear implant and an action of at least one of setting or adjusting a second parameter of the acoustic hearing aid such that the processing of the first and second electronic signals results in processing the signals such that at least the estimated perceived magnitudes of respective parameters of resulting hearing percepts due to the stimulation are to be at least substantially the same.

In accordance with another aspect, there is a method as described above and/or below, wherein: the action of processing the first electronic signal indicative of ambient sound is executed in a cochlear implant; the method is executed as part of a fitting method of a recipient; and the fitting method includes: setting a reference stimulus to a comfortable level of a recipient of the cochlear implant; performing a recipient-specific cochlear implant loudness balancing task using stimuli of different bandwidths; and determining a recipient-specific slope of a loudness growth function used in a loudness model that is used to estimate loudness evoked by stimulation of the cochlear implant based on the loudness balancing task.

In accordance with another aspect, there is a method as described above and/or below, wherein: the processing of the first and second electronic signals entails processing the signals based on the recipient-specific slope of the loudness growth function used in the loudness model such that at least estimated perceived magnitudes of respective parameters of resulting hearing percepts due to the stimulation are to be at least substantially the same.

In accordance with another aspect, there is a method as described above and/or below, wherein: the action of processing the first electronic signal indicative of ambient sound is executed in a cochlear implant; the method is executed as part of a fitting method of a recipient; and the fitting method includes: setting a reference stimulus to a comfortable level of a recipient of the cochlear implant; performing a recipient-specific cochlear implant loudness balancing task using stimuli of different bandwidths; and determining a recipient-specific slope of a perception of loudness growth resulting from activation of the cochlear implant based on the loudness balancing task.

BRIEF DESCRIPTION OF THE DRAWINGS

Some embodiments are described below with reference to the attached drawings, in which:

FIG. 2B is a block diagram of a component of the exemplary hearing prosthesis system according to FIG. 2A;

FIG. 2F is a flowchart representing another exemplary algorithm according to an exemplary embodiment;

FIG. 2G is a flowchart representing another exemplary algorithm according to an exemplary embodiment;

FIG. 2H is a functional diagram of an exemplary embodiment;

DETAILED DESCRIPTION

Figure 1:
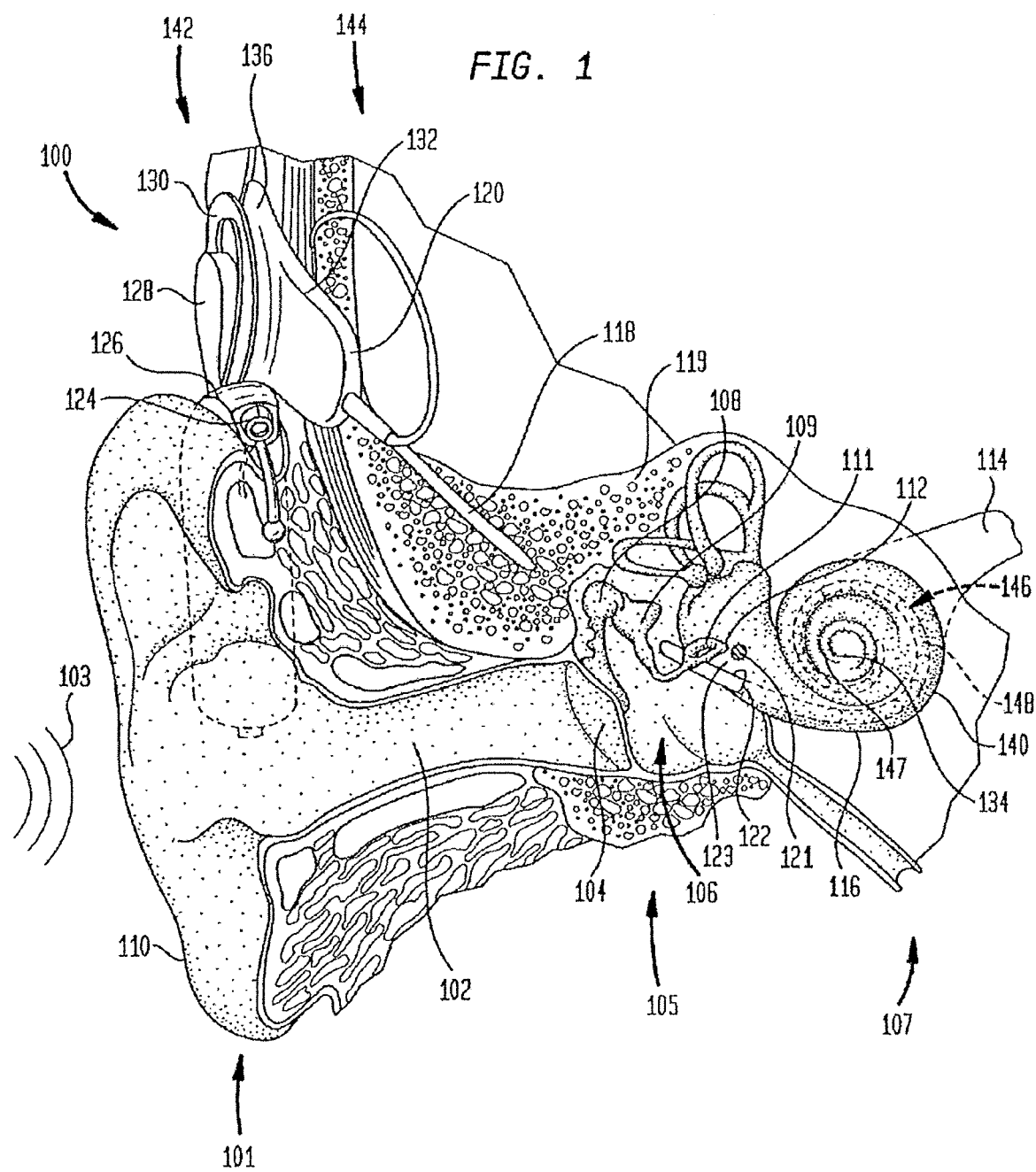
FIG. 1 is a perspective view of an exemplary hearing prosthesis applicable to at least some embodiments.

FIG. 1 is a perspective view of a cochlear implant 100, implanted in a recipient having an outer ear 101, a middle ear 105 and an inner ear 107. Components of outer ear 101, middle ear 105 and inner ear 107 are described below, followed by a description of cochlear implant system 100.

In a fully functional ear, outer ear 101 comprises an auricle 110 and an ear canal 102. An acoustic pressure or sound wave 103 is collected by auricle 110 and is channeled into and through ear canal 102. Disposed across the distal end of ear canal 102 is the tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external headpiece coil unit 128. External headpiece coil unit 128 comprises an external circular shaped coil 130 and, preferably, a magnet (not shown) secured directly or indirectly to external coil 130. Sound processing unit 126 processes the output of microphone 124 that is positioned, in the depicted embodiment, adjacent to the auricle 110 of the recipient. Sound processing unit 126 generates encoded signals, which are provided to the headpiece coil unit 128 via a cable (not shown).

Internal component 144 comprises internal receiver unit 132 including an implant coil 136, a stimulator unit 120, and an elongate electrode assembly 118. The internal receiver unit 132 may comprise a magnet (also not shown) fixed concentrically relative to the implant coil 136. The stimulator unit 120 is hermetically sealed within a biocompatible housing 132, sometimes collectively referred to as the implant unit. The implant coil 136 receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through the mastoid bone 119, and is implanted into cochlea 140. In some embodiments electrode assembly 118 may be implanted at least in basal region 116, and sometimes further. For example, electrode assembly 118 may extend towards apical end of cochlea 140, referred to as the cochlear apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises an electrode array 146 comprising a series of longitudinally aligned and distally extending electrodes 148, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

Because the cochlea is tonotopically mapped (that is, partitioned into regions each responsive to stimulus signals in a particular frequency range), each electrode of the implantable electrode array 146 delivers a stimulating signal to a particular region of the cochlea. In the conversion of sound to electrical stimulation, frequencies are allocated to individual electrodes of the electrode assembly that lie in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit 126, that is, specific frequency bands with their associated signal processing paths, are mapped to a set of one or more electrodes to stimulate a desired nerve fiber or nerve region of the cochlea. Such sets of one or more electrodes for use in stimulation are referred to herein as "electrode channels" or "stimulation channels."

In cochlear implant 100, external coil 130 transmits electrical signals (i.e., power and stimulation data) to internal coil 136 via an inductive RF channel. Internal coil 136 is typically a closed loop wire antenna coil of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Cochlear implant 100 can be used in a bimodal hearing prosthesis system, with the cochlear implant 100 fitted to one of the left or right ear, and another hearing prosthesis having a different principle of operation (e.g., an acoustic hearing aid) can be fitted to the other of the left or right ear. Alternatively, in a hybrid system, a cochlear implant and another hearing prosthesis having a different principle of operation can be fitted to one or both ears (the latter being a bilateral hybrid). With respect to a cochlear implant and another hearing prosthesis having a different principle of operation being fitted to one ear, a hearing prosthesis can be fitted to the other ear as well (a hearing prosthesis having a different principle of operation from a cochlear implant).

Figure 2A:
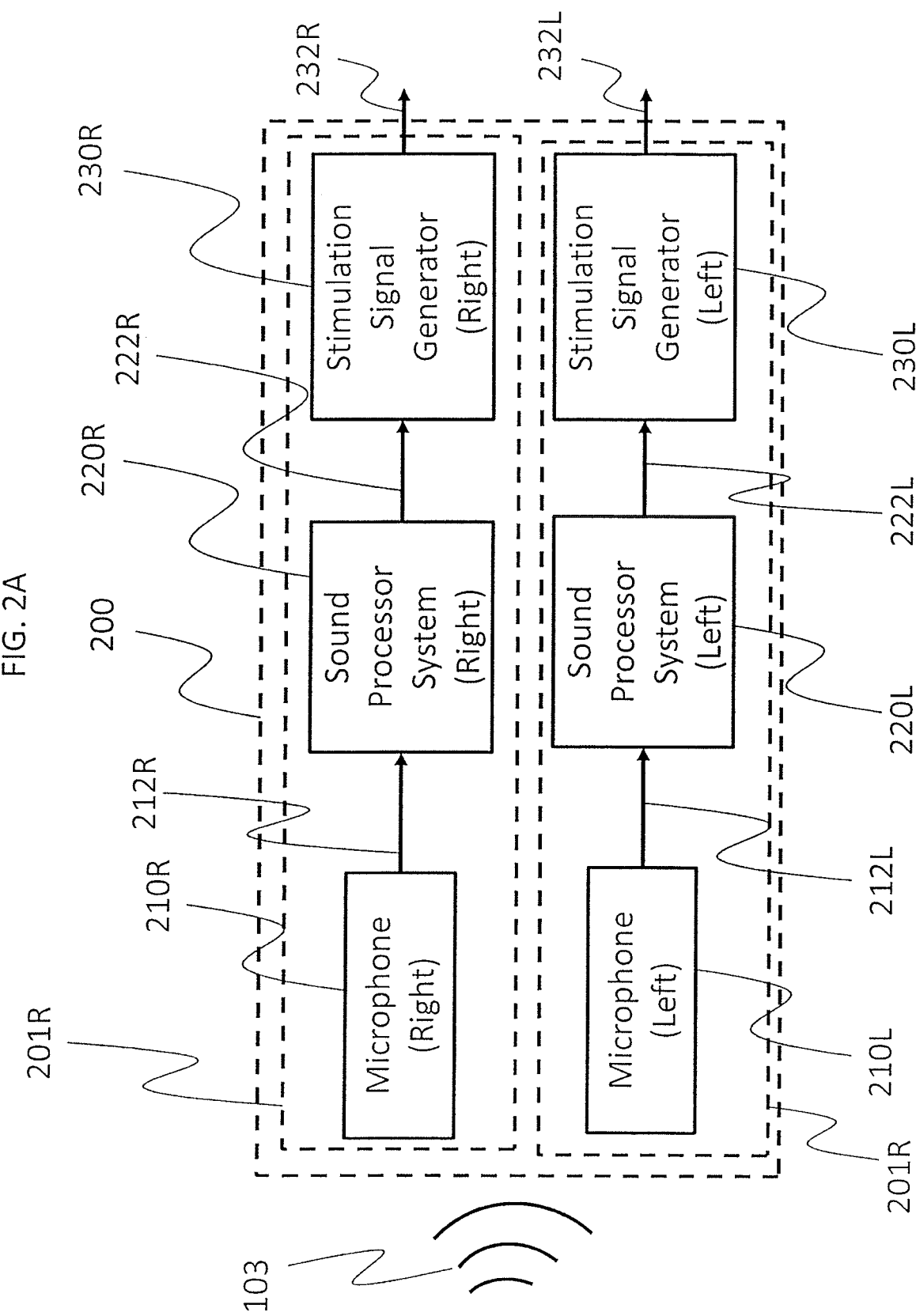
FIG. 2A is a block diagram of an exemplary hearing prosthesis system according to an embodiment.

FIG. 2A is a block diagram of an exemplary bimodal implant system 200 according to an exemplary embodiment. It is noted at this time that the examples detailed herein are examples, and embodiments can differ from these examples. Any device, system or method, including various arrangements of hearing prostheses that can be utilized to enable the teachings detailed herein and/or variations thereof can be used in some embodiments.

Bimodal implant system 200 includes subsystems 201R and 201L. The modifiers "R" and "L" refer to right and left, respectively (as in right side ear of the recipient and left side ear of the recipient, respectively). In at least some embodiments detailed herein, each of these subsystems corresponds to a separate hearing prosthesis that can operate independently of the other. For example, subsystem 201R can operate in the absence of subsystem 201L, and vice a versa.

In an exemplary embodiment, subsystem 201R corresponds to the cochlear implant 100 detailed above with respect to FIG. 1, and thus corresponds to an electric stimulation system. In an exemplary embodiment, subsystem 201L corresponds to an acoustic hearing aid, and thus corresponds to a non-electric stimulation system. It is noted that in some embodiments, this arrangement can be reversed (i.e., the subsystem 201R is the acoustic hearing aid and subsystem 201L is the cochlear implant 100).

Still referring to FIG. 2A, it can be seen that each subsystem includes a microphone (210R and 210L, respectively). In an exemplary embodiment, the microphones can correspond to microphone 124 detailed above. Consistent with the embodiment of FIG. 2A, which presents two separate hearing prostheses that operate independently and separately from one another (i.e., the subsystems are independent subsystems—the sub-systems are able to function in the complete absence of the other sub-system, and, accordingly, all processing actions of one sub-system can be executed separately or independently from those of the other sub-systems—indeed, the sub-systems have separate sound processors and in some embodiments, are completely separate hearing prostheses), each microphone captures an ambient sound that originated acoustic pressure/soundwave 103 (which as noted above, would normally be collected by the auricles 110 (left and right side) of a person having normal hearing. Accordingly, in an exemplary embodiment, the first and second sub-systems are configured to automatically perform some and/or all of the functionalities detailed herein and/or variations thereof (e.g., evoke hearing percepts such that perception of magnitude of a parameter of the respective evoked hearing percepts correspond to that of a normal hearing listener; automatically harmonize perception of magnitude of a parameter of the respective evoked hearing percepts, etc.) independently of communication between the first and second subsystems 201R and 201L.

The captured ambient sound is converted by the microphones 210R and 210L into audio signals to 212R and 212L, respectively. These can be electrical signals, or can be optical signals or any other signal that enable communication between the microphones and their respective sound processors (220R and 220L).

Upon receipt of the respective audio signals, the respective sound processors 220R and 220L implement one or more sound coding/sound processing strategies to translate the respective audio signals into respective embryonic stimulation information signals (described in greater detail below). In an exemplary embodiment, sound processors 220R or 220L can individually correspond to sound processing unit 126 detailed above, although the functionality will differ in one of them because such is utilized for an acoustic hearing aid or other non-electrical stimulation system than when used for the cochlear implant as detailed above.

In an exemplary embodiment, the respective signal processors can modify (adjust) these embryonic stimulation information signals according to the teachings detailed herein and/or variations thereof into output stimulation information signals (modified/adjusted signals) 222R and 222L, respectively. The signal processors operate independently of one another, because they are separate from one another. Thus, the adjustments are performed independently of the other. This modification is performed such that at least a target, which can be based on an estimated recipient perception of a magnitude of a property (e.g., loudness) of hearing percepts evoked by the respective subsystems (also described in greater detail below) corresponds to that of a normal hearing person, at least when certain conditions are met. That said, in an alternate embodiment, also as detailed below, the estimated recipient perception of a magnitude of the property of the hearing percepts evoked by the respective subsystems corresponds to another target loudness different from that of a normal hearing person. For example, the normal hearing target can be transformed to another target.

By way of example, for embryonic stimulation information signal 222R, a loudness estimate is developed for a hearing percept evoked by a cochlear implant receiving the embryonic stimulation information signal. Also, based on the sound captured by the hearing prosthesis (e.g., sound captured by a microphone) upon which the embryonic stimulation information signal 222R is based, a loudness estimate is developed for a normal hearing person. These loudness estimates are utilized to adjust the embryonic signal 222R such that the estimated hearing percept evoked by a cochlear implant receiving the adjusted embryonic stimulation information signal is consistent with the loudness estimate developed for the normal hearing person (or other target).

Still further, for the embryonic stimulation information signal 222L, a loudness estimate is developed for a hearing percept evoked by an acoustic hearing aid receiving the embryonic stimulation information signal. Also, based on the sound captured by the hearing prosthesis (e.g., sound captured by a microphone) upon which the embryonic stimulation information signal 222L is based, a loudness estimate is developed for a normal hearing person. These loudness estimates are utilized to adjust the embryonic signal 222L such that the estimated hearing percept evoked by an acoustic hearing aid receiving the adjusted embryonic stimulation information signal is consistent with the loudness estimated developed for the normal hearing person (or other target).

"Estimate" and "target" recipient perception is utilized because it is recognized that in at least some embodiments, it cannot be known for certain whether it exactly corresponds to normal hearing (but "estimate" and "target" recipient perception includes embodiments where it can be known for certain whether it exactly corresponds to normal hearing). In an exemplary embodiment, this means that target/estimated recipient perception of a magnitude of a property (e.g., loudness) of hearing percepts evoked by the respective sub-systems (also described in greater detail below) is harmonized. In an exemplary embodiment, this is performed automatically, separately and independently via the devices, systems and/or methods detailed herein and/or variations thereof, as will be further detailed below. Accordingly, in an exemplary embodiment, the first and second subsystems 201R and 201L are configured to automatically, separately and independently cause target recipient perception of loudness of the respective evoked hearing percepts to correspond at least substantially more (which includes corresponding exactly) to that which would be perceived by a normal hearing listener, at least based on an estimate thereof. Is noted that in an alternate embodiment, this action can be performed in a non-automatic way.

Still referring to FIG. 2A, the output stimulation information signals 222R and 222L are supplied to respective stimulation signal generators 230R and 230L. Accordingly, signals 222R and 222L are control signals, as these signals are used to control the signal generators. In an exemplary embodiment, stimulating signal generator 230R can correspond to stimulator unit 120 and electrodes 148 and accompanying components of cochlear implant 100, which, as noted above, generates stimulation signals which are applied by electrodes 148 to cochlea 140, thereby stimulating auditory nerve 114. In an exemplary embodiment, stimulating signal generator 230L can be the speaker of an acoustic hearing aid. The stimulation signal generators 230R and 230L respectively output stimulation signals 232R and 232L. In an exemplary embodiment, when the sub-system 201R is a cochlear implant, signal 232L is an electrical current. Further, when the sub-system 201L is an acoustic hearing aid, the signal 232L is a pressure wave. (In the case of a DACI, the signal can be mechanical vibrations.) Any stimulation signal generators can be used providing that the stimulation signal generators stimulate tissue based on independent signal processing relative to that of the other signal generator.

FIG. 2B provides additional details of an exemplary embodiment of sound processor systems 220R and 220L. It is noted that the details of FIG. 2B are exemplary, as with the other details herein, and other sound processor systems can be utilized. Any device, system or method that can be utilize to enable or otherwise achieve the teachings detailed herein and/or variations thereof with respect to the sound processor systems can be utilized in at least some embodiments.

Sound processor system 220 can correspond to either or both of sound processor systems 220R and 220L. The input 212 can correspond to the signals 212R and/or 212L detailed above, and the output 222 can correspond to the signals 222R and/or 222L detailed above.

As can be seen, audio signal/input signal 212 is input into the sound processor system 220 from the microphone (via wire and/or wirelessly, etc.). The signal is sent to the stimulator specific sound processor section 224. In an exemplary embodiment, the stimulator specific sound processor section 224 corresponds to a traditional sound processor utilized in a modern hearing prosthesis. By way of example only and not by way of limitation, the stimulator specific sound processor section 224 can be a sound processor that processes signal 212 according to a stimulation-specific sound processing strategy. By stimulation-specific sound processing strategy, it is meant a sound processing strategy that is utilized for a specific type of stimulation, such as, for example, stimulation afforded by a cochlear implant (electrical stimulation). Another example of such a specific stimulation strategy would be that utilized for stimulation afforded by an acoustic hearing aid (acoustic stimulation). Exemplary commercially available strategies correspond to, by way of example only and not by way of limitation, the ACE sound processing strategy with respect to cochlear implants, and strategies based on the NAL-RP rule and/or NAL-NL1 rule, with respect to acoustic hearing aids. In an exemplary embodiment, linear or compression hearing aid strategies can be used. Any strategy of sound processing and/or any sound processing method and/or system can be utilized in some embodiments of the stimulator specific sound processing section 224, providing that the teachings detailed herein and/or variations thereof can be practiced. Is further noted that while the embodiments of FIG. 2B are detailed in terms of a stimulator specific sound processor section, other embodiments can include a sound processor section that is not stimulator specific. Any device, system and/or method that can be utilized to implement the teachings detailed herein and/or variations thereof can be utilized in some embodiments.

According to the embodiment of FIG. 2B, the output of stimulator specific sound processor section 224 (or non-stimulator specific sound processor section) is provided to the stimulation signal generator with modification by signal adjuster 226. In an exemplary embodiment, signal adjuster 226 adjusts the output signal 224A, where signal 224A corresponds to the embryonic stimulation information signal detailed above. Thus, sound processor system 220 is configured to modify/adjust the embryonic stimulation information signal into output stimulation information signal 222.

In the embodiment of FIG. 2B, this adjustment is such that the target magnitude/estimated magnitude of a property (e.g. loudness) of the respective evoked hearing percept evoked by the modified signal being provided to the stimulation signal generator (e.g., generators 230R and 230L) corresponds to that which would be the case (or at least estimated to be the case) for a normal hearing person. In an exemplary embodiment, where both sound processor systems 220R and 220L adjust the output signal 224A in such a manner, the recipient perception of magnitude of a property (e.g. loudness) of the respective evoked hearing percepts is harmonized between the two subsystems.

Some aspects associated with the modification of the embryonic stimulation information signal(s) will now be described.

Still referring to FIG. 2B, as can be seen, sound processor system 220 includes an adjustment determination section 228. Input signal 212 is provided to the adjustment determination section 228 as shown, although in an alternate embodiment, a modified signal provided from the stimulator specific sound processing section 224 or from another component of the hearing prosthesis might be provided. Any signal or modified signal that will enable the teachings detailed herein and/or variations thereof can be provided to the adjustment determination section 228.

It is noted that the term "adjustment" as used herein encompasses a variety of specific signal modification schemes. By way of example, adjustment encompasses the application of gain. Any modification to a signal that results in at least the estimated/target (including actual) hearing percept to be different from that which would otherwise be the case is encompassed by the term "adjustment."

Adjustment determination section 228 evaluates signal 212 and determines a loudness (e.g., determines or otherwise calculates a value representative of loudness, at least with respect to an estimated loudness) which would be perceived (or at least estimated to be perceived) by a normal hearing listener exposed to an acoustic wave captured by the microphone that resulted in the signal 212.

Adjustment determination section 228 also receives embryonic stimulation information signal 224A (although in an alternate embodiment, it receives a signal akin to that produced by normal hearing loudness calculation section 223 as will be detailed below). The adjustment determination section 228 makes a comparison between data based on signal 212 and data based on signal 224A (which includes a direct comparison of the actual signals) and calculates or otherwise determines the modification that can be made to a magnitude to signal 224A such that a property (e.g., loudness) of the respective evoked hearing percept evoked by the modified signal 222 being provided to the stimulation signal generator corresponds to that which would be the case for a normal hearing person, at least based on an estimate thereof. Adjustment determination section 228 then outputs a control signal 228A to adjuster 226 to adjust the signal 224A into signal 222 in order to achieve or otherwise attempt to achieve the aforementioned utilitarian result vis-à-vis the respective evoked hearing percept. Thus, adjustment determination section 228 enables the automatic adjustment of magnitudes of outputs of sub-systems 201R and 201L based the ambient sound that produces soundwave 103 which is received by microphones 210R and 201L and converted into signals 212R and 212L, respectively.

Some additional specific features of the adjustment determination section 228 will now be described with reference to FIG. 2C. For example, section 228 includes a normal hearing loudness calculation section 223 which is configured to evaluate signal 212 from the microphone and determine a target loudness (e.g., determines or otherwise calculates a value representative of loudness) that is estimated as being perceived by a normal hearing listener (including that which would be perceived by a normal hearing listener) exposed to an acoustic wave captured by the microphone that resulted in the signal 212. Section 223 outputs a signal 223A which indicates that loudness (estimated or actual). In an exemplary embodiment, this determination is made utilizing a normal-hearing loudness model as detailed below.

Figure 2C:
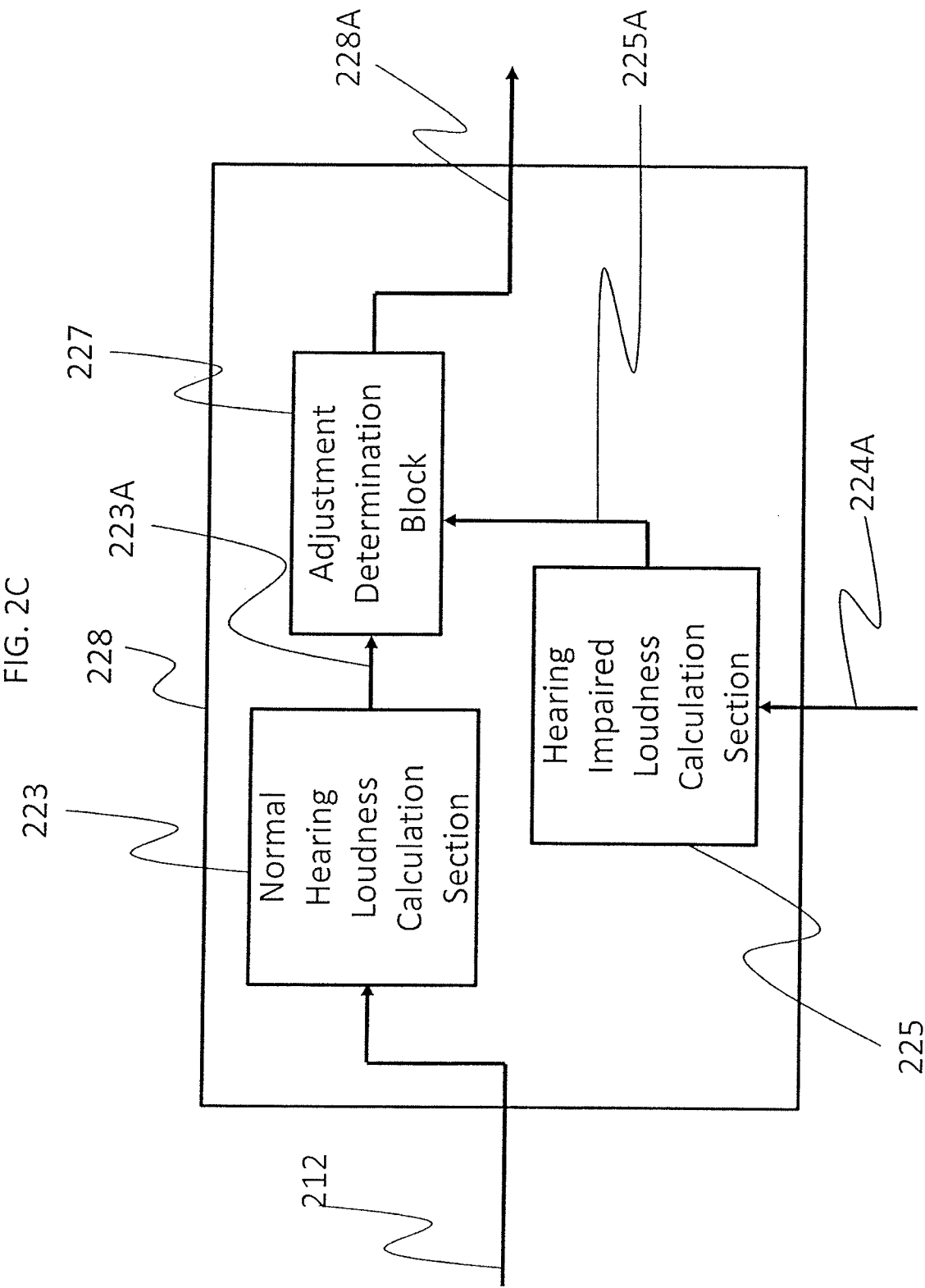
FIG. 2C is a block diagram of a component of the block diagram of FIG. 2B.

Still referring to FIG. 2C, adjustment determination section 228 includes a hearing impaired loudness calculation section 225 that is configured to evaluate embryonic stimulation information signal 224A from the simulator specific sound processor section 224 and determine a loudness (e.g., determines or otherwise calculates a value representative of loudness) that is estimated as being perceived by a hearing-impaired listener (including that which actually would be perceived by a hearing-impaired listener) exposed to output of the hearing prosthesis if the respective stimulation signal generator 230R or 230L was provided with signal 224A. In an exemplary embodiment, this determination is made using a hearing-impaired loudness model as detailed below for the applicable type of stimulation (e.g., an electric stimulation model, an acoustic stimulation model, etc.). As will be detailed below, expansive and/or simplified models can be used, depending on, for example, the available processing power and/or the desired accuracy of the models. It is further noted that the output of section 225 can be such that it is a result of fitting the prosthesis to the recipient. That is, the output of section 225 can be different for different recipients. It can also be the same for different recipients and can be the same for all recipients, depending on the embodiment. It is further noted that the output of section 223 can be such that it is a result of fitting the prosthesis to the recipient.

Accordingly, in an exemplary embodiment, with reference to FIG. 2A, sound processor system 220R is configured to process signal 212R (the input to sound processor system 220R) such that signal 222R (the output of sound processor system 220R) has a magnitude corresponding to that of the signal 212R as modified by a first standard for at least some of the outputs. Also, sound processor system 220L is configured to process signal 212L (the input to sound processor system 220L) such that signal 222L (the output of sound processor system 220L) has a magnitude corresponding to that of the signal 212L as modified by a second standard for at least some of the outputs. In an exemplary embodiment, the first standard is a standard that forces the outputs of sound processor system 220R to have respective magnitudes corresponding to that which would result in the simulation signal generators outputting stimulation according to that would be perceived by a normal hearing listener for the at least some first outputs and the at least some second outputs. The second standard can do the same for sound processor system 220L. All of this can be the opposite as well, in an alternate embodiment (i.e., the second standard is for system 220R and the first standard is for system 220L).

As can be seen, the hearing impaired loudness calculation section 225 outputs a signal 225A which indicates the loudness which would be perceived/estimated to be perceived as noted above. Signals 223A and 225A are provided to adjustment determination block 227, which compares the signals (or data representative of the information contained or otherwise conveyed by the signals) and calculates or otherwise determines the modification that can be made to a magnitude of signal 224A such that a property (e.g., loudness) of the respective evoked hearing percept evoked as a result of the modified signal 222 being provided to the respective stimulation signal generator corresponds to that which is estimated to be that which would be the case for a normal hearing person. Adjustment determination block 227 then outputs the control signal 228A to adjuster 226 to adjust the signal 224A (which is an embryonic signal, as noted above) into signal 222. It is noted that in an alternate embodiment, a completely new signal can be generated based on the signal 228A and the signal 224A. This would result in adjusting the result of the processing of the sound processor system 220.

Figure 2D:
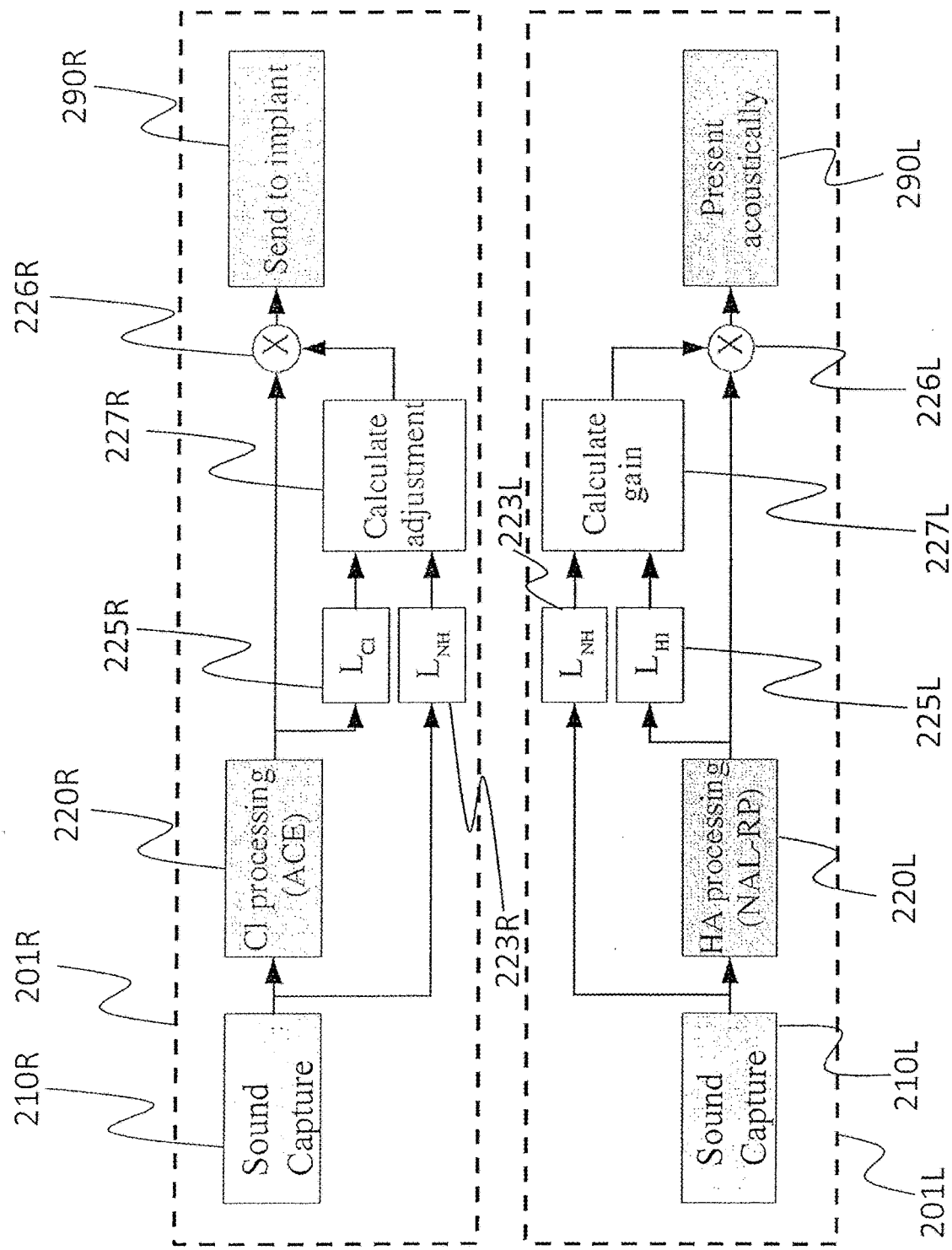
FIG. 2D is a functional diagram of the system of FIG. 2A.

FIG. 2D provides an exemplary functional diagram of the operation of bimodal implant system 200 when subsystem 201R is a cochlear implant and subsystem 201L is an acoustic hearing aid, with reference numbers applied to the functional blocks of FIG. 2D corresponding to the applicable components of FIGS. 2A-2C detailed above, with the additional modifier of "R" and "L" to signify the application of the element in the right or left side. The sound processing strategies are those detailed above (which are exemplary). The functional diagram of FIG. 2D concludes with blocks 290R and 290L. Block 290R corresponds to, by way of example, the transcutaneous transmission of electrical signals to internal coil 136 via the inductive RF channel with respect to the cochlear implant 100 detailed above in FIG. 1. Block 290L corresponds to, by way of example, the output of a speaker of a hearing aid.

It is noted that any and/or all of the components detailed herein and/or variations thereof of the sound processors can correspond to electronic devices configured to implement the functionality detailed herein and/or variations thereof. By way of example only and not by way of limitation, the sound processor system 220R and/or 220L can be microprocessors and/or a series of microprocessors and/or an assembly of microprocessors configured or otherwise arranged to have the functionality herein and/or variations thereof. Alternatively and/or addition to this, the components can be hardware and/or firmware based and/or software-based components. In some embodiments, sum and/or all of these components can be configured to execute the algorithms detailed herein and/or variations thereof and/or other algorithms. Any device, system and/or method that can be utilized to enable or otherwise implement the teachings detailed herein and or variations thereof can be utilized in at least some embodiments.

Figure 2E:
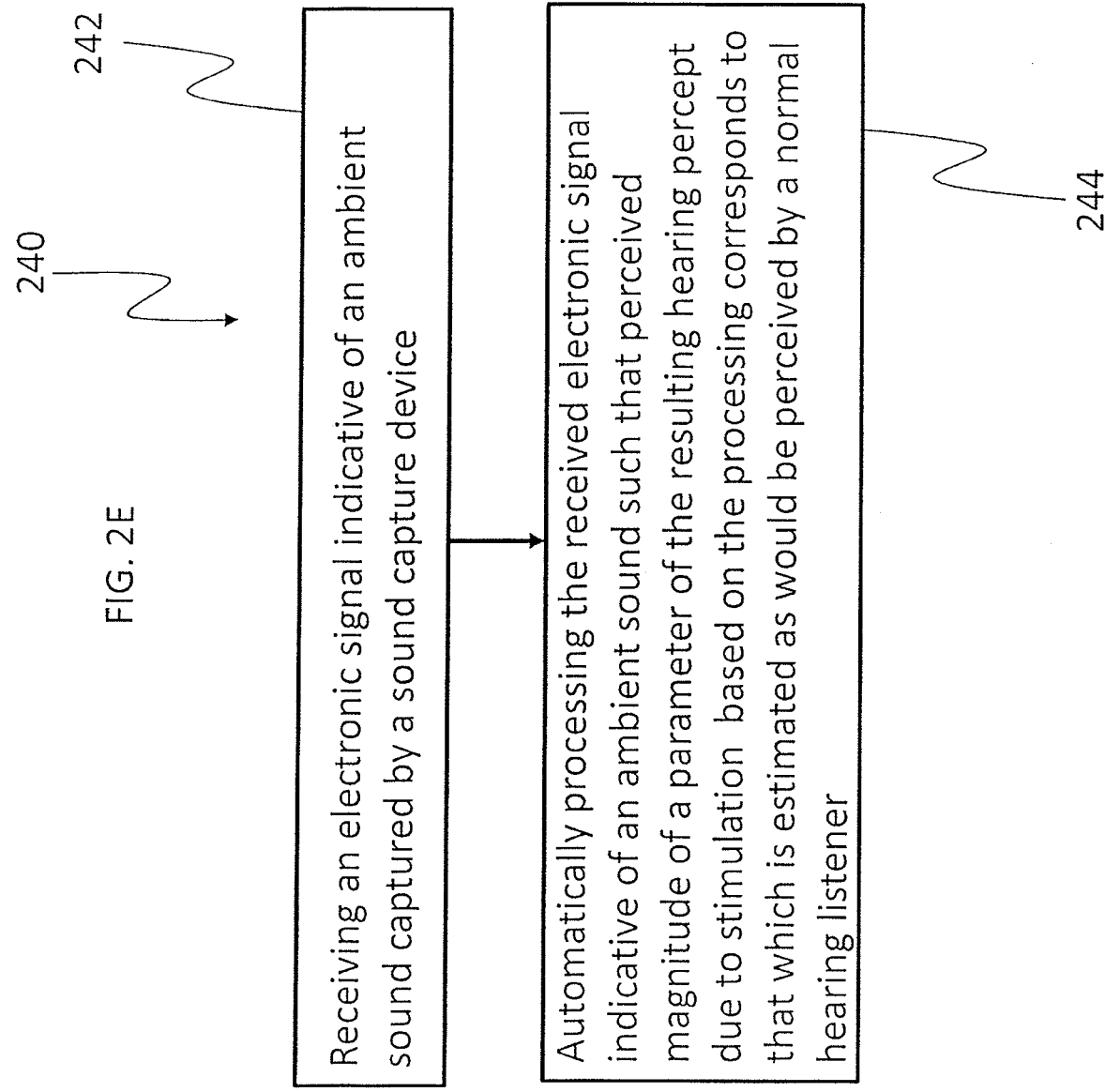
FIG. 2E is a flowchart representing an exemplary algorithm according to an exemplary embodiment.

Along these lines, FIG. 2E depicts an exemplary flowchart representing an exemplary algorithm 240 executed by sound processor systems 200R and 200L. According to this exemplary algorithm, the algorithm includes action 242, which entails receiving an electronic signal (such as electronic signal 212R or 212L) from a microphone or other sound capture device indicative of an ambient sound captured by that sound capture device. Algorithm 240 further includes action 244, which entails automatically processing the received electronic signal indicative of the ambient sound such that the perceived magnitude of a parameter (e.g. loudness) of the resulting hearing percept due to stimulation based on the processing corresponds to that which is estimated as would be perceived by a normal hearing listener.

In some exemplary embodiments, the algorithm of FIG. 2E is utilized in an algorithm for the bimodal implant system 200. Referring now to FIG. 2F, there is presented an example of such an algorithm. More particularly, algorithm 250 includes action 252, which entails capturing an ambient sound utilizing a sound system that includes first and second microphones (i.e. microphones 210R and 210L). As can be seen, algorithm 250 includes actions 254A and 254B, which respectively entail executing algorithm 240. In the embodiment of FIG. 2F, upon the completion of method action 254A, the algorithm 250 goes on to execute method action 256A, which entails automatically stimulating a first tissue type (e.g., a cochlea in the case of a cochlear implant) in a first manner (e.g. electrically in the case of a cochlear implant) with output from the hearing prosthesis system based on the processing of algorithm 240 in method action 254A. Also in the embodiment of FIG. 2F, upon the completion of method action 254B, the algorithm 250 goes on to execute method action 256B, which entails automatically stimulating a second tissue type (e.g., a tympanic membrane in the case of an acoustic hearing aid) in a second manner (e.g. acoustically in the case of an acoustic hearing aid) with output from the hearing prosthesis system based on the processing of algorithm 240 in method action 254B.

It is noted that in the algorithm of FIG. 2F, the method actions 254A and 256A are executed on a temporal basis with method actions 254B and 256B such that the respective evoked hearing percepts are evoked in a temporally desired manner. This is not to say that these method actions must be performed simultaneously—it is the result that can control the temporal nature of the timing of the method actions. Indeed, in an exemplary embodiment, any timing of the execution of the method actions which achieves a desired result can be utilized in at least some embodiments. An example of such a temporally desired manner (result) includes evoking respective hearing percepts such that a perceived directionality of the ambient sound is substantially the same as (which includes the same as) that which would be perceived by normal hearing listener.

With respect to the algorithm 250, in an exemplary embodiment of that algorithm, the automatic stimulation of the first and second tissue types is such that the estimated perceived magnitudes of respective parameters (e.g. loudness) of the resulting hearing percepts due to the stimulation are at least substantially the same/the automatic stimulation of the first and second tissue types is such that the perceived magnitudes of respective parameters (e.g., loudness) are harmonized.

Referring now to FIG. 2G, there is another algorithm, algorithm 260, which is executed by signal processor 220. Additional details of the specific actions of algorithm 260 are detailed below with respect to "SCORE bimodal," which, after its introduction, is sometimes referred to without the modifier "bimodal." However, the following is a brief discussion of this algorithm.

Algorithm 260 entails action 262, which corresponds to action 242 of algorithm 240 detailed above: receiving an electronic signal indicative of an ambient sound captured by sound capture device (e.g. microphone 212L and/or 212R). Algorithm 260 further includes action 264, which is executed by stimulator specific sound processor section 224 with respect to the embodiment of FIG. 2B, which entails automatically processing the received electronic signal and outputting a first signal configured to control a stimulation signal generator (e.g. stimulation signal generator 230L or 230R). This is not to say that the output signal in fact controls a stimulation signal generator, because, as noted above and also as detail below, adjuster 226 adjusts this output signal. After executing method action 264, algorithm 260 includes method action 266, which entails automatically calculating a first value representative of loudness which is estimated as that which would be perceived by hearing-impaired listener stimulated by the stimulation generator based on the output signal. In this regard, method action 266 corresponds to the functionality of the hearing impaired loudness calculation section 225 of FIG. 2C.

Algorithm 260 also includes method action 268, which entails automatically calculating a second value representative of loudness which is estimated as that which would be perceived by normal hearing listener exposed to the ambient sound based on the received electronic signal. This method action corresponds to the functionality of the normal hearing loudness calculation section 223 of FIG. 2C. After executing method actions 266 and 268 (which may or may not be executed simultaneously) algorithm 260 proceeds to method action 269, which entails comparing the first and second values calculated in method actions 266 and 268 respectively and outputting a control signal (corresponding to control signal 228A of FIG. 2C) to adjust the second signal. Method action 269 corresponds to the functionality of adjustment determination block 227 of FIG. 2C.

It is noted that in the algorithm of FIG. 2G, the method actions are executed on a temporal basis with respect to each other such that the respective evoked hearing percepts are evoked in a temporally desired manner. This is not to say that these method actions must be performed simultaneously—it is the result that can control the temporal nature of the timing of the method actions. Indeed, in an exemplary embodiment, any timing of the execution of the method actions which achieves a desired result can be utilized in at least some embodiments.

In some embodiments, at least some of the teachings detailed herein and or variations thereof can be utilized in a hybrid auditory prosthesis system in which two different stimulation devices are fitted to the same ear (e.g., a cochlear implant and an acoustic hearing aid). In an exemplary embodiment, hearing percepts are evoked in the same ear utilizing two different types of stimulation/using two different types of apparatuses that utilize different principles of operation to evoke the hearing percepts. These embodiments are practiced such that the respective processing to obtain the stimulation signals to evoke the respective hearing percepts is performed independently. According to one exemplary embodiment as functionally depicted in FIG. 2H, there is a hybrid system 270 which includes signal processing for acoustic stimulation at block 220A, and signal processing for electric stimulation at block 220CI. Each of these blocks respectively receive an audio signal 212A and 212B which is representative of at least a portion of the ambient sound that originated acoustic pressure/soundwave 103 captured by a sound capture system (not shown) of the hybrid system 270, which can include respective microphones for the respective signal processing blocks. In an exemplary embodiment, the audio signals 212A and 212CI can be pre-processed signals from the microphone system. By way of example, the audio signal 212A can be a signal representing a frequency range lower than that of the audio signal 212CI. Along these lines, in an exemplary embodiment, hybrid system 270 can include a preprocessor that modifies the output of the sound capture system of hybrid system 270 such that the audio signal 212A and audio signal 212CI represent the aforementioned frequency ranges. In an exemplary embodiment, such can be accomplished utilizing a high bandpass filter and/or a low bandpass filter etc. Any device, system or method of preprocessing can be utilized in at least some embodiments such that the teachings detailed herein and/or variations thereof can be practiced.

Still referring to FIG. 2H, signal processing for acoustic stimulation at block 220A, and signal processing for electric stimulation at block 220CI are executed, respectively, according to the teachings detailed herein with respect to a sound processor system 220L and sound processor system 220R detailed above with respect to FIG. 2A, for the cochlear implant/acoustic hearing aid combination, or variations thereof. These blocks are separate blocks, as can be seen, and thus the signal processing is performed independently of the other of the signal processing. The results of the aforementioned signal processing correspond to signals 222A and 222CI, which can, in some embodiments, correspond respectively to signals 222L and 222R detailed above with respect to FIG. 2 A. Stimulation signal generation for acoustic stimulation based on signal 222A occurs at block 230A, and stimulation signal generation for cochlear implant stimulation (electrical stimulation) based on signal 222CI occurs at block 230CI. In an exemplary embodiment, the respective stimulation signal generations are executed, respectively, according to the teachings detailed herein with respect to stimulation signal generator 230R and stimulation signal generator 230L detailed above with respect to FIG. 2A, for the cochlear implant/acoustic hearing aid combination, or variations thereof.

Upon completion of the respective stimulation signal generations, hybrid system 270 outputs signals 232A and 232CI, which respectively correspond to an acoustic stimulation signal (a pressure wave) and an electrical stimulation signal (electrical current) to the tympanic membrane 104 and the cochlea 116, respectively, as can be seen in FIG. 2H.

Is noted that while the hybrid system 270 has been presented in terms of functionality of a cochlear implant and functionality of an acoustic hearing aid combination, other exemplary embodiments, one or both of these functionalities can be replaced with a different functionality. By way of example, a hearing prosthesis having a different principle of operation can be utilized in lieu of an acoustic hearing aid and/or the cochlear implant (e.g., a DACI or a bone conduction device).

Still with respect to the hybrid system 270 of FIG. 2H, in an exemplary embodiment, signal processing for acoustic stimulation and signal processing for electric stimulation respectively include executing the algorithm 240 of FIG. 2E. Still further, in an exemplary embodiment, the signal processing of hybrid system 270 include executing the algorithm 260 of FIG. 2G. That is, in an exemplary embodiment, the signal processing includes estimating or otherwise determining a value representative of loudness which is estimated as that which would be perceived by a normal hearing listener exposed to the ambient sound based on the signals 212A and 212B, respectively, for the respective signal bands represented by those signals. The above embodiments have been described in terms of modifying a signal processed according to a processing strategy for a specific hearing prosthesis such that the magnitude of a property of that signal corresponds to that which is estimated as that which would be associated with normal hearing. In the above embodiments, the modification has been directed towards total loudness (i.e., loudness across all frequency bands). This was the case even with respect to the hybrid system 270 of FIG. 2H, even though the inputs into signal processing for acoustic stimulation and the signal processing for electrical stimulation represented different frequency ranges—algorithm 260 is applied to the entire input 212A and 212B respectively. In an alternate embodiment, the methods detailed herein and or variations thereof (e.g. the algorithm 260) can be applied to sub-frequencies within a frequency range. In an exemplary embodiment, such can have utility with respect to single side deafness.

By way of example, with respect to algorithm 260 there can be an action of filtering the received electronic signal(s), utilizing a filter bank, between actions 262 and 268. This can split the signal into a plurality of frequency bands. Actions 268, 264 and 269 can then be executed independently for each of the frequency bands (or for sets of the frequency bands), and the adjustment is performed for each frequency band (or for each set of the frequency bands). With respect to stimulation by an acoustic hearing aid, the bands are ultimately combined (or recombined). With respect to electrical stimulation, because there can be a filter bank already present, this filter bank can be used and therefore the bands are not recombined (although recombination can be practiced). With respect to single sided deafness, the specific loudness can be estimated for at least part of the spectrum for each filter in a cochlear implant filter bank. This can be done after estimating the cochlear implant loudness for each channel (frequency band), and applying a corresponding adjustment according to the teachings detailed herein and/or variations thereof for each channel.

It is further noted that the teachings detailed herein and/or variations thereof can be applicable to any combination of the hearing prostheses fitted to two ears. For example, some embodiments include a hearing prosthesis system which includes a hybrid system used in one ear, and a contralateral hearing prosthesis in the other ear. Accordingly, an exemplary embodiment can include hybrid system 270 (or a variation thereof) with respect to the embodiment of FIG. 2H fitted to one ear of a recipient, and one of subsystems 201R or 201L (or a variation thereof) with respect to the embodiment of FIG. 2A in the other ear.

Some exemplary embodiments of the bimodal implant system 200 and/or variations thereof and/or other systems or methods or apparatuses detailed herein (e.g., the hybrid system just detailed) and/or variations thereof can be practiced with utilitarian heuristics, some of which will now be described.

According to one exemplary embodiment practiced with utilitarian heuristics, with respect to the sound processor system of FIG. 2B, the output of the stimulator specifics sound processor section 224 is not modified or otherwise adjusted if a normal hearing listener subjected to the sound that produced signal 212 would hear the sound as a relatively soft or otherwise low sound. By way of example only and not by way of limitation, if the normal hearing loudness calculation section 223 of FIG. 2C outputs a result that is below a threshold, the adjustment determination block determines that an adjustment is not to be made and/or the functionality of the adjustment determination block is suspended such that signal 228A is not outputted and/or adjuster 226 goes to a default which permits signal 224A to travel therethrough in an unmodified/unadjusted state. That is, there is no adjustment if the target loudness for normal hearing is below a threshold. The threshold can be predetermined and stored in adjustment determination block 227 and/or at another location (e.g., a memory not shown) such that the adjustment determination block 227 can retrieve the threshold/information indicative of the threshold.

It is noted that loudness is an exemplary property. This embodiment (and the other embodiments detailed herein) can be practiced by comparing a threshold to any magnitude of a property of a signal providing that the teachings detailed herein and/or variations thereof can be practiced.

Such a heuristic can have utilitarian value in that the loudness perceived by the recipient for soft sounds/sound that are not loud is that which would be the case based on the sound processing strategy utilized in the stimulator specifics sound processor section 224, as opposed to a loudness that is adjusted based on the normal hearing model. Thus, the loudness is not unnecessarily increased (or decrease) with respect to sounds that are not of particular interest (e.g., loudness is not modified for speech sounds not directed to the recipient, etc.).

According to another exemplary embodiment practiced with utilitarian heuristics, again with respect to the sound processor system of FIG. 2B, the output of the stimulator specific sound processor section 224 is not modified or otherwise adjusted if a magnitude of a property of the hearing impaired loudness calculation section 225 of FIG. 2C determines or otherwise outputs a result that is below a threshold. By way of example, the property can be loudness (loudness estimated to be perceived by the listener of the unmodified output of the stimulator specific sound processor section 224). Thus, for example, if section 225 of FIG. 2C outputs a result that is below a threshold, the adjustment determination block determines that an adjustment is not made and/or the functionality of the adjustment determination block is suspended such that signal 228A is not outputted and/or adjuster 226 goes to a default which permit signal 224A to travel therethrough in an unmodified/unadjusted state. As with the embodiment detailed above (and as with the embodiments detailed below), the threshold can be predetermined and stored in adjustment determination block 227 and/or at another location (e.g., a memory not shown) such that the adjustment determination block 227 can retrieve the threshold.

It is noted that this embodiment can be practiced alone or with one or more or all of the other embodiments of the heuristics detailed herein and or variations thereof, as is the case with the other embodiments of the heuristics detailed herein and variations thereof.

It is noted that the aforementioned thresholds can be static/absolute thresholds. Conversely, the aforementioned thresholds can be dynamic thresholds. The thresholds can be variable with respect to a property, such as, for example, frequency, etc. Any threshold or type of threshold that can be utilized with the teachings detailed herein and/or variations thereof can be utilized in at least some embodiments.

It is further noted that these thresholds can be set on a recipient specific basis. That is, thresholds for one recipient can be different than that for another recipient, etc. Accordingly, an exemplary embodiment includes a fitting method that includes setting one or more thresholds in a hearing prosthesis that utilizes the teachings herein and/or variations thereof.

At least some of the utilitarian heuristics detailed herein and/or variations thereof can have utility in that the normal/commercially available safeguards of the sound processing strategies associated with the stimulator specific sound processing section 224 for example, are not circumvented by the adjustment based on normal hearing. Along these lines, it is noted that the threshold can be a rate based threshold and/or a threshold the takes into account change with respect to a function. For example, with reference to the embodiments where adjustment is prevented if the target loudness is below a threshold, an embodiment can evaluate the slope of the target loudness over a pertinent period and prevent or limit an adjustment if the slope is above a threshold. By way of example, such an embodiment can have utility in that sudden changes in loudness perceived by the recipient can be avoided or otherwise the likelihood of such is reduced. That is, if the threshold of the slope is set at a sufficiently low value, any change in normal hearing loudness that is abrupt or otherwise sudden can be prevented from being passed on to the recipient. This can have utility in that the normal signal processing safeguards are not circumvented by the adjustment. This can also have utility in that the recipient is provided with effectively a more comfortable experience than that which would be the case in the absence of the utilitarian heuristics.

It is noted that the last embodiment includes the feature of limiting the adjustment as opposed to preventing the adjustment. It is noted that all of the heuristic embodiments detailed herein and variations thereof can be practiced by limiting the adjustment in the alternative and/or in addition to preventing the adjustment.

Corollary to the just detailed embodiment is that if no adjustment is to be applied and/or if the adjustment is limited with respect to that which would otherwise be the case, the system returns itself to a default adjustment at a specific rate, which could be predetermined and/or can be a static or dynamic rate. Such can have utility in that audible clicks or the like can be avoided or otherwise prevented. Further along these lines, maximum adjustment/change between two frames (e.g., two subsequent frames) can be limited to a maximum value and/or the amount of adjustment can be set to a minimum (i.e., any adjustment always results in a minimum adjustment) and/or limited to a maximum adjustment.

All of this said, in an exemplary embodiment, the normal safeguards can be overridden by the adjustments, at least when the adjustments are executed after the standard processing and at least when the standard processing includes the safeguards.

In an exemplary embodiment, there can be an extra safeguard after the adjustment that limits the electric output levels to predetermined C levels (which can correspond to the C levels in the processor, or can be slightly higher and/or lower).

Some features associated with utilitarian signal processing strategies that, in at least some embodiments, are usable with the teachings above will now be described. Below, various teachings are provided with respect to what is referred to by the phrase SCORE bimodal. By way of example only and not by way of limitation, some of the teachings detailed below provide performance data (empirical and/or analytical) associated with SCORE bimodal. This performance data is relative to that which would be the case in the absence of implementing SCORE bimodal, all other things being equal. That is, in an exemplary embodiment, the performance data detailed herein is relative to a situation where, all things being equal, everything would be the same except that SCORE bimodal is not utilized in the detailed device, system, and/or method. By way of example only and not by way of limitation, as is detailed below, the non-shaded blocks of the functional diagram of FIG. 2D correspond to SCORE bimodal implementation into a hearing prosthesis system represented by the shaded blocks. The exemplary data provided below with respect to SCORE bimodal is relative to a hearing prosthesis system corresponding to the functional diagram of FIG. 2D without the non-shaded blocks (i.e., a system according to FIG. 2D but only having the shaded blocks).

In at least some exemplary embodiments, the devices, systems and/or methods detailed herein and/or variations thereof result in the exemplary data provided below, explicitly and/or relative to that which would be the case if the devices, systems, and/or methods detailed herein did not implement the teachings associated with SCORE bimodal. Further along these lines, embodiments include devices, systems, and/or methods that result in the exemplary data provided below, explicitly and or relative to that which would be the case if the devices, systems and/or methods detailed herein did not implement the teachings associated with SCORE bimodal (i.e., a hearing prosthesis system/method of using a system corresponding to the functional diagram of FIG. 2D without the non-shaded blocks). Some embodiments include devices and systems that execute one or more or all of the method actions detailed herein and/or variations thereof. Some embodiments include methods of utilizing, in part and/or in whole, the devices and/or systems detailed herein and/or variations thereof.

The following is described with reference to particular approaches to speech processing. However, the teachings detailed above can be utilized with various different speech processing strategies. Embodiments can have utility in assisting in providing an outcome where the percepts provided to a recipient are improved over that which would otherwise be the case, including a scenario when many stimuli are applied within a short time interval and/or to multiple electrode positions in the case of a cochlear implant. Further to this, in at least some embodiments, at least some of the teachings detailed herein and/or variations thereof can be utilized with existing speech processing schemes either separately or in combination to enhance the operational characteristics of such schemes.

As noted above, bimodal system 200 is a system that provides bimodal stimulation that comprises a cochlear implant (CI) and contralateral hearing aid (HA). In an exemplary embodiment, the HA can have one or more the following utilities: improved speech perception in a noisy background, improved sound quality as compared to that which would be the case in the absence of the HA, and binaural localization cues, also as compared to that which would be the case in the absence of the HA.

At least some exemplary embodiments of the embodiments detailed herein and/or variations thereof negate in part and/or in total the growth of loudness with level associated with these hearing prostheses that is different from normal hearing, and different for the CI and HA between the two. In at least some exemplary embodiments, the phenomenon of interaural loudness differences that vary with stimulation level and with stimulus frequency content or conventional HA/CI fitting can balance one or more stimuli at more than one or two intensities. In an exemplary embodiment, the interaural loudness balance is distorted as compared to traditional methods, and the recipient has increased wearing comfort and there is improved sound source localization and/or less speech in noise as compared to traditional bimodal and/or hybrid systems. By way of example, hybrid and/or bimodal hearing prosthesis systems can have very different growth of loudness with level over a given range of frequencies and/or in the two ears. This can lead to discomfort and/or to false perception of directionality of the origination of a given noise (one ear has a louder percept than the other ear, when in reality the opposite should be the case—the recipient thus might perceive a danger as being in one direction (e.g., on one side) of him or her when the danger is in another direction (e.g., on the other side) of him or her. By implementing the teachings detailed herein, in at least some embodiments, the perception of loudness can be harmonized, thus negating in part or in whole this phenomenon of different growth of loudness. Also, by implementing the teachings detailed herein, in at least some embodiments, the perception of loudness can be harmonized, thus negating in part or in whole the phenomenon of false perception of directionality of the origination of a given noise.

Figure 13A:
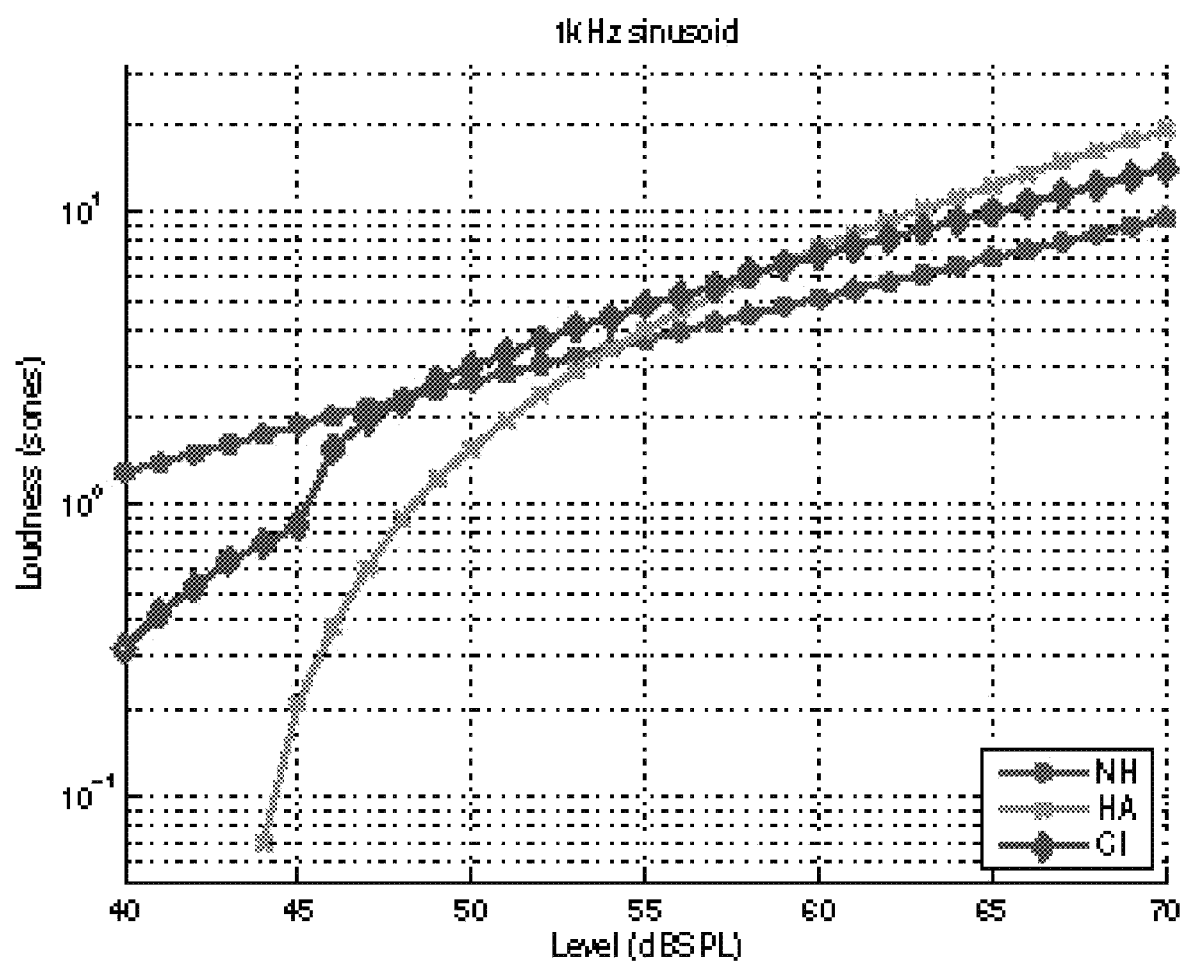
FIG. 13A illustrates loudness growth for a 1-kHz sinusoid.
Figure 13B:
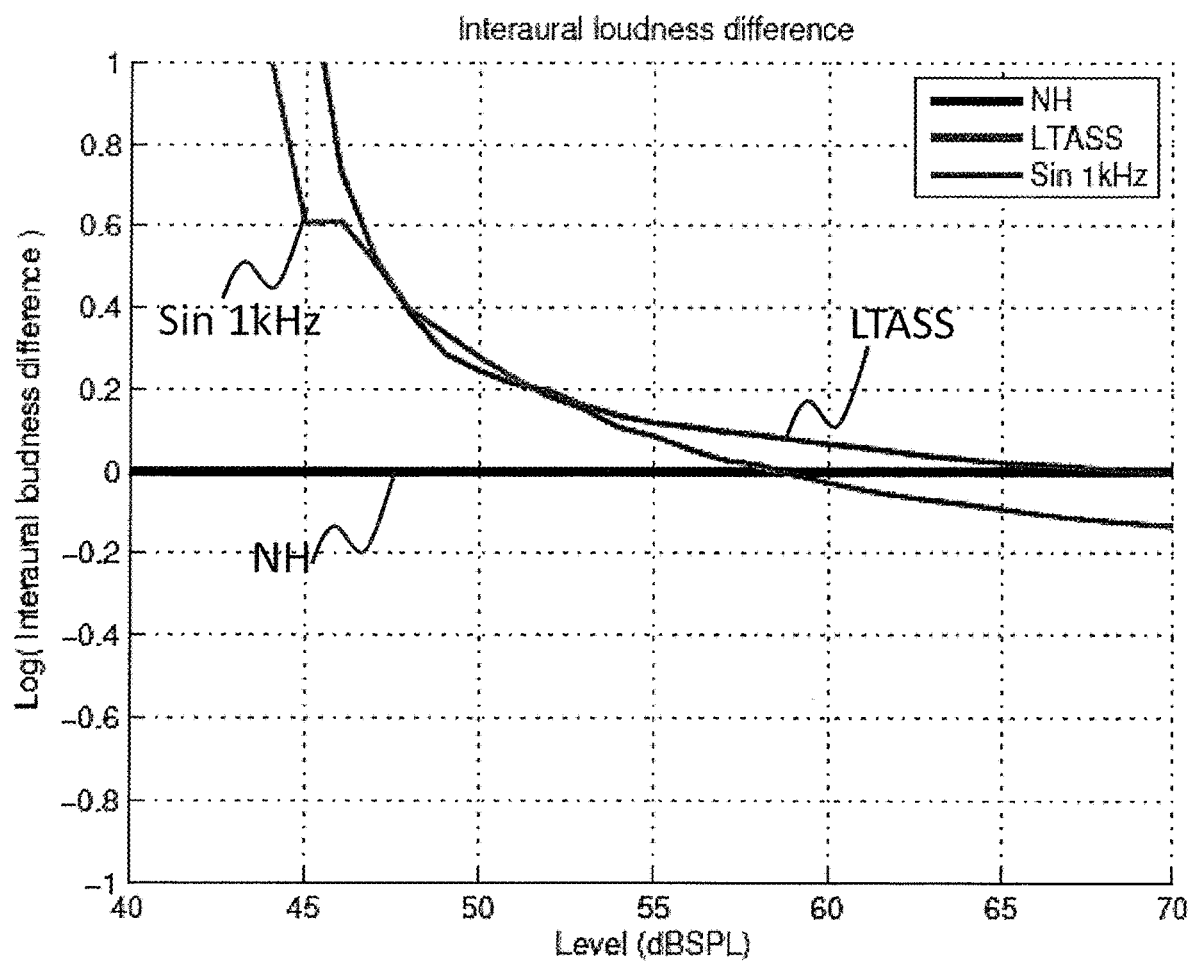
FIG. 13B illustrates the interaural loudness differences.

FIGS. 13A and 13B illustrate by way of example the phenomenon of unequal loudness growth for the two ears for bimodal listeners utilizing bimodal systems that do not include some and/or all of the teachings detailed herein and/or variations thereof. Loudness growth and interaural loudness differences were estimated using loudness models for an exemplary bimodal listener, for a 1-kHz sinusoid and speech weighted noise (LTASS). FIG. 13A illustrates the loudness growth for a 1-kHz sinusoid whereas FIG. 13B illustrates the interaural loudness differences.

Many recently implanted users of a cochlear implant (CI) have residual hearing in the non-implanted ear, which is often stimulated using a hearing aid (HA). This configuration is a classic example of bimodal stimulation. Standard CIs and HAs are used together, which leads to several phenomenon. In many cases, the two devices are fitted at separate places (e.g., the CI clinic and a HA dispenser). Conversely, in an exemplary embodiment, the bimodal and/or hybrid systems according to the teachings detailed herein and or variations thereof are fitted together. By way of example only and not by way of limitation, an exemplary embodiment includes fitting partially and/or completely the subsystem 201R at the same time/during the same session as the fitting of subsystem 201L. Below includes a discussion of the growth of loudness with level for current exemplary clinically fitted bimodal devices, and detail some exemplary embodiments of a bimodal strategy according to an embodiment, which utilitarianly can equalize loudness growth at the two ears using models of loudness perception.

In normal and impaired hearing, an increase in sound pressure level generally leads to an increase in loudness. Similarly for CI stimulation, an increase in current leads to an increase in loudness. The relationship between level and loudness is called the loudness growth function (LGF). LGFs vary with the spectrum of the signal, but also with characteristics of the hearing impairment, and, if CIs or HAs are used, with the signal processing employed in the device. For normal hearing (NH) listeners, LGFs are monotonic and the same for the two ears, leading to consistent changes of perceived interaural level difference with angle of incidence. NH listeners can use this direct relationship to localize sound sources and it can aid in segregation of spatially separated sound sources, which in turn leads to improved perception of speech in noise as compared to non-normal hearing listeners. For hearing impaired (HI) listeners with symmetric hearing losses, LGFs can be similar at the two ears when using the same HAs with similar compression parameters bilaterally. For HI listeners with severely asymmetric hearing losses, of which most bimodal listeners are an extreme example, LGFs sometimes cannot be utilitarianly equalized across the ears with current commercial HAs and CI sound processors. This is reflected in the performance of bimodal listeners on localization tasks. Bimodal listeners can be sensitive to interaural level difference cues, but with commercial devices localization performance is usually inferior as compared to the embodiments according to the teachings detailed herein and/or variations thereof. When looking at differences in the LGF between acoustic stimulation with a hearing impairment and electric stimulation, using models of loudness perception, it is possible that while large parts of the LGFs were similar for a low-frequency noise-band stimulus, there were large differences between acoustic and electric stimulation for a 1-kHz tone. These differences can be related to three main factors: (1) differences in the signal processing in the HA and CI sound processors, (2) suboptimal fitting of the two devices, and (3) the limited frequency range of the residual hearing. Exemplary embodiments can include CIs and HAs that are designed separately without their combined use in mind. Both device types as used in some exemplary embodiments detailed herein and/or variations thereof are designed primarily for optimal speech perception. The HA can contain automatic gain control and fast compression, which change the LGF, and in contrast to prior devices, in at least some exemplary embodiments, the HA is fitted to normalize loudness, i.e., the loudness, or at least the target loudness, evoked by a certain sound is the same as for a NH listener, and/or provides equalized LGFs across ears. The CI sound processor also contains automatic gain control, implemented differently and usually with parameter settings very different from those in the HA. It also contains nonlinear processing such as maxima selection and instantaneous compression designed for optimal speech perception. In an exemplary embodiment, the teachings detailed herein and/or variations thereof enable a LGF less different and/or at least about the same (including the same) as normal and at least about the same as the one in the acoustically stimulated ear, this despite the very different nature of electrical stimulation as compared to acoustic stimulation.

Exemplary embodiments can include fitting of different devices that have different principles of operation (e.g., a CI and an HA) together/at the same time/in the same fitting session despite the fact that the intrinsic operation of the compression systems in the two devices is different, which makes it hard to achieve identical function by tuning parameters, and/or despite the fact that equalizing loudness growth across ears would require extensive loudness balancing across frequencies and levels, which would be very time-consuming, and/or impossible to conduct for a large part of the clinical population. Accordingly, at least some exemplary embodiments detailed herein and/or variation thereof include a method which involves adjusting the level of the cochlear implants stimulus as opposed to or in addition to adjusting the level of acoustic stimulus in order to loudness-balance running speech stimuli across the ears, either at one intensity (for linear hearing aids) or two (for compression hearing aids).

In at least some embodiments, the devices systems and/or methods detailed herein and or variations thereof are applicable for use when there would be differences in loudness growth in the absence of the teachings detailed herein and or variations thereof due to the nature of the residual hearing. By way of example only and not by way of limitation, in some embodiments, the teachings detailed herein and or variations thereof are applies to recipients where there is only residual hearing at low frequencies (e.g., up to 1 or 2 kHz), and a dead region at higher frequencies. This means that without the teachings detailed herein and or variations thereof, broadband sounds will not be balanced if their high-frequency part falls in the dead region and can therefore not be perceived acoustically, whereas utilizing the teachings detailed herein and or variations thereof, broadband sounds can be balanced even if their high-frequency part falls of the dead region and thus cannot be perceived acoustically. For example, with respect to the influence of bandwidth on loudness, for NH listeners, a signal with fixed overall level, loudness increases with increasing bandwidth. However, once the highest frequencies in the signal exceed the edge frequency of a dead region in impaired ears, loudness will decrease. Additionally, signals with only frequency content beyond the edge frequency of the dead region will not elicit any loudness at all. Conversely, application of at least some of it teachings detailed herein and or variations thereof include a sound processing strategy that normalizes loudness perception for electric and acoustic stimulation. The strategy is based on stimulus control to optimize recipient experience (SCORE), and is variously used herein by the acronym "SCORE." It is noted that in an exemplary embodiment, SCORE is implemented according to algorithm 260 with respect to FIG. 2G detailed above.

Some exemplary embodiments of the SCORE strategy comprise add-on processing to current systems. In an exemplary embodiment, there is an exemplary method that entails modifying, replacing and/or otherwise inserting into the processing of current commercial HAs and CI sound processors the score strategy, which, in some embodiments can be accomplished with only minor modifications to other components of these existing systems. SCORE bimodal, according to one or more embodiments, uses loudness models at three different stages to normalize loudness: it estimates (1) the loudness of the signal received by the microphones of the two devices for a NH listener, using a loudness model for NH, such as by way of example only and not by way of limitation, for instance, the loudness model of Moore and Glasberg (1996) and/or model similar thereto and/or variations thereof; (2) the loudness of the signal processed by the HA using a loudness model for HI, such as by way of example only and not by way of limitation, for instance, the model of Moore and Glasberg (1997), and/or model similar thereto and/or variations thereof; and (3) the loudness of the electrical stimulation pattern generated by the CI sound processor. In an exemplary embodiment, "1" corresponds to action 268 of algorithm 260, and "2" and "3" correspond to action 266 of algorithm 260. The overall output level of the signals from the two devices can be, in an exemplary embodiment, the utilitarianly adjusted to match the predicted CI and HI loudness to the predicted NH loudness (corresponding to for example action 269 of algorithm 260). By normalizing loudness, the LGFs at the two sides become at least similar (including the same), the HA is fitted as a result, and broadband perceived inter-aural level cues are made more reliable as compared to that which would be the case in the absence of the SCORE bimodal strategy. In an exemplary embodiment, if normal loudness is not considered a desired target (e.g., another target is identified as having utilitarian value), variations of the SCORE bimodal strategy can be transformed to any desired loudness function.

It is noted that the models detailed herein are exemplary. In alternate embodiments, variations of these models or other models can be utilized. In some embodiments, any model that can enable the teachings detailed herein and/or variations thereof can be utilized in at least some embodiments.

The following corresponds to details regarding prototypes of the SCORE bimodal strategy that have been evaluated. Accordingly, exemplary embodiments include devices, systems and/or methods corresponding to the teachings detailed herein and/or variations thereof that have one or more or all of the features of the prototypes and/or result in one or more or all of the functionalities of the prototypes.

It is further noted that exemplary embodiments include devices, systems and/or methods corresponding to the teachings detailed herein and/or variations thereof that have one or more or all of the features of the prototypes detailed in U.S. Provisional Patent Application No. 61/680,640, entitled "Loudness Normalization Strategy for Combined Cochlear Implant and Acoustic Stimulation," filed on Aug. 7, 2012, and/or result in one or more or all of the functionalities of the prototypes detailed in that provisional patent application.

A prototype of the SCORE bimodal strategy was evaluated for functionality by having six bimodal listeners adjust the level of stimuli of different bandwidths so they sounded equally loud. In a first set of experiments, the applicants validated the acoustic and electric loudness models separately by performing monaural loudness balancing and comparing the results to model predictions. In a second set of experiments, an assessment was made to gauge if SCORE bimodal improved binaural loudness balance by performing binaural loudness balancing experiments, both for the standard clinically used processing (ACE and a linear HA fitted according to the NAL-RP rule), and with application of the SCORE bimodal processing. The existing clinical fitting for all subjects was utilized as a starting point, and the time spent fitting the loudness models was minimized as compared to that which might have otherwise been the case, as to reflect results that would be obtained in a typical clinical setting.

Two signal processing schemes were utilized in the prototype evaluations. The first one, termed ACE bimodal, corresponded to the standard clinical Advanced Combination Encoder (ACE) processing combined with linear HA processing, fitted according to the NAL-RP rule as disclosed by Byrne et al. (1990). The ACE strategy is implemented in a variety of commercial sound processors utilized with cochlear implants. The HA is simulated according to an exemplary embodiment by filtering the acoustic signal in Matlab according to the desired frequency response. The second scheme, termed SCORE bimodal, consisted of ACE bimodal plus extra loudness model-based processing. Referring to the diagram of FIG. 2D, the existing clinical standard ACE bimodal processing is indicated by the shaded blocks. The SCORE bimodal according to at least some embodiments can be utilized as an add-on processing to any sound processing strategy, e.g. to ACE. Accordingly, in an exemplary embodiment, there is an exemplary method that corresponds to obtaining an existing sound processing strategy and adding or on to that sound processing strategy the teachings detailed herein and/or variations thereof. In addition, the latter can be based on loudness model based processing, using models of loudness perception for normal and impaired hearing, and for electric stimulation. This it can use models of loudness perception to estimate, on the one hand, the loudness experienced by a normal-hearing listener when listening to signals received by the microphones at each ear ($L_{NH}$/223R/223L in FIG. 2D), and, on the other hand, the loudness experienced by a hearing-impaired listener when listening to the signal at the output of the hearing aid ($L_{HI}$)/225L, and of a CI listener when listening to the signal at the output of the sound processor ($L_{CI}$)/225R. The overall levels of the acoustic and electric stimulus were adjusted by SCORE bimodal such that the estimated (target) loudness at the output of both devices was the same as the normal-hearing loudness at the input. For the estimate of normal-hearing loudness at the microphone and impaired hearing loudness at the HA output, the loudness model described by Moore (1997) and/or variation thereof can be used for instance, and its parameters can be set based on the unaided audiogram of each listener. Thus the shaded blocks indicate the existing clinical processing that is commercially available, and white blocks indicate the add-on SCORE bimodal processing according to at least some exemplary embodiments. $L_{NH}$, $L_{HP}$ and $L_{CI}$ indicate respectively loudness models for normal hearing, impaired hearing and cochlear implant (electrical) stimulation. Adjustments can be calculated and applied for each frame of 6.9 ms.

As can be seen from the above, various models and/or rules are referred to that can utilize to implement the teachings detailed herein and/or variations thereof. It is noted that while some embodiments utilize these models and/or rules, other embodiments can utilize alternate models and/or rules. In some embodiments any model that corresponds to the aforementioned models with respect to result can be utilized in at least some embodiments. In this regard, any device, system and/or method that can be utilized to estimate or otherwise calculate loudness which would be perceived by normal hearing listener exposed to the ambient sound that generated the signals provided to the processing can be utilized in at least some embodiments. Further in this regard, any device system and/or method that can be utilized to estimate her otherwise calculates loudness which would be perceived by a hearing-impaired listener stimulated by the stimulation generator based on the generated signals can be utilized in at least some embodiments.

With respect to the prototype that was experimentally utilized, binaural balancing was performed in signal processing conditions ACE and SCORE bimodal and a significant improvement in binaural balance was found with application of SCORE bimodal.

As noted above, such as with respect to method actions 268 with respect to algorithm 260, some embodiments estimate the loudness of a signal at microphone level using a loudness model for normal hearing. Further, according to at least some embodiments, as noted above, such as with respect to method actions 266 with respect to algorithm 260, in at least some embodiments, there is the action of estimating the respective loudness after CI and HA processing using a loudness model for electric stimulation or impaired hearing, and utilizing these values to calculate a broadband level adjustment for the signal to normalize the loudness perceived by the recipient.

Below, some exemplary embodiments of the utilization of the ACE and SCORE strategies are described in more detail. It is noted that for ease of reading, the suffix "bimodal" for ACE and SCORE is not utilized in all instances. Although it is noted that the teachings below are applicable to bimodal systems and/or hybrid systems and/or any of the systems detailed herein and or variations thereof even if such is not specifically identified.

With respect to the exemplary prototypes, all processing was performed on frames of samples with an overall duration of 6.9 ms, at a sample rate of 16 kHz. Each frame was processed by each of the signal processing blocks in FIG. 2D.

In an exemplary embodiment, the sound processing strategy utilized in block 220R of FIG. 2D/element 224 of signal processing system 220 of FIG. 2B when used in a cochlear implant correspond to a system of converting an acoustic signal into a pattern of electrical pulses. In an exemplary embodiment, the operation of SCORE (e.g., blocks 223R/227R of FIG. 2D) does not depend on the way in which this is done. The ACE strategy was selected for used in at least some embodiments because it is the one the present subjects were familiar with, and it is used in a variety of commercial sound processors for CI recipients. Other sound processing strategies could be used. The implementation of the ACE strategy was provided in the form of the Nucleus Matlab Toolbox version 4.31. When a CI using the ACE strategy is fitted to a recipient, threshold (T) and comfortable (C) levels are determined for each electrode using pulse trains at the channel stimulation rate (typically 900 pps). These and other parameters which can be relevant to the fitting are stored in a MAP. The current level of a pulse is expressed in current units (CU). The current level of each pulse always lies between the T and C levels, and is determined based on channel magnitudes according to $CL=M*(C-T)+T$, with CL the number of current units (CU), and M the magnitude between 0 and 1. The magnitude in each channel is preferably obtained by transforming the level in each channel of the filter bank after envelope detection by an instantaneous compression function. The difference between C and T levels will be called the dynamic range, and can be different for each individual electrode. The microphone response of the Freedom sound processor was measured using an artificial head and applied to the stimuli before the ACE processing.

It is noted that while various embodiments detailed herein refer to measuring and measurement, alternate embodiments include calculating, estimating, looking-up, and/or extrapolating instead of and/or in addition to measuring, and visa-versa for each of these actions (e.g., instead of estimating, there can be extrapolating, measuring; instead of extrapolating, there can be measuring, estimating, etc.) Any action that will enable the teachings detailed herein and/or variations thereof to be practice can be utilized in some embodiments.

A linear HA was simulated using a 512-coefficient finite impulse response filter, designed for a sampling rate of 16 kHz. The desired aided thresholds were calculated from the unaided audiogram according to the NAL-RP rule. Hearing thresholds were measured using the experimental computer and insert earphones, and the finite impulse response filter was designed to produce the required aided thresholds. The result was verified by measuring aided thresholds using the simulated HA and the insert earphones.

A loudness model used in embodiments of the present invention are briefly summarized below. The loudness as perceived by a NH listener was calculated using the loudness model described by Moore and Glasberg (1997), but replacing the middle-ear transfer function by the one proposed by Moore and Glasberg (2004). Thus, embodiments can utilize a model constructed based on a statistical sampling of a populace. It is noted that alternate embodiments can utilize a model that is at least in part based on a statistical sampling of a populace. Accordingly, with respect to the embodiment of FIG. 2A, the first and second sub-systems 201R and 201L are configured to harmonize perception of magnitude of the parameter of the respective evoked hearing percepts based on a model constructed at least in part based on a statistical sampling of a populace.

For each time frame the model calculates the short-term spectrum, filters it by the middle-ear transfer function, calculates the excitation pattern, transforms it to specific loudness, and sums the specific loudness across frequencies to obtain the total loudness in sones. While updated versions of this loudness model exist, the older version was used in the prototype testing because of its lower computational complexity, which makes it feasible to implement in current CI sound processors and HAs, and the lower number of parameters to be considered. Moreover, differences between the older and newer version of this model are largest at levels near threshold, which is less important for the current application.

Similarly, the loudness as perceived through the subject's hearing-impaired ear was estimated using the loudness model described by Moore and Glasberg (1997). While this model uses a large number of parameters, it can be fitted based solely on the unaided audiogram, using default values for all other parameters. While potentially improved performance could be achieved by individually measuring all other parameters in psychophysical experiments, this would not be feasible in a clinical context because of the time requirements.

In the "calculate gain" block (227L) as illustrated in FIG. 2D, the target (NH) loudness was available (LNH), as well as the loudness perceived by the HI listener of the signal processed through the linear HA (LHI). A gain value was calculated for each frame such that the loudness of the amplified/attenuated acoustic signal would be equal to the target loudness. The output of 227L is provided to adjuster 226R to adjust the signal from block 220L. A formula is used, whereby the total loudness was modified instead of the specific loudness. The detailed algorithm is described in below.

The acoustic adjustment to equalize the total loudness of a frame to a target loudness was calculated as follows. The symbols used correspond to those used by Launer and Moore (2003) and Moore and Glasberg (1997). Most values are calculated for a set of frequency bins f. Let $L_T$ the target loudness, in sones, $E_{HI}(f)$ the HI excitation level, for each frequency bin f, in linear units, $A_{IHC}(f)$ the attenuation factor due to inner hair cell loss, $E_{THRQ}(f)$ the HI hearing threshold, in linear units, a and C: constants of the loudness model, G the current gain relative to NAL-RP, in linear units, initially set to 1, whereby G is calculated iteratively as follows:

Let $AT$ be the set of values of $f$ for which $G\, E_{HI}(f)/A_{IHC}(f) > E_{THRQ}(f)$ Calculate G as $$G = [[(L_T/C) + \Sigma f^{aT}(E_{THRQ}(f))]/[\Sigma f^{aT}(E_{HI}(f)/A_{IHC}(f)^a]]^{1/\alpha}$$

Calculate the resulting HI total loudness after application of G. If total new total loudness is more than 5% off target, repeat steps above. Note that to save computation time the HI excitation pattern is preferably not calculated again for every iteration. This is an approximation, but should not have a large effect for G values in a reasonable range.

Figure 3:
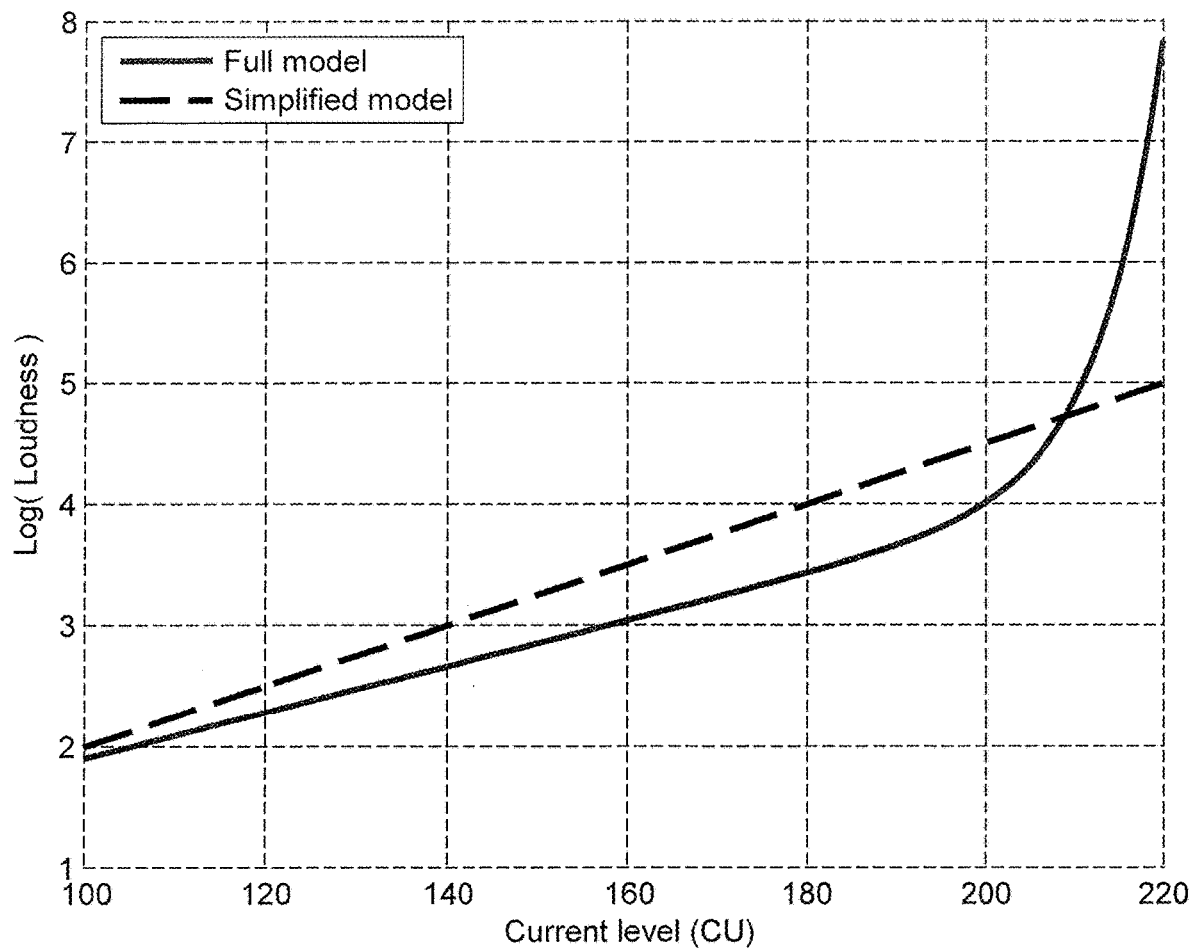
FIG. 3 illustrates an example LGF for a single pulse.

To estimate the loudness of the electrical stimulation pattern generated by ACE, a simplified version of the model developed was used. In this model, the current level of each pulse is converted to a loudness contribution using an electrode-specific LGF. Then all loudness contributions within a time frame are added. In the model, LGFs are assumed to comprise a combination of a linear and exponential part of the form $\log(L) = a*CL + 0:03*b*e^{(CL-c0)/b} + k$, with L the loudness contribution of a pulse, CL the current level, a the slope of the linear part, b determining the shape of the exponential part, $c_0$ the knee point where the linear part changes into the exponential part, and k a scaling factor. Thus for each electrical pulse a loudness contribution is calculated over a certain period of time. An example LGF is shown in FIG. 3, for a=0.019; $c_0$=200; b=0.21; and k=0. The slope of the loudness growth, a, is determined by way of example only and not by way of limitation in a monaural loudness balancing experiment between stimuli of different bandwidths, is usually about 0.019, and $c_0$ generally corresponds to the C level of a 500 pps pulse train. In FIG. 3 the full line was plotted with a=0.019; $c_0$=200; b=0.21, and k=0. The dashed line was plotted according to the simplified model with a=0.025. Determining the full LGF for one electrode might not necessarily be feasible in a clinical setting, let alone for each electrode. It was assumed that LGFs had the same shape on all electrodes and that operation was mainly in the linear region, and thus simplified the LGF to $\log(L) = a*CL + k$. As the current required for a certain loudness percept decreases with increasing stimulation rate, and given that clinical strategies usually operate at higher rates than 500 pps (usually at 900 pps), it is expected that this assumption will hold for most subjects. The slope a was determined in a simple loudness balancing task using broadband signals (see below), which is feasible in a clinical setting, and the scaling factor k was used to obtain loudness values that were similar to the units (sones) provided by the acoustical model.

In the "calculate adjustment" block of FIG. 2D (227R), the target (NH) loudness is available ($L_{NH}$), as well as the loudness of the signal processed through ACE (LCI). The output of 227R is provided to adjuster 226R to adjust the signal from block 220R. The current-level adjustment of the electric signal A is calculated in an exemplary embodiment such that the loudness of the adjusted electric signal is equal to the target loudness: $A = \log(L_{NH}/L_{EL})/\alpha$, with $L_{NH}$ the loudness estimate of the normal-hearing loudness model and $L_{EL}$ the loudness estimate of the electric loudness model, and A the adjustment in fraction of the dynamic range. A is expressed in terms of percentage of the dynamic range (% DR) for each electrode. During fitting of the CI sound processor, for each electrode the just-audible threshold (T) and comfortable loudness (C) are determined with a pulse train of usually 900 pps. In the final stages of ACE processing, filtered acoustic signals with magnitudes between 0 and 1 are mapped between the T and C levels for each electrode. The dynamic range is the difference between C and T level for each electrode. In an exemplary embodiment of SCORE bimodal, electrode adjustments are expressed as a fraction of the dynamic range; e.g. an adjustment of 0.1 would mean that for each electrode (C-T)*0.1 current units are added to each pulse.

For example, if the dynamic ranges for electrodes 5 and 10 were respectively 20 CU and 30 CU, and an adjustment of A=10% DR was utilitarian, the current level of a pulse destined for these electrodes would be increased by 2 and 3 CU. Modified levels in the evaluation of the prototype were always limited to the C level for each electrode, although in some embodiments this might not necessarily be the case.

The reference k only has effect on $L_{EL}$ so the overall effect of k is to add a fixed value to each adjustment calculated. For the speech perception experiment described below, k was determined in a preliminary loudness balancing experiment.

Adjustments in dB (for the acoustic signal) and in fraction of the dynamic range (for the electric signal) were calculated for each frame of 6.9 ms duration. Adjustments were smoothed using a set of heuristics and automatic-gain-control-like processing with attack and release times of 5 ms and 50 ms respectively. Note that no automatic gain control or other compression was used. As SCORE bimodal operated on the broadband acoustic signal and affected all electric channels equally, it did not affect the spectral characteristics of the signals. While the operation of SCORE depended very much on individual characteristics of hearing loss and the input signals used, generally its application had the following effects: at the electric side SCORE counteracted loudness artifacts introduced by maxima selection, and at the acoustic side SCORE counteracted the effect of reduced audibility of high-frequency sounds due to a lack of high frequency residual hearing. This often had the effect that soft phonemes were amplified.

The "Calculate gain" and "Calculate adjustment" blocks yield gains and adjustments to be applied to a specific frame. It was assumed that by normalizing the instantaneous loudness in this way, it would also be utilitarian to normalize long-term loudness. To avoid audible artifacts in the signal, the gains (in dB) and adjustments (in % DR) were smoothed according to a set of heuristics and automatic-gain-control-like processing with attack and release times of 5 ms and 50 ms respectively. The heuristics included a rule to not apply any adjustment if the loudness estimated by any of the models (NH, HI, and CI) was below a threshold value, a rule to limit the maximal change in adjustment between subsequent frames, and a rule to limit the maximal adjustment. By using the same type of smoothing for the two devices, in some embodiments, the LGFs can be kept largely the same.

Accordingly, in an exemplary embodiment, with reference to FIG. 2A, signal 212R is processed based on a magnitude of that signal as modified by a first normalization standard, and signal 212L is processed based on a magnitude of that signal as modified by a second normalization standard. It is noted that in the case where each ear is stimulated utilizing the same principle of operation, in an exemplary embodiment, still with reference to FIG. 2A, signal 212R is processed based on a magnitude of that signal as modified by a first normalization standard, and signal 212L is processed based on a magnitude of that signal as modified by the first normalization standard.

In view of the above, according to an exemplary embodiment, there is a method of fitting a bimodal prosthesis including a cochlear implant and an acoustic hearing aid that includes an action of at least one of setting or adjusting a first parameter of the cochlear implant and an action of at least one of setting or adjusting a second parameter of the acoustic hearing aid such that the automatic processing of the first and second electronic signals results in processing the signals such that at least the estimated perceived magnitudes of respective parameters of resulting hearing percepts due to the stimulation are to be at least substantially the same. Still further, an exemplary method of fitting entails fitting a bimodal prosthesis including the action of setting a reference stimulus to a comfortable level of a recipient of the cochlear implant, performing a recipient-specific cochlear implant loudness balancing task using stimuli of different bandwidths, and determining a recipient-specific slope of a loudness growth of the cochlear implant based on the loudness balancing task. Also, in an exemplary embodiment, there is an exemplary method of fitting that entails fitting a bimodal prosthesis including the action of setting a reference stimulus to a comfortable level of a recipient of the cochlear implant, performing a recipient-specific cochlear implant loudness balancing task using stimuli of different bandwidths, and determining a recipient-specific slope of a loudness growth function used in a loudness model that is used to estimate loudness evoked by stimulation of the cochlear implant based on the loudness balancing task.

Also, an exemplary embodiment includes the method of fitting detailed herein wherein the automatic processing of the first and second electronic signals entails processing the signals based on the recipient-specific slope of the loudness growth function used in the loudness model that is used to estimate loudness evoked by stimulation by the cochlear implant based on the loudness balancing task such that at least estimated perceived magnitudes of respective parameters of resulting hearing percepts due to the stimulation are to be at least substantially the same.

Figure 4:
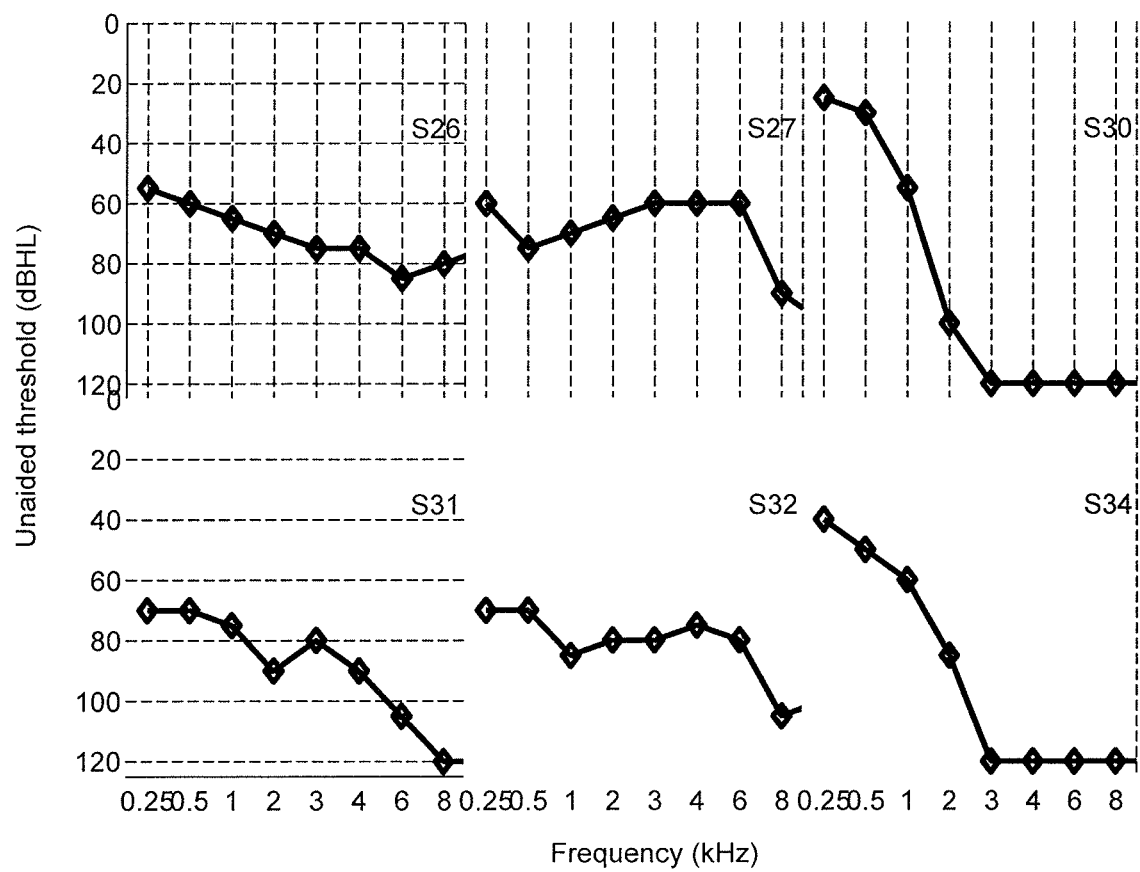
FIG. 4 illustrates pure tone unaided audiograms of a non-implanted ear.

Six subjects were recruited who used a CI in one ear and a HA in the other ear on a daily basis. The pure-tone unaided audiograms of the non-implanted ear for each subject are shown in FIG. 4. Relevant subject information is listed in Table 1. Table 1 comprises for each subject, the following information: "Age" which is in years at the time of testing, "CI use" is the number of months of implant use at the time of testing, "CI side" is left (L) or right (R), the HA was on the other side, and a and k are the parameter values used for the electrical loudness model.

TABLE 1

| Subject | Age (y) | CI use (months) | CI side | Aetiology | a | k |
|---|---|---|---|---|---|---|
| S26 | 75 | 17 | R | Unknown | 0.025 | −4.93 |
| S27 | 78 | 25 | L | Unknown | 0.010 | −2.37 |

TABLE 1-continued

| Subject | Age (y) | CI use (months) | CI side | Aetiology | a | k |
|---|---|---|---|---|---|---|
| S30 | 60 | 28 | R | Unknown | 0.021 | −4.25 |
| S31 | 62 | 17 | R | Unknown | 0.034 | −6.67 |
| S32 | 54 | 84 | R | Meniers | 0.017 | −3.57 |
| S34 | 53 | 28 | R | Unknown | 0.030 | −6.16 |

Four harmonic complexes of increasing bandwidth with $F_0$=200 Hz and 2, 4, 6, or 8 equal-amplitude harmonics, labeled in terms of the frequency of their highest harmonic (S400, S600, S800, S1200) were used as stimuli. These were set to equal loudness for a normal-hearing listener (8 or 16 sones) and were processed by ACE.

Figure 5A:
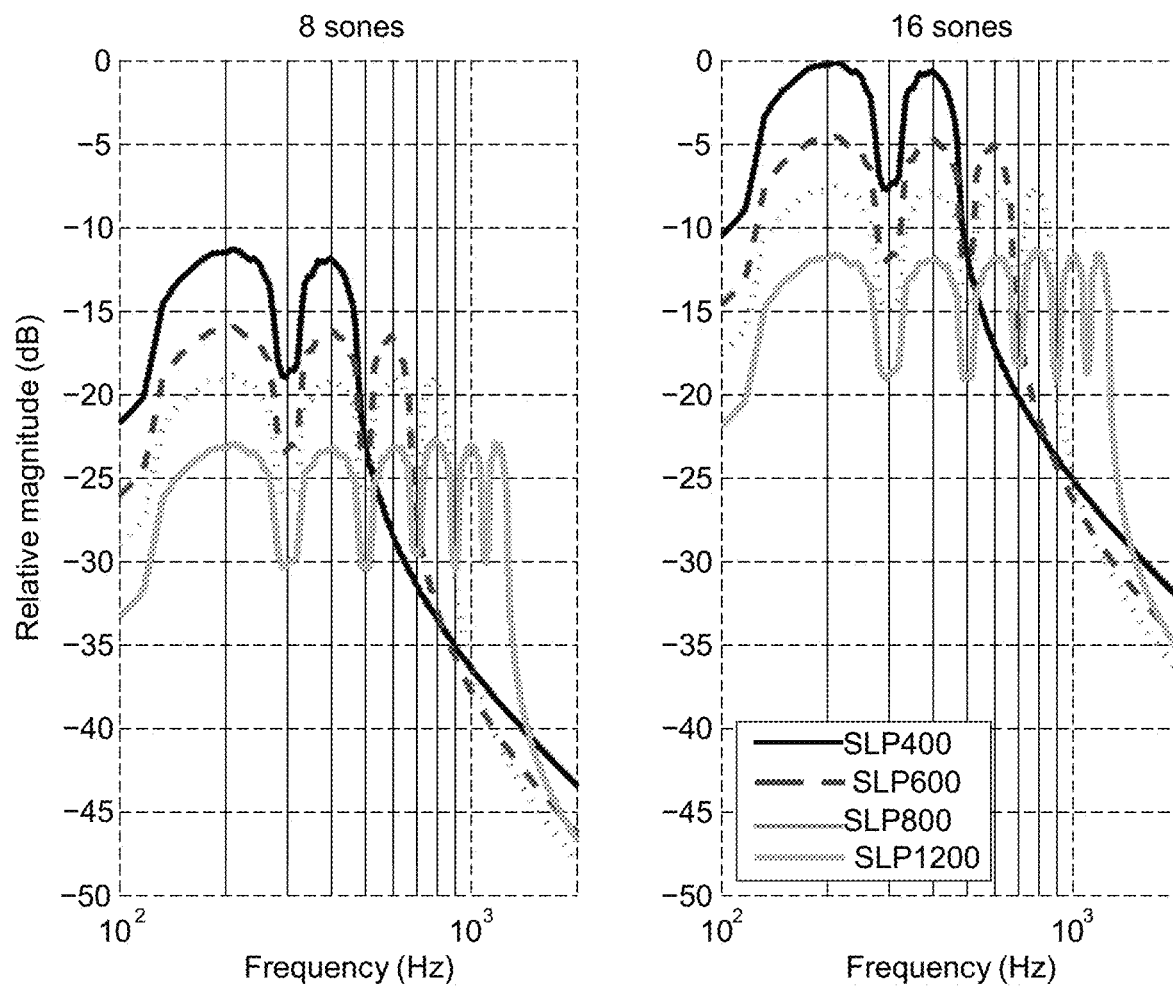
FIG. 5A illustrates spectra of the acoustic stimuli at the input of the CI and HA processing, whereby the acoustic stimuli were set at equal NH loudness.
Figure 5B:
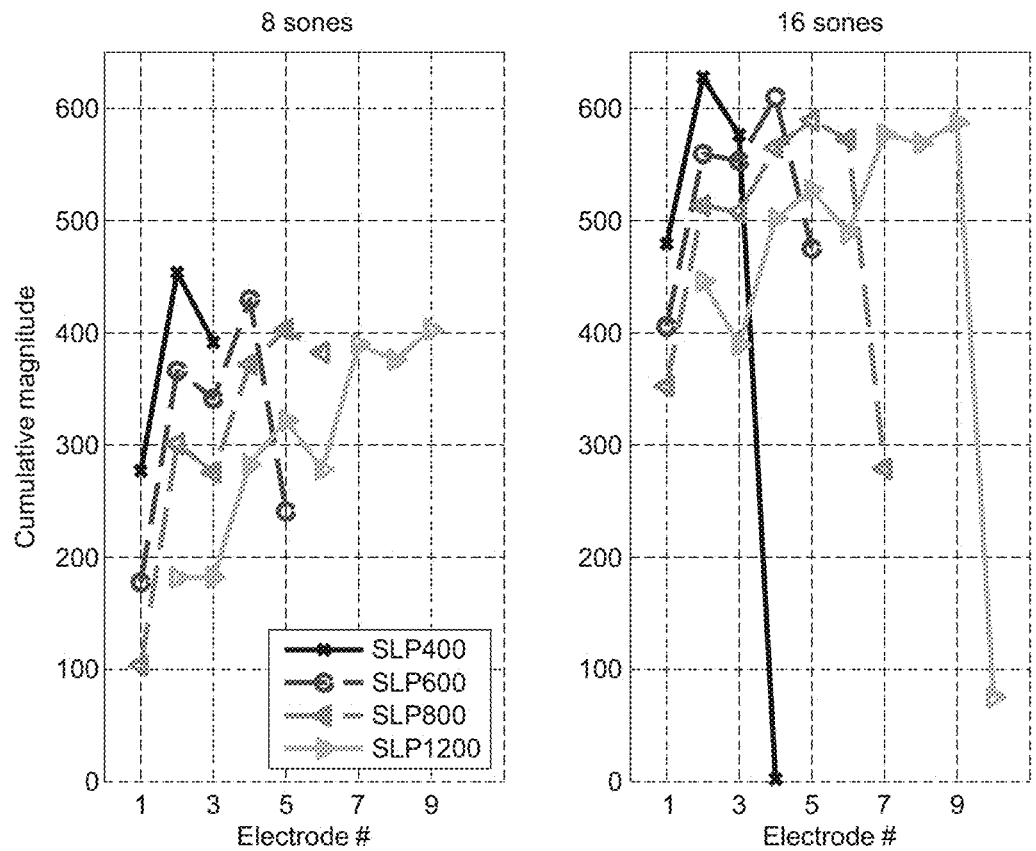
FIG. 5B illustrates cumulative magnitudes of the four different stimuli for a loudness of 8 or 16 sones; whereby electrodes are numbered from apex to base and the cumulative magnitude is the sum of all magnitudes on a single electrode during one second.

More specifically, the stimuli were harmonic complexes with a fundamental frequency of 200 Hz and a varying number of equal amplitude harmonics. In the following, they are labeled in terms of the frequency of their highest harmonic: S400, S600, S800, and S1200 consisted respectively of 2, 3, 4, and 6 harmonics. The levels of the four stimuli were set to produce equal loudness for a NH listener, using the acoustic loudness model described above. To investigate overall level effects experimentally, the loudness of each stimulus was set respectively to 8 and 16 sones. All loudnesses are expressed in terms of binaural stimulation, assuming that switching from monaural to binaural stimulation results in a doubling in loudness. This means that 8 sones corresponded to a fairly soft level, and 16 sones to a comfortable level, similar to that of conversational speech. The resulting spectra are shown in FIG. 5A. All stimuli had a duration of 1 s and had 50-ms sinusoidal ramps to avoid audible clicks at the onset and offset. These eight stimuli were processed through ACE. This resulted in activation of a different number of electrodes for each stimulus at a certain NH equivalent loudness. FIG. 5B illustrates the distribution of current across electrodes. In one of the last stages of ACE processing, magnitudes between 0 and 1 are converted to current levels between T and C level. A magnitude of 0 is mapped to the T level and a magnitude of 1 is mapped to the C level. The cumulative magnitude shown in FIG. 5B is the sum of all magnitudes on an electrode during one second. This type of plot can be compared to the spectrum of an acoustic signal. It is clear that with increasing maximal stimulus frequency, the number of activated electrodes increases, and that the distribution of current across electrodes is not flat. Also, the cumulative magnitude is higher for the 16-sone stimuli than for the 8-sone ones.

Below is an example of acoustic balancing between S1200 and S400:

Reference S1200, comparison S400. Start level +6 dB adjustment of the comparison stimulus. Example result of adaptive run (average of last 6 reversals): +2 dB adjustment.

Reference S1200, comparison S400. Start level −4 dB adjustment. Result: +1.5 dB.

Reference S400 (adjusted by (2+1:5)/2=1:75 dB), comparison S1200. Start level +6 dB adjustment. Result: −1 dB.

Reference S400 (adjusted by 1.75 dB), comparison S1200. Start level −7 dB adjustment. Result: −3 dB.

The final result is calculated as (2+1.5+(1.75−(−1))+(1.75 (−3)))=4=2.75 dB adjustment.

To assess if SCORE improved binaural balance, binaural balancing experiments for the standard ACE processing and for SCORE were conducted, and compared the results. In contrast to the monaural experiments, the electric and acoustic stimuli were presented simultaneously. The stimulus prior to processing was the same for the two ears, and therefore should ideally yield a balanced percept, like for a NH listener. The acoustic gain adjustment for a balanced percept was measured and compared these values between the ACE and SCORE conditions.

In the following section, monaural balancing results are compared to model predictions. In the binaural balancing experiment, the SCORE processing was applied, which included setting some model parameter values. While the acoustic loudness model for HI listeners only utilized the subject's audiogram, for the electric model two parameters to be set: the slope of the loudness growth function a and k. Functions a and k were determined numerically, assuming that stimulus S1200 had a loudness of 16 sones and minimizing the RMS error between the psychophysical monaural balancing results at 16 sones and the model predictions. Note that 16 sones corresponds to a comfortable loudness, which was the target of the initial volume setting of the sound processor. The value k mainly serves to set the units of the electric loudness model to sones, thus making the results comparable to those of the acoustic loudness model. Value a is a scaling factor of the adjustment. If the clinical fitting were ideal, i.e., T and C levels corresponded to exactly the same loudness in all subjects, and all current levels fell within the linear region of the LGF, a would be the same for all subjects. The k and a values that were used for each subject are shown in Table 1.

Figure 6:
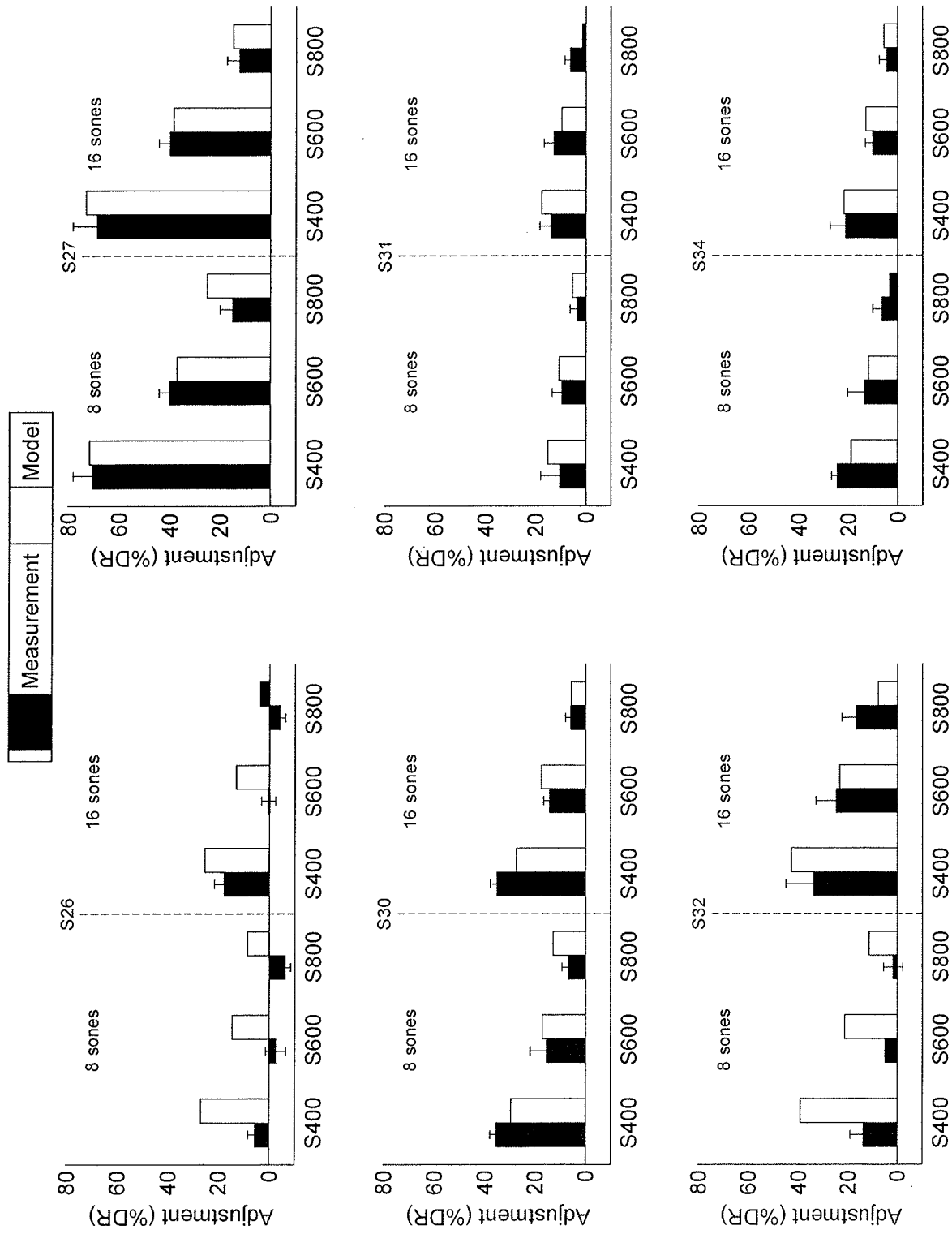
FIG. 6 illustrates monaural balancing results for electric stimulation, for each subject, wherein the black bars indicate the adjustment to make the stimulus indicated on the horizontal axis equally loud as stimulus S1200 and the white bars indicate predictions made by the loudness model. The error bars indicate one standard deviation.
Figure 7:
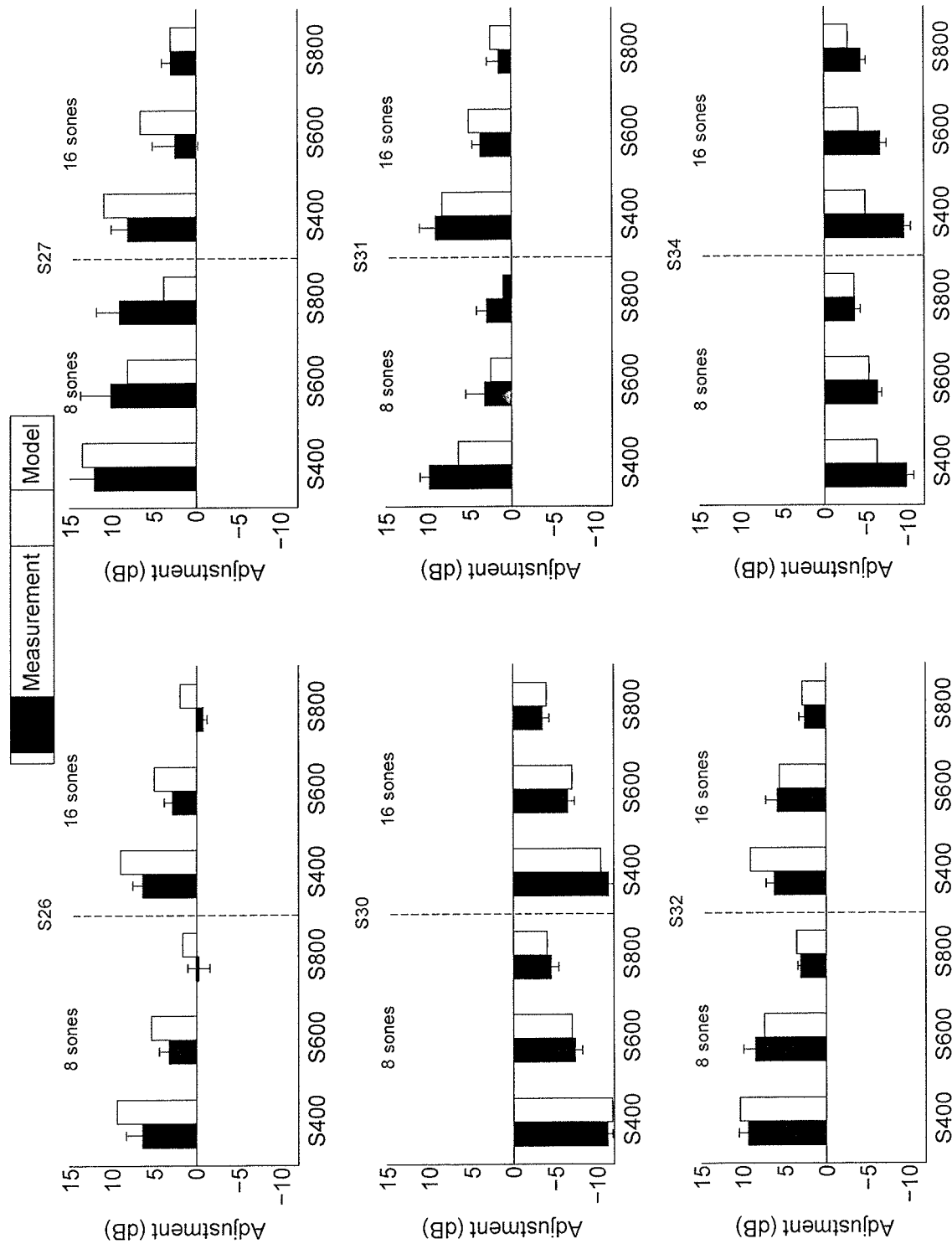
FIG. 7 illustrates monaural balancing results for acoustic stimulation, wherein the black bars indicate the adjustment to make the stimulus indicated on the horizontal axis equally loud as stimulus S1200 and wherein the white bars indicate predictions made by the loudness model. The error bars indicate one standard deviation.

The monaural balancing results and model predictions are shown in FIG. 6 for the electric model and in FIG. 7 for the acoustic model. The black bars indicate the adjustment to make the stimulus indicated on the horizontal axis equal in loudness to stimulus S1200. The white bars indicate predictions made using the loudness model. The closer the white bar is to the corresponding black one, the better the model prediction.

Figure 8:
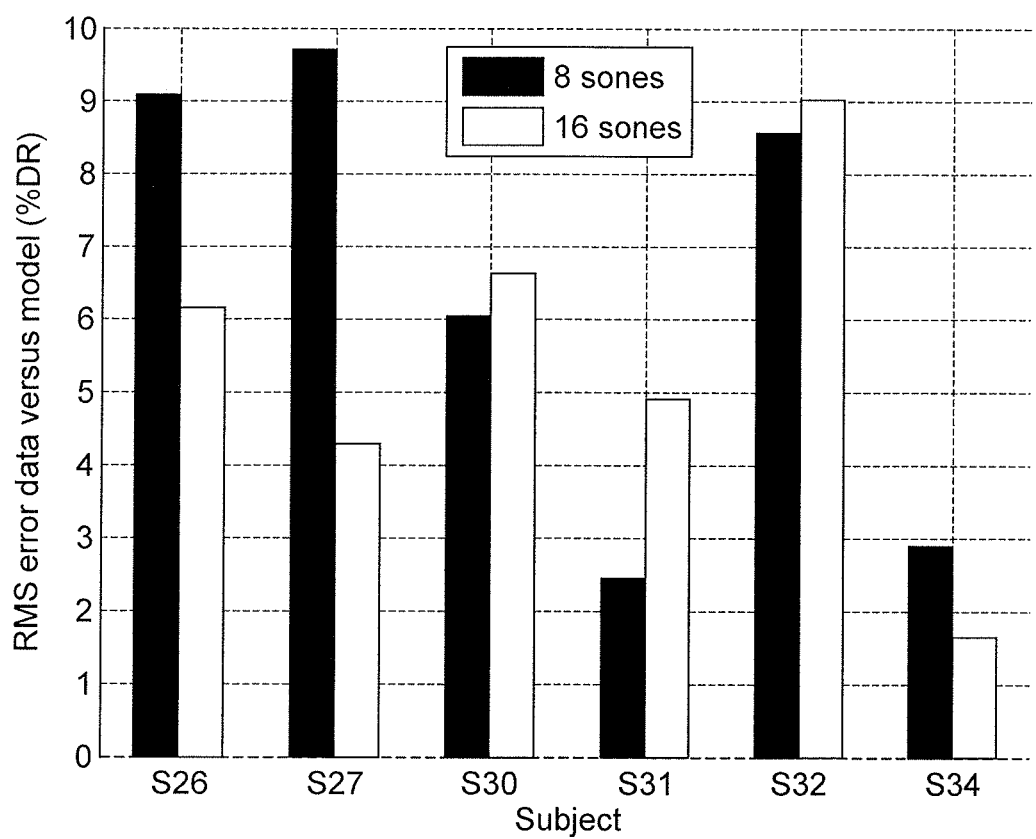
FIG. 8 illustrates the RMS error of the difference in adjustment between adjacent stimuli and the corresponding model predictions, for monaural electric stimulation. Smaller values indicate better performance of the model.

RMS errors for each subject for the two target loudnesses for the electric model are shown in FIG. 8. With reference to the results for S26 at 8 sones, the balancing adjustments for [S400 S600 S800 S1200] were [5.7 −2.5 −6.3 0]% DR (note that the value of 0% DR for S1200 was not measured, it is clear that an adjustment of 0% DR is utilitarian to make a stimulus equally loud to itself), and the corresponding differences [−8.2 −3.8 6.3]% DR. The adjustments predicted by the model were [27 15 8.7]% DR, with corresponding differences of [−12 −5.9 −8.7]% DR. The RMS difference between [−8.2 −3.8 6.3] and [−12 −5.9 −8.7] is 9.1% DR. The RMS errors for 8 and 16 sones were compared across all subjects using a Wilcoxon signed rank test, which indicated no statistically significant difference (p=0.69). This indicates that the model prediction errors were not significantly different between the two target loudnesses. RMS errors ranged from 2 to 10% DR with a mean of 5% DR.

Figure 9:
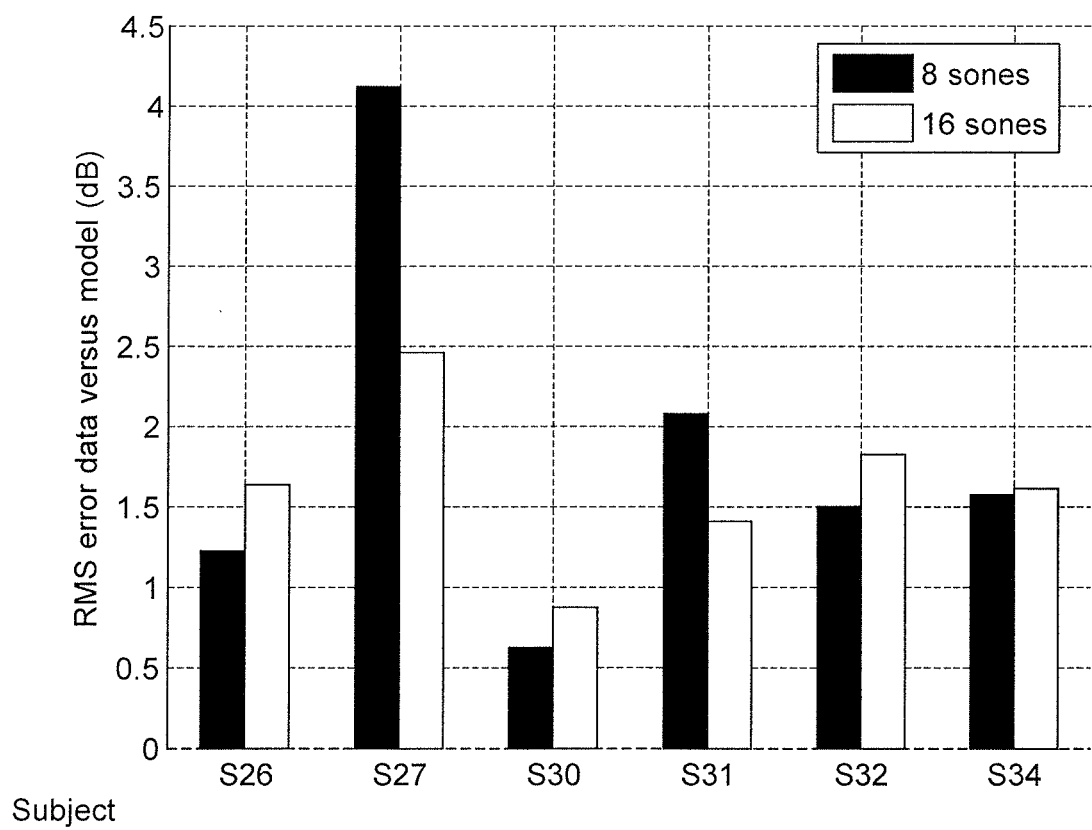
FIG. 9 illustrates the RMS error of the difference in adjustment between adjacent stimuli and the corresponding model predictions, for monaural acoustic stimulation. Smaller values indicate better performance of the model.

FIG. 9 shows the same analysis for the acoustic model. A Wilcoxon signed rank test indicated no significant difference in RMS error between the two target loudnesses (p=1.00). RMS errors ranged from 0.6 to 4.1 dB with a mean of 1.7 dB across subjects and loudnesses.

Concluding, in FIGS. 8 and 9 the RMS error of the difference in adjustment between adjacent stimuli and the corresponding model predictions, for monaural electric stimulation are shown. Smaller values indicate better performance of the model.

Figure 10:
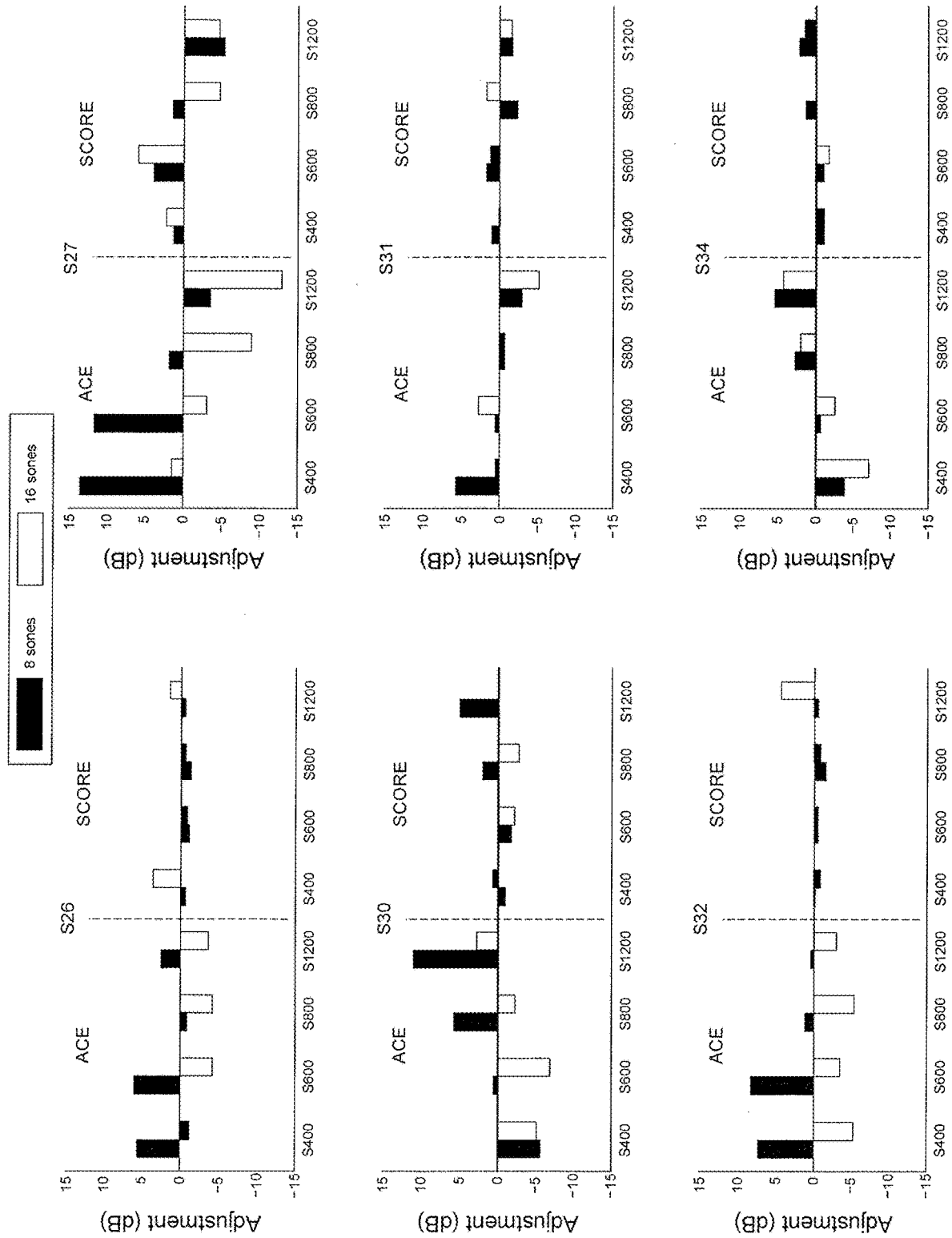
FIG. 10 illustrates binaural balancing adjustments for each subject, at 8 and 16 sones, for processing conditions ACE and SCORE bimodal. The bars indicate the adjustment of the acoustic side to binaurally balance the stimulus indicated on the horizontal axis.
Figure 11:
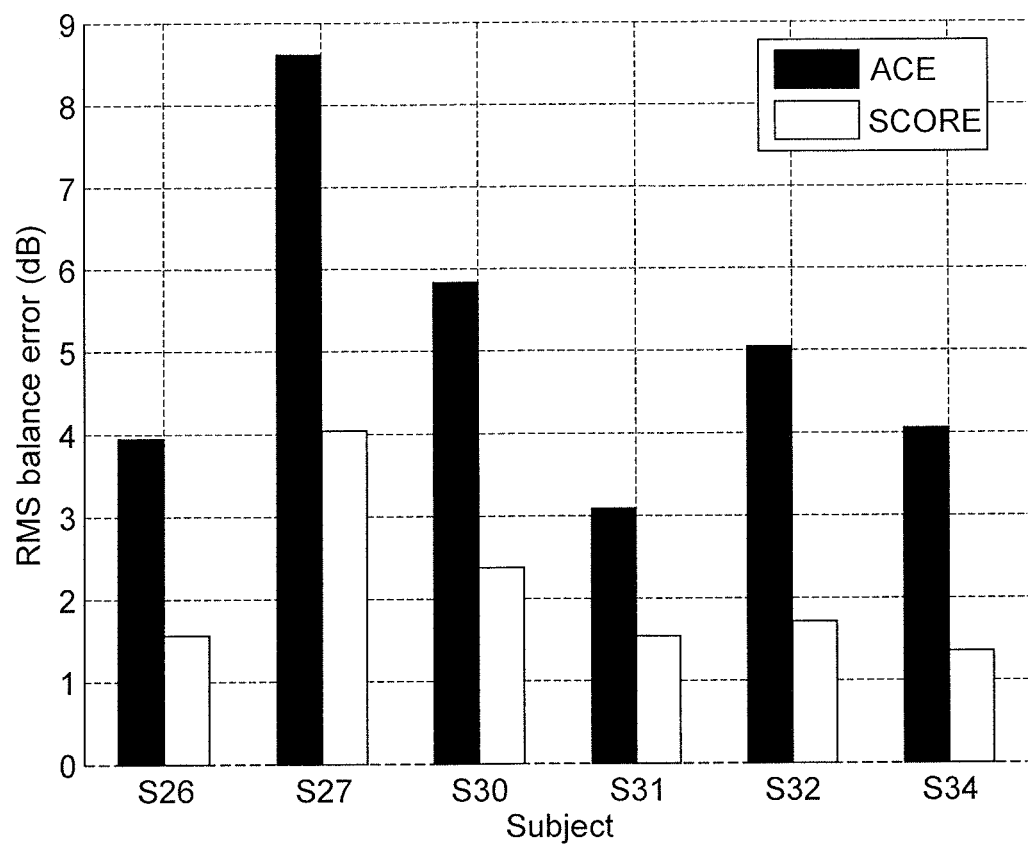
FIG. 11 illustrates the RMS error of the binaural balancing adjustments for each subject in the two processing conditions.
Figure 12A:
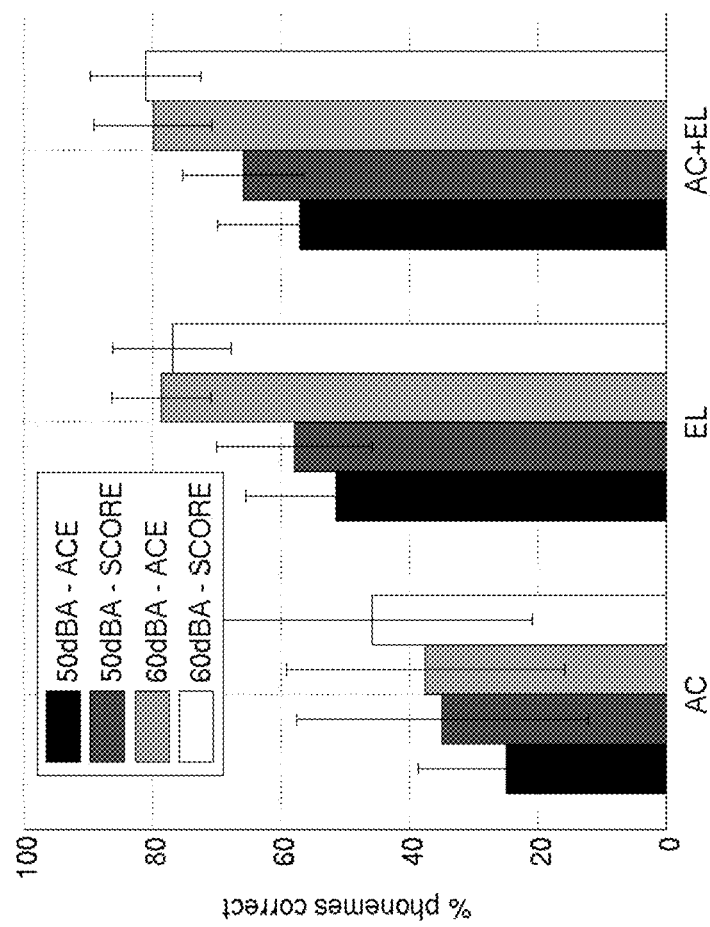
FIG. 12A illustrates across subject average results for speech perception in quiet at 50 dBA and 60 dBA with ACE and SCORE bimodal using the CNC materials. The horizontal axis indicates modality: acoustic only (AC), electric only (EL), or bimodal (AC+EL).
Figure 12B:
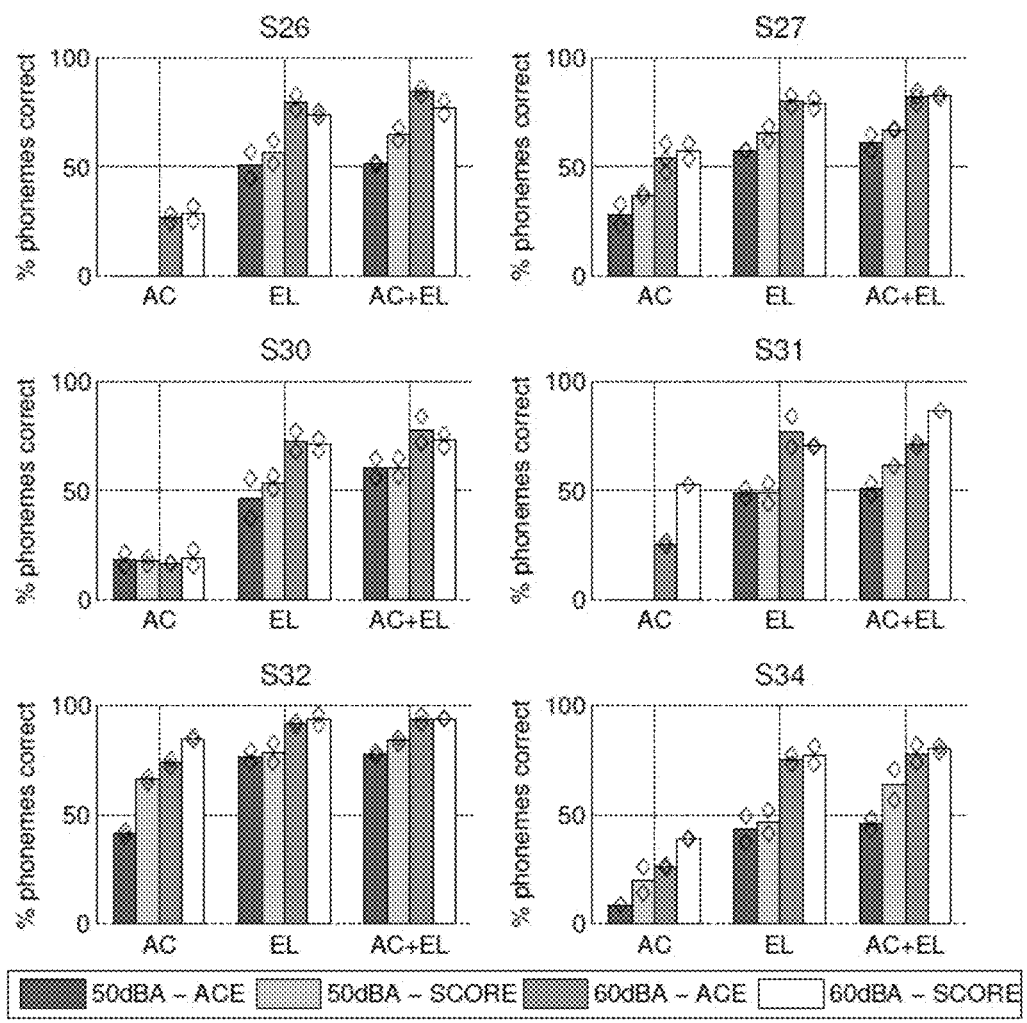
FIG. 12B illustrates individual results of speech perception in quiet at 50 and 60 dB A presentation level, either acoustic only (AC), electric only (EL), or bimodal (AC+EL) for each subject, the diamonds indicate results for individual lists.
Figure 12C:
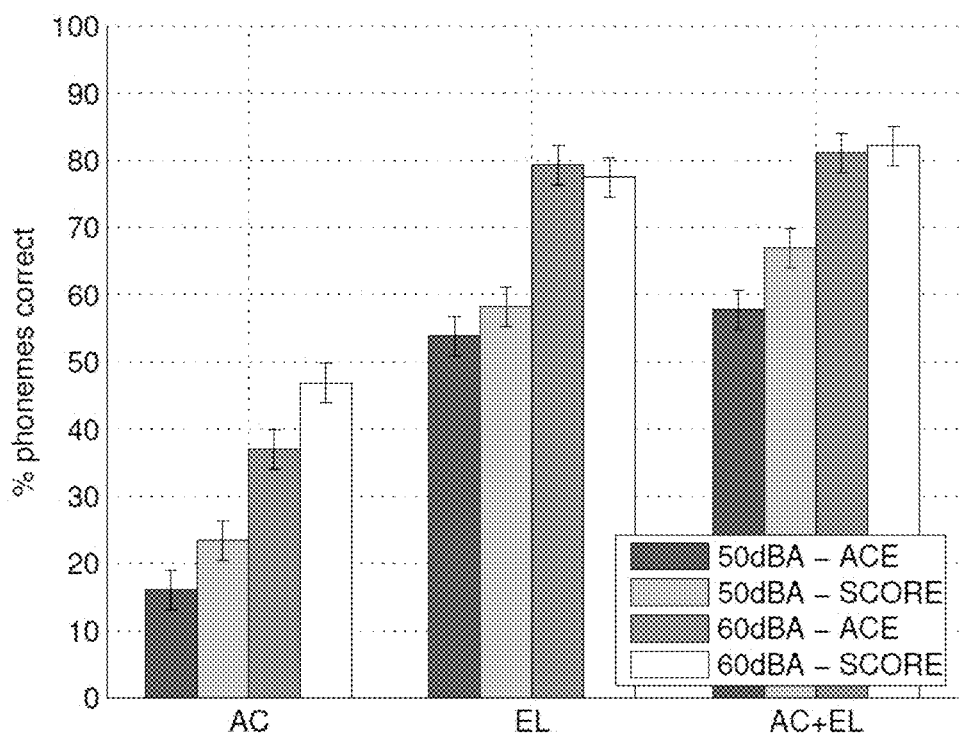
FIG. 12C illustrates across subject average results for speech perception in quiet whereby the total error bar length indicated Fletcher's least significant difference.

The binaural balancing results are shown in FIG. 10, which provides an indication regarding if SCORE improves binaural balance as compared to ACE known in the art. The stimuli used were the same as for the monaural balancing, namely S400, S600, S800 and S1200 and were identical for the two ears prior to processing. The binaural loudness balancing was performed by simultaneous stimulation and interleaved 1|12 AFC 1up/2down and 2up/1down adaptive procedure. The bars indicate the adjustments for the sound to be perceived either in the middle of the head or equally loud in the two ears, with and without application of SCORE. Thus the bars indicate the adjustment of the acoustic side to binaurally balance the stimulus indicated on the horizontal axis. The average adjustment across all stimuli and levels was subtracted from the results as it corresponds to a change of the "volume" control of the HA. As the stimulus at the input of the processing was identical at the left and right sides, the adjustment would ideally be 0 dB. Deviations from 0 dB indicate distorted interaural loudness relations. For ACE there were relatively large errors (adjustments), up to ±10 dB, which is a large proportion of most subjects' acoustic dynamic ranges. For SCORE the remaining errors were usually much smaller. A repeated-measures ANOVA of the absolute value of the adjustment with factors stimulus type was performed, processing (ACE or SCORE), and loudness (8 or 16 sones). There was a significant effect of processing (F(1, 7)=29.8, p<0.01), and no effect of stimulus type or loudness, or their interaction. RMS balance errors for ACE and SCORE are shown in FIG. 11. The average RMS errors for ACE and SCORE respectively were 5.1 dB and 2.1 dB. In spite of some remaining model prediction errors in the monaural balancing experiments, SCORE generally improved binaural loudness balance error for all subjects. This benefit was significant in a Wilcoxon signed rank test (p=0.03).

The SCORE bimodal signal processing strategy which normalizes loudness using models of loudness perception that run in real-time on the two devices. Normal-hearing loudness is estimated at microphone level for each ear, hearing-impaired and CI loudness are estimated after hearing aid and CI speech processing respectively, and the overall output level is adjusted to equalize the loudness of the final outputs to the normal hearing ones. SCORE bimodal has been shown to improve binaural balance.

Figure 15:
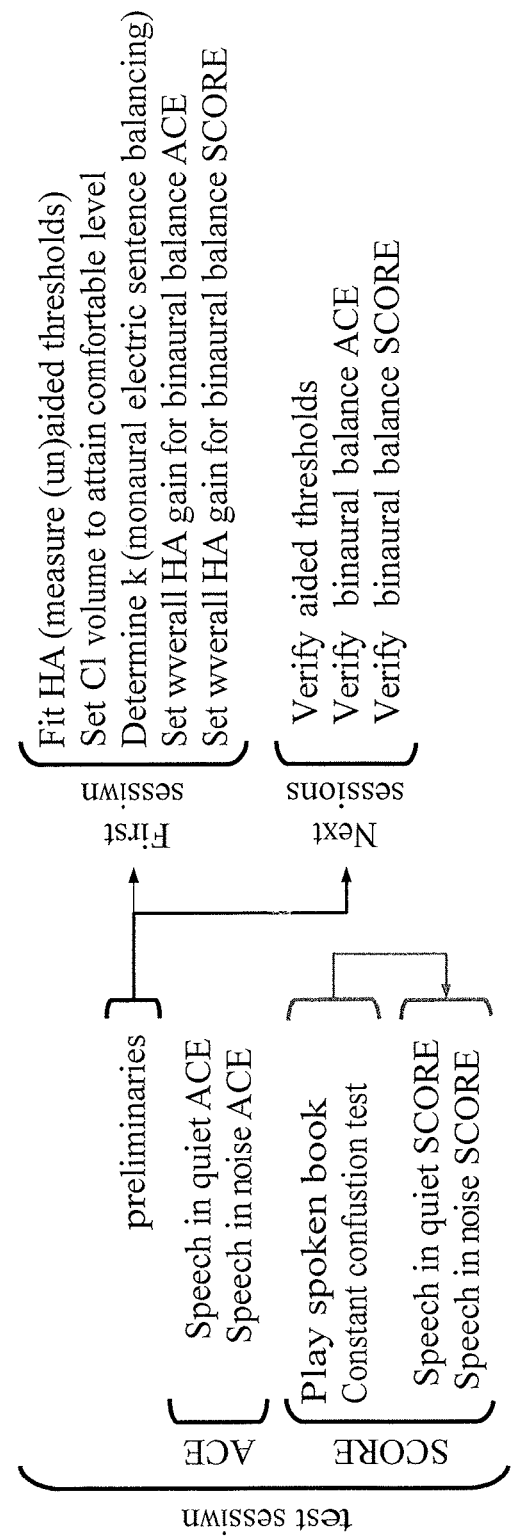
FIG. 15 illustrates a schematic overview of a test session for speech perception.
Figure 16:
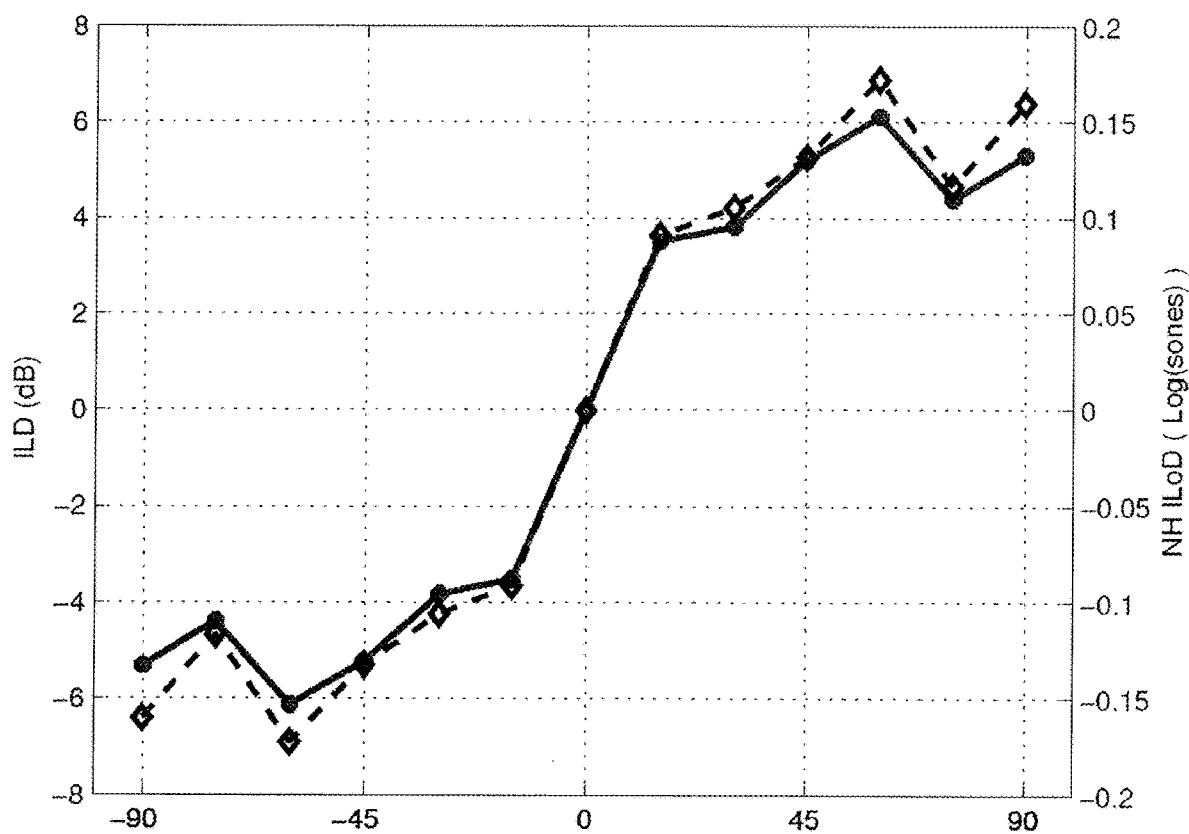
FIG. 16 illustrates interaural level and loudness differences for the speech-weighted click train used in the localization experiments and simulations. ILDs in dB are shown in blue with round markers and the corresponding interaural loudness differences for a normal-hearing listener are shown with diamond markers.

A schematic overview of a test session for obtaining results regarding speech perception and localization with SCORE bimodal is shown in FIG. 15. Six subjects were recruited who also participated in our previous SCORE study. They used a CI and contralateral HA on a daily basis. Their audiograms and other relevant information are shown in Table 2.

TABLE 2

| | Age | CI use | CI | | Unaided threshold (dB HL) | | | | | |
|---|---|---|---|---|---|---|---|---|---|---|
| Subject | (y) | (y) | side | Aetiology | 250 | 500 | 1000 | 2000 | 4000 | 8000 Hz |
| S26 | 75 | 1.7 | R | Unknown | 60 | 65 | 70 | 75 | 85 | 75 |
| S27 | 78 | 2.4 | L | Unknown | 75 | 70 | 65 | 60 | 60 | 100 |
| S30 | 60 | 2.6 | R | Unknown | 30 | 55 | 100 | — | — | — |

TABLE 2-continued

| Subject | Age (y) | CI use (y) | CI side | Aetiology | Unaided threshold (dB HL) | | | | | |
|---|---|---|---|---|---|---|---|---|---|---|
| | | | | | 250 | 500 | 1000 | 2000 | 4000 | 8000 Hz |
| S31 | 62 | 1.7 | R | Unknown | 70 | 75 | 90 | 80 | 105 | — |
| S32 | 54 | 7.2 | R | Meniers | 70 | 85 | 80 | 80 | 80 | 100 |
| S34 | 53 | 2.6 | R | Unknown | 50 | 60 | 85 | — | — | — |

In Table 2 subject details are presented. "Age" is in years at the time of testing. "CI use" is the number of years of implant use at the time of testing. "CI side" is left (L) or right (R); the HA was on the other side. Unaided pure-tone thresholds are given in dB HL. Unmeasurable thresholds are indicated by a dash.

For the CI sound processor, the clinical fitting was used, with the volume set to a level that provided comfortable listening for running speech presented at 60 dB A. SCORE utilizes parameter a to be determined during fitting. The value previously determined using loudness balancing experiments for these six subjects as described above was utilized. For the HA, target aided thresholds were calculated according to the NAL-RP rule. Aided thresholds were measured through the simulated HA and gains were adjusted to attain the target aided thresholds. The overall gain was adjusted to obtain a balanced percept for speech at 60 dB A.

At the beginning of a session, some preliminary tests were done. Then a block of either ACE or SCORE tests was completed. SCORE tests were always preceded by some training, consisting of listening to an audiobook and performing a consonant confusion test with feedback. ACE tests were not preceded by training, as each of the subjects used ACE on a daily basis. More specifically, in pilot tests, no learning effect was found in the ACE condition. When asked, the subjects could not hear a difference between their own processor and the experimental implementation of ACE. In what follows each of these steps is described in detail.

At the beginning of the first test session, the HA was fitted according to the NAL-RP rule. The volume of the CI was set to attain a comfortable and well-audible percept, comparable to the loudness obtained with the subject's own speech processor for sounds at a normal conversational level. The electric loudness model used by SCORE has a parameter k that influences the average stimulation level adjustment that will be applied. In order to conduct a fair comparison between ACE and SCORE, loudness balancing was done with only electric stimulation using a sentence processed by ACE or SCORE, adjusting the k parameter for equal loudness. The sentence was "I like that song", uttered by a female speaker at a level of 60 dB A. In each trial the sentence was presented twice, once processed by ACE and once by SCORE, in random order, and the subject was asked which interval sounded louder overall, the first or the second. k was adapted in a 1-up/1-down adaptive procedure, in steps that corresponded to a level difference of 10% of the dynamic range. The procedure was stopped after 10 reversals and the resulting value of k was calculated as the mean of its values at the last 6 reversals. This procedure was run twice and the final value for k was calculated as the mean of those two runs.

Then binaural loudness balancing was performed between electric and acoustic stimulation, separately for ACE and SCORE. For SCORE the k value determined in the balancing experiment was used. The experimenter adjusted the overall gain of the HA to obtain a balanced percept. The subjects were asked if they perceived a single fused sound image, or rather a separate sound image for each ear. If there was a single sound image, they were asked to indicate for which overall gain the stimulus sounded in the center of the head. If there were two sound images, they were asked to indicate for which overall gain the stimulus sounded equally loud in the two ears. Three out of six subjects perceived a clearly fused sound image. The stimuli at the input of the ACE or SCORE processing were 1-s long long-term average speech spectrum weighted noise, according to ANSI-53.5, and recorded sentences uttered by a male and female speaker at an average level of 60 dB A. Usually the same overall HA gain was found for all three stimuli. If this was not the case, the average gain across these three stimuli was used.

Figure 14A:
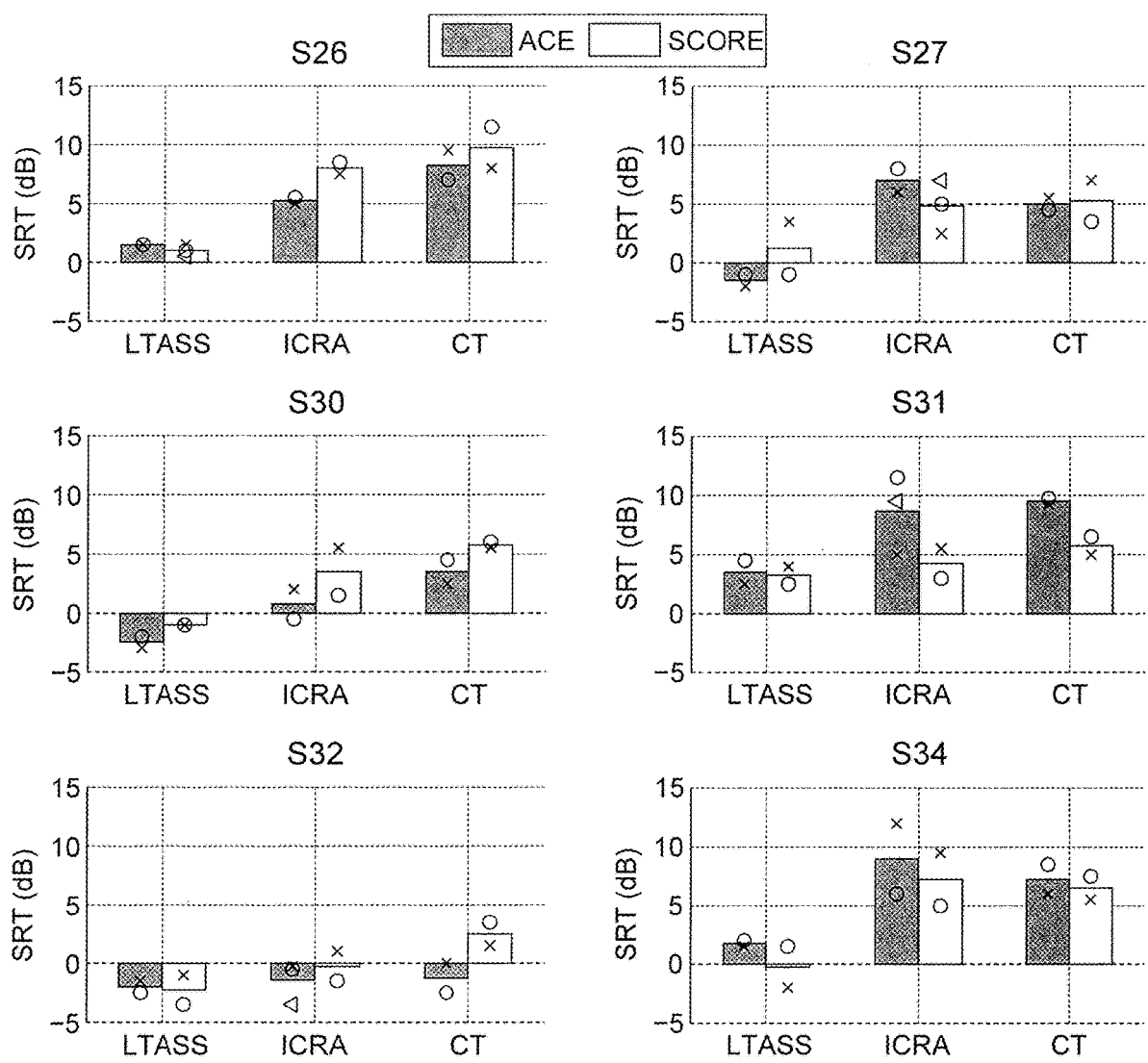
FIG. 14A illustrates individual results for speech perception in noise for ACE and SCORE bimodal according to embodiments of the invention.
Figure 14B:
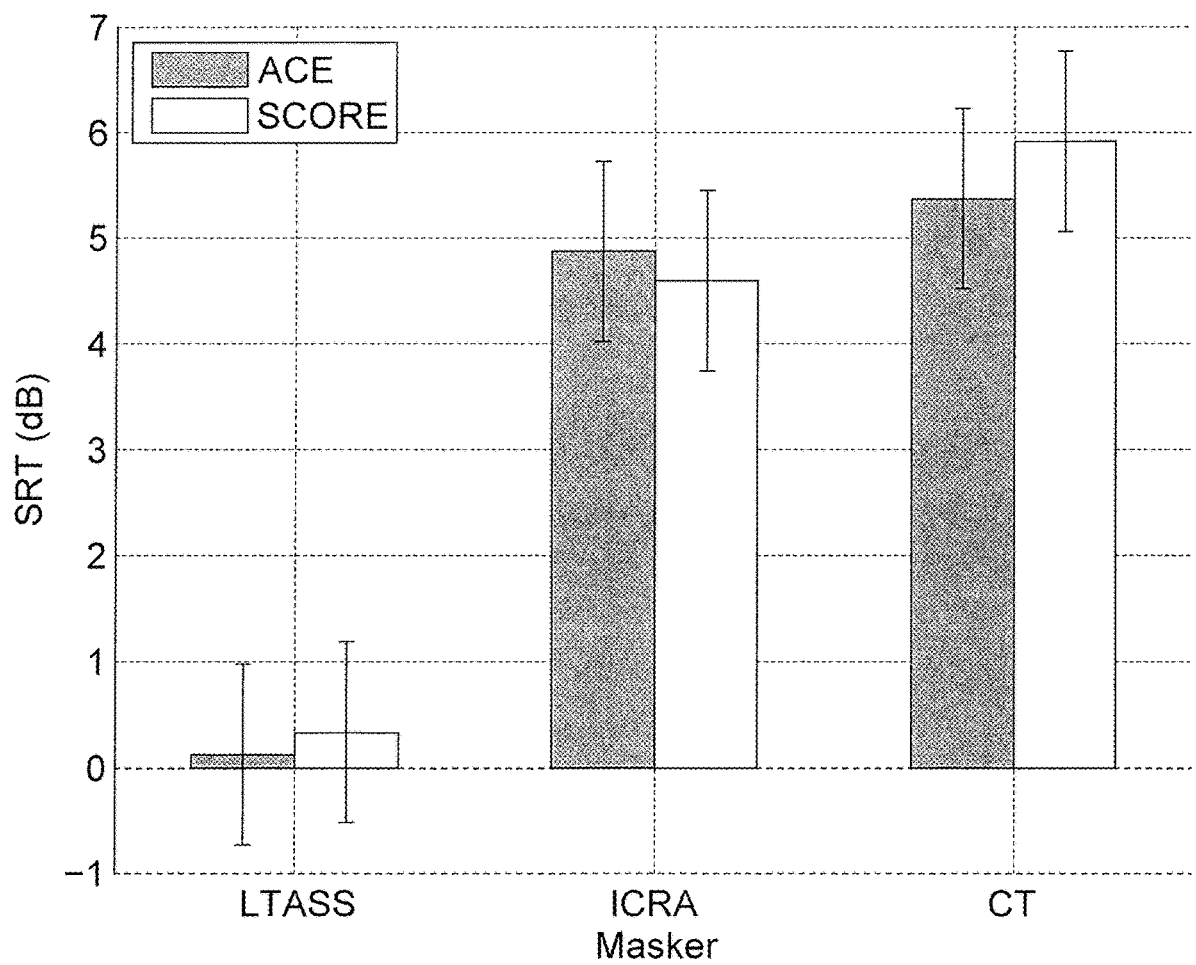
FIG. 14B illustrates average results for speech perception in noise for ACE and SCORE bimodal according to embodiments of the invention.

Individual phoneme scores for speech in noise shown in FIG. 14A and average scores across subjects shown in FIG. 14B provide data of a repeated-measures ANOVA of SRT with factors masker (LTASS, ICRA, or CT), and processing scheme (ACE or SCORE). A Greenhouse-Geisser correction was applied to correct for non-sphericity of factor masker. There was a significant effect of masker ($F(2,25)=29.1$, $p<0.01, \eta 2=0.42$), no effect of processing scheme ($F(1,25)=0.0, p=0.85$), and no effect of the interaction between masker and processing scheme ($F(2,25)=0.49, p=0.63$). The difference in SRT between ACE and SCORE lies with 90% confidence between −1.1 (worse performance with SCORE) and 0.8 dB (better performance with SCORE).

Interaural level and loudness differences in the stimulus were also evaluated, calculated using loudness models as described above. In addition sound source localization experiments were performed and compared with the modeling results. Modeling In what follows a long-term-average-speech-spectrum weighted click train was used as the input stimulus. In the FIG. 7 the ILD of the stimulus at the microphone is shown. The corresponding ILoDs for a normal-hearing listener are also shown, as calculated using the normal-hearing loudness model for a stimulus at 60 dB A. Normal-hearing ILoDs at lower levels were very similar. ILDs and corresponding ILoDs are small: the maximal ILD value is ±6 dB. This means that if no other cues are available for localization, poor performance can be expected, as just-noticeable differences in ILD for normal-hearing listeners are in the order of 1 dB and for bimodal listeners in the order of 1.7 dB. The ILD function is also non-monotonic beyond 45 degrees. This means that it is not possible to distinguish between angles larger than 45 degrees on one side using only ILD cues. Normal-hearing listeners are able to do this using additional cues (interaural time differences and monaural spectral cues). As normal-hearing listeners have the same loudness growth function for both ears, and the loudness growth function is approximately linear for the current range of levels used, the ILoD follows the ILD closely. This illustrates why for normal-hearing listeners the term ILD and ILoD can be used interchangeably.

In FIG. 8, ILoDs are shown for the hearing-impaired bimodal listeners who took part in the current study, calculated with the loudness models configured using their audiograms and CI fitting parameters. The overall level of the acoustic signal was adjusted to obtain loudness balance for the stimulus from 0 degrees at 60 dB A. ILoDs were calculated for the input signal at three different levels: 50, 55, and 60 dB A. ILoDs for a normal-hearing listener are shown in each panel as a reference. SCORE has the effect of changing ILoDs to the normal-hearing ones. The resulting patterns for the hearing-impaired listeners can be broken down into two categories: first, for S26, S27, S31, and S32, who had residual hearing at frequencies beyond 3 kHz, ILoDs for the 60 dB A stimulus follow the normal-hearing one quite closely. While there are some differences, these would probably not have a large perceptual effect. At lower levels, though, the ILoD functions are shifted to the CI side, which means that at these levels the stimulus will be lateralized to the HA side, irrespective of angle of incidence. It can be expected that the application of SCORE in this case might not lead to good sound-source localization, as ILoDs are small, but would lead to correct left-right discrimination. The remaining two subjects, S30 and S34, only had measurable residual hearing below 3 kHz. In this case ILoDs increased with decreasing level, but an extra non-monotonicity was introduced in the ILoD function at around 15-30 degrees. While increased ILoDs could improve localization, this is hampered by the fact that ILoDs are inconsistent across levels: the auditory system presumably "expects" the same ILoD for the same spectrum at different levels. In this case it is not expected that the application of SCORE will improve left-right discrimination, but the reduction of the non-monotonicity at 15-30 degrees could improve localization at those angles.

Depending of the signal's spectral content and the subject's audiogram, different ILoD-versus-angle patterns are possible. Assuming that bimodal listeners only have access to ILoD cues, and not to interaural time differences or detailed monaural spectral cues, localization of the filtered click train stimulus with a spectrum similar to speech, will be poor. It can be expected that application of SCORE will lead to improved left-right discrimination, which is an important ability in real life, for some subjects.

Figure 17:
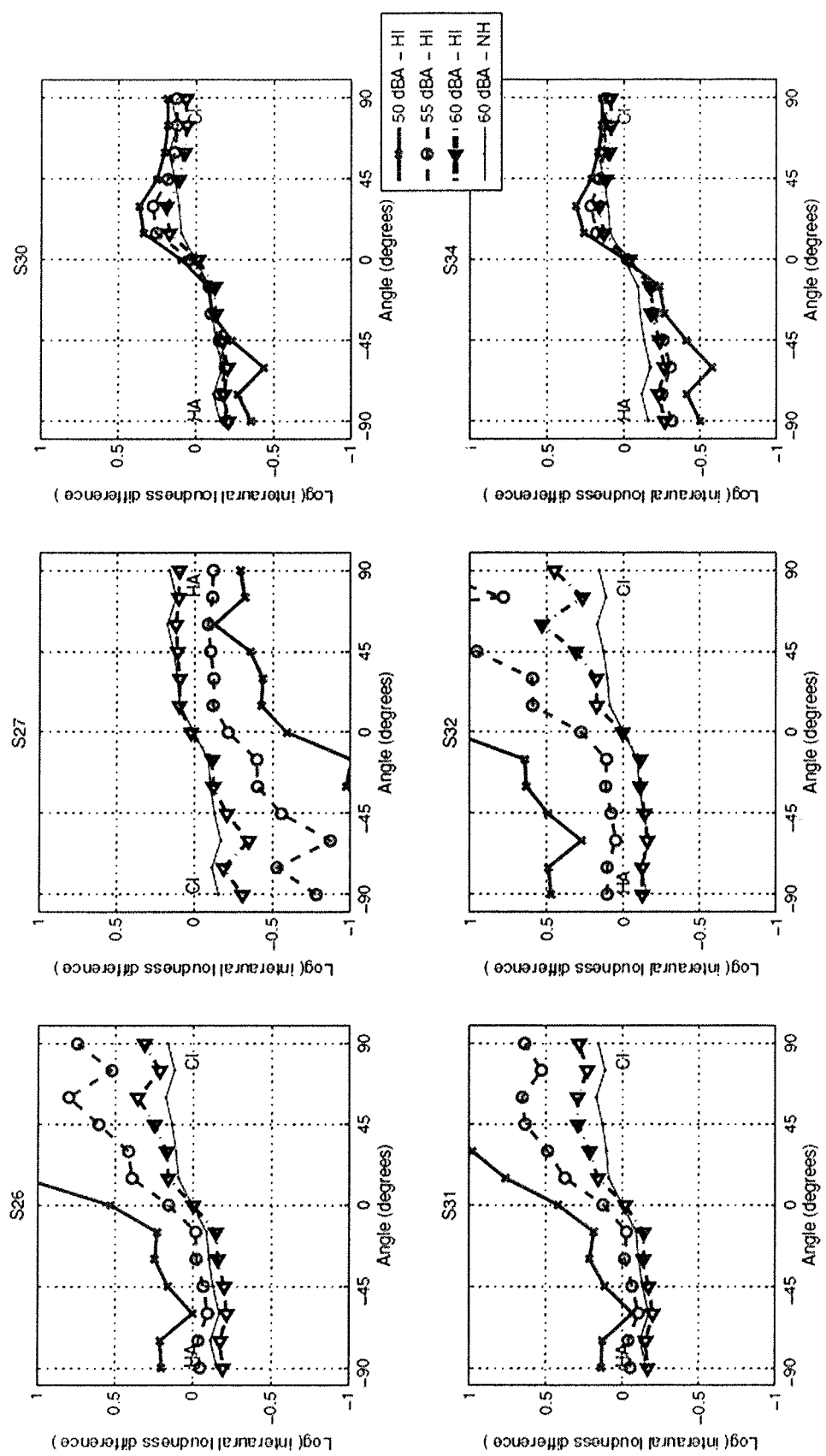
FIG. 17 illustrates interaural loudness differences for a speech-weighted click train, predicted according to the hearing loss of each participant. The thick colored lines indicate IloDs at the output of ACE for different input levels. The thick lines show the loudness after CI and HA processing, taking into account hearing impairment.
Figure 18:
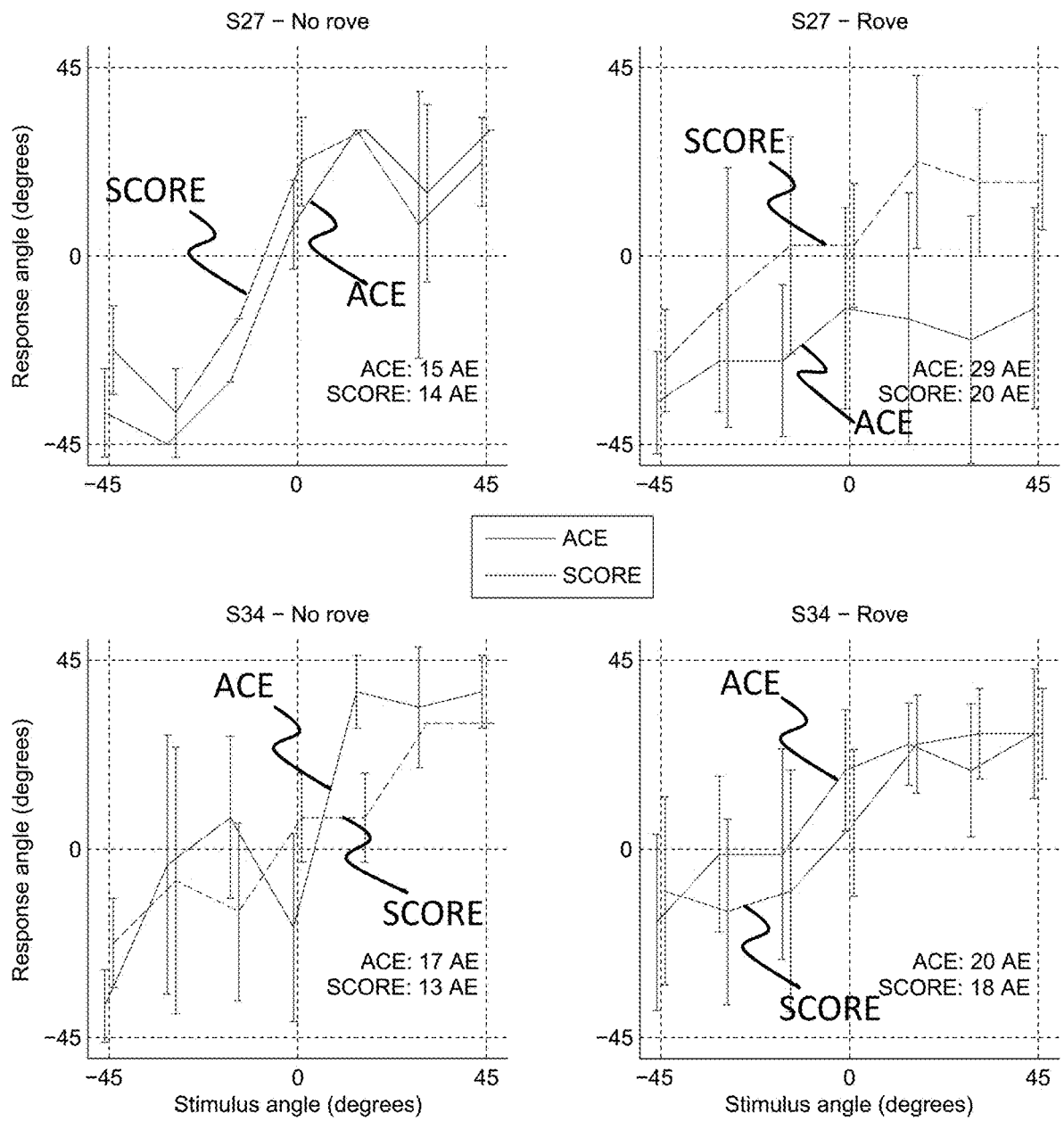
FIG. 18 illustrates localization results with ACE and SCORE bimodal with and without level roving. For each angle the average response and corresponding standard deviations are shown. The overall absolute localization error (AE) in degrees is shown for each condition.

A localization experiment with one subject from each group was performed: S27 and S32. S27 had residual hearing beyond 3 kHz and S32 did not. Stimuli from angles smaller than 45 degrees were only presented, because of the non-monotonicity in the ILD-versus-angle function. In FIG. 18 the localization results for S27 and S34 are shown. For S27 without roving, there was essentially no difference between ACE and SCORE. This corresponds to the observation that the hearing-impaired ILoD in FIG. 17 follows the normal-hearing one. For S27 with roving, there was a big difference. Further analysis of the data (not shown) indicated that for levels lower than 60 dB A, the subject always lateralized the stimulus to the HA side, which again corresponds to the observation that the ILoDs in FIG. 8 for 50 and 55 dB A are below zero for all angles of incidence.

For S34 without roving, the main difference between ACE and SCORE occurred at 15 degrees. In FIG. 17 there is a corresponding non-monotonicity (peak) at 15 degrees in the hearing-impaired functions, which was removed by SCORE. For S34 with roving, there was no clear difference between ACE and SCORE. This can be explained by two counteracting effects. In the ACE condition, larger ILoDs were available at low levels, which improved left-right lateralization, yielding utilitarian value of ACE over SCORE. On the other hand, in the SCORE condition ILoDs were presumably more consistent across levels, yielding utilitarian value for SCORE. Note that overall performance for both subjects was very poor, even though the stimulus from 0 degrees was balanced at 60 dB A, which would not be the case for many stimuli with standard clinical processing. Generally these subjects were able to discriminate between left and right, but could not make a finer distinction between angles of incidence.

As noted above, embodiments provide a loudness equalization strategy and fitting method. The strategy can equalize loudness growth for both modalities using existing models of loudness for both acoustic and electric stimulation, and is suitable for implementation in wearable devices, such as hearing prosthesis systems. Embodiments can provide a normalization strategy for combined cochlear implant and acoustic stimulation. Embodiments can provide a normalization strategy for combined cochlear implant and hearing aid stimulation whereby speech perception and localization with SCORE bimodal is evaluated.

In some exemplary embodiments, some or all of the teachings detailed herein and/or variations thereof can be combined with the teachings of WO0217678 to enable electric stimulation. Some embodiments can be used for bimodal stimulation and validated it with bimodal listeners. More specifically, at least some embodiments can provide for the significant improvement in binaural balance. Moreover, a significant improvement of speech perception in quiet at soft levels, no change of speech perception in quiet at conversational levels, and no change of speech perception in noise can be provided for. In an exemplary embodiment, all of these improvements are relative to that which would be the case for substantially corresponding devices, systems and/or methods, they do not utilize the teachings detailed herein and/or variations thereof (e.g., that do not utilize SCORE).

As noted above, loudness balancing experiments with six bimodal listeners were performed to validate a loudness equalization strategy according to embodiments of the invention. In a first set of experiments, monaural loudness balancing was performed for four harmonic complexes of different bandwidths, ranging from 200 Hz to 1000 Hz. Both the electric and acoustic loudness model according to embodiments of the invention predicted the psychophysical data adequately. In a second set of experiments, binaural balancing was done for the same stimuli. It was found that on average the loudness equalization strategy according to embodiments significantly improved binaural balance by 59 percent relative to that which would be the case in the absence of the utilization of the teachings detailed herein and/or variations thereof in an otherwise substantially similar and/or the same device, system and/or method. This is an example of the exemplary embodiment in which the first and second subsystems 201R and 201L are configured to automatically cause target recipient perception of loudness of the respective evoked hearing percepts to correspond at least substantially more (which includes corresponding exactly) to that which would be perceived by a normal hearing listener, at least based on an estimate thereof, as noted above with respect to FIG. 2A.

It is noted that in some embodiments of bimodal stimulation according to the teachings detailed herein, the same acoustic stimulus often leads to activation of different regions in the two cochleas, such that normalizing specific loudness at each ear would not necessarily normalize interaural balance. Next to these practical issues, normalizing total loudness can have utilitarian value with respect to other features. For example, current bimodal listeners are implanted because their speech perception with only acoustic stimulation is poor. As a consequence, they use their acoustic hearing mainly to provide cues complementary to the electric stimulation, and to perceive binaural cues. To be able to use the complementary cues, the acoustic signal should be audible and there should be binaural fusion. Given that similarity is one of the auditory grouping cues, equal loudness can improve binaural fusion in at least some embodiments. For listeners with a broad high-frequency dead region, binaural balance for a broadband sound might not be achieved by normalizing specific loudness. It should be noted though that normalizing the loudness might not be beneficial for signals with only high-frequency content, that fall entirely in a high-frequency dead region of the acoustically stimulated ear. In this case there is no energy at frequencies that can be made audible. Some embodiments of SCORE copes with this by not adjusting the level if the loudness estimated by the model for HI is below a threshold value.

The results from the binaural balancing experiments indicate that the application of SCORE improved binaural balance, which will likely lead to improved listening comfort and better perception of interaural level differences, relative to that which would be the case in the absence of score, all other things being equal, leading to improved sound-source localization ability. In at least some embodiments, there can also be a results in improved perception of interaural time differences, as this requires binaural balance. While in the current study SCORE was evaluated for bimodal stimulation (HA and CI in opposite ears), with some modifications it is also suitable for hybrid stimulation (HA and CI in the same ear) in at least some embodiments. In this case, the specific loudness integrated across the respective frequency ranges of acoustic and electric hearing could be normalized, instead of the total loudness, as is done for SCORE bimodal. According to an exemplary embodiment, the SCORE strategy is a strategy and fitting method specifically designed for combined electric and acoustic hearing.

Pilot experiments and theoretical considerations indicate that at in least some embodiments of SCORE bimodal, SCORE bimodal improves sound source localization performance. SCORE bimodal is a practical solution for the long standing problem of fitting and balancing bimodal devices, with a fairly low computational complexity.

Embodiments can be applied to bimodal and hybrid stimulation: loudness-model based processing is also applied to the acoustic signal and the parameters are selected as to optimize binaural balance and transmit interaural level difference cues. Other embodiments can provide a signal processing method to normalize the total loudness of an acoustic signal.

Embodiments can provide a clinically-feasible fitting method for the electric loudness model (loudness balancing between signals of different bandwidths, iterative calculation of parameters, e.g. a and k parameters).

According to some embodiments, there is provided a bimodal system comprising heuristics that can be utilitarian in that it can be for smoothing gains and/or adjustments, whereby said heuristics comprise at least one of the following steps:

Do not apply adjustment if target (NH) loudness is below a threshold;
Do not apply adjustment if CI/HI loudness is below a threshold;
Limit adjustment if slope of target (NH) loudness is above a threshold;
If no adjustment to be applied, return to default adjustment (0 dB/0% DR) at a certain rate;
Limit maximal gain/adjustment change between two frames to a maximum value;
Limit minimal and maximal gain/adjustment.

Some embodiments utilize a simplification of the electric loudness model, whereby the model is simplified to only use the linear part of the pulse loudness growth function.

According to some exemplary embodiments, the target loudness is transformed from NH to any desired function/ any utilitarian function. By way of example, there can be instances where adjusting the outputs of the stimulator specific sound processor section 224 to obtain a loudness corresponding to that which would be different than that for normal hearing can have utilitarian value. In an exemplary embodiment, relatively very low and relatively very high target values, such as corresponding to very soft sounds (e.g., loudness less than 1 sone) or to very loud sounds (e.g., loudness more than 30 sones), are transformed to different values that are closer to the average.

Still further by example, the desired function/utilitarian functions are not linked to statistical norms, at least not directly. That is, specific values can be identified corresponding to the desired function/utilitarian functions. For example, if the normal hearing loudness corresponds to a value less than 1 sone, the desired function/utilitarian function can be 1 sone (i.e., the signal outputted from stimulation specific sound processor section 224 is adjusted such that the hearing percept should have a loudness of 1 sone). Still further by example, if the normal hearing loudness corresponds to a value more than 20 sones, the desired function/ utilitarian function can be 20 sones (i.e., the signal outputted from stimulation specific sound processor section 224 is adjusted such that the hearing percept should have a loudness of 20 sones).

Any transformations can be used, such as, for example, increasing or decreasing loudness differences relative to that of the normal hearing. Increasing could lead to improved loudness discrimination, but reduced dynamic range, and decreasing could lead to reduced loudness discrimination, but increased dynamic range.

It is again noted that while embodiments have been described with reference to bimodal stimulation (e.g. HA and CI in opposite ears) however embodiments also include other configurations, e.g. for hybrid configuration (CI and HA in the same ear) where one can calculate target (NH) loudness for 2 frequency bands, 1 low-frequency (for acoustic stimulation) and 1 high-frequency and use those as targets for electric and acoustic stimulation.

At least some of the teachings detailed herein and/or variations thereof can be used for any combination of CI and HA in the two ears (e.g., hybrid and contralateral HA or bilateral hybrids), where one can work in multiple frequency bands instead of only normalizing total loudness.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A hearing system, comprising:
a first sub-system configured to evoke a hearing percept based on a first principle of operation; and a second sub-system configured to evoke a hearing percept based on at least one of the first principle of operation or a second principle of operation different from the first principle of operation, wherein at least one of the first or second sub-systems are configured to process input indicative of an ambient sound while taking into account the operation of the other of the first and second sub-systems to automatically harmonize recipient perception of loudness balancing between the respective evoked hearing percepts.

2. The hearing system of claim 1, wherein:
the first and second sub-systems are configured to process input indicative of the ambient sound while taking into account the operation of the other of the first and second sub-systems to automatically cause recipient perception of loudness of the respective evoked hearing percepts to correspond at least more to that which would be perceived by a normal hearing listener than that which would be the case without the first and second sub-systems taking into account the other of the first and second sub-systems.

3. The hearing system of claim 1, wherein:
the first and second sub-systems are also configured to function in the complete absence of the other of the first and second sub-systems.

4. The hearing system of claim 1, wherein:
the system is configured so that the processing results in respective evoked hearing percepts that at least substantially correspond to that of normal hearing.

5. The hearing system of claim 1, wherein:
the system includes a first sound capture device and a second sound capture device separate from the first sound capture device; and
the first sub-system receives input from the first sound capture device and the second sub-system receives input from the second sound capture device.

6. The hearing system of claim 1, wherein:
the first sub-system includes:
a first sound processor system configured to receive first input from a first sound capture device; and
the second sub-system includes:
a second sound processor system configured to receive second input from a second sound capture device separate from the first sound capture device.

7. The hearing system of claim 1, wherein:
the first sub-system is a cochlear implant system; and
the second sub-system is a mechanical stimulation system separate from the cochlear implant system and configured to evoke a hearing percept via one of bone conduction or direct acoustic cochlear stimulation.

8. The hearing system of claim 1, wherein:
the first principle of operation and the second principle of operation are the same.

9. The hearing system of claim 1, wherein:
the first and second sub-systems are configured to independently process respective inputs according to separate sound processing strategies different from each other.

10. The hearing system of claim 1, wherein:
the second sub-system is configured to evoke a hearing percept based on the first principle of operation.

11. The hearing system of claim 1, wherein:
the second sub-system is configured to evoke a hearing percept based on the second principle of operation different.

12. The hearing system of claim 1, wherein:
the second sub-system is configured to evoke a hearing percept based on the first principle of operation and the second principle of operation.

13. The hearing system of claim 1, wherein:
the first sub-system is configured to evoke a hearing percept based on the second principle of operation.

14. The hearing system of claim 1, wherein:
the first sub-system is a cochlear implant system; and
the second sub-system is a non-electric stimulation system separate from the cochlear implant system.

15. The hearing system of claim 1, wherein:
the hearing system is configured to adjust magnitudes of outputs of the first sub-system based on the ambient sound and magnitudes of outputs of the second sub-system also based on the ambient sound thereby providing a recipient of the hearing system effectively consistent interaural level cues when the ambient sound originates from directions other than straight ahead of the recipient for a plurality of directions substantially to the left and to the right of straight ahead of the recipient.

16. The hearing system of claim 1, wherein:
the first sub-system is a cochlear implant system; and
the second sub-system is a cochlear implant.

17. The hearing system of claim 1, wherein:
the hearing system is in signal communication with a fitting system.

18. The hearing system of claim 1, wherein:
the hearing system is a hearing prosthesis fitted to a recipient to the hearing system.

19. A hearing system, comprising:
a first sub-system configured to evoke a hearing percept based on a first principle of operation; and
a second sub-system configured to evoke a hearing percept based on at least one of the first principle of operation or a second principle of operation different from the first principle of operation, wherein
at least one of the first or second sub-systems include means for processing input indicative of an ambient sound to automatically harmonize recipient perception of loudness balancing between the respective evoked hearing percepts.

20. The hearing system of claim 19, wherein the means for processing processes the input indicative of the ambient sound while taking into account the operation of the other of the first and second sub-systems.

* * * * *